United States Patent
Hasegawa et al.

(10) Patent No.: US 6,313,153 B1
(45) Date of Patent: *Nov. 6, 2001

(54) COMPOSITIONS AND METHODS FOR TREATING NEPHRITIS AND INHIBITING TGF-β RELATED CONDITIONS USING PYRIDYLACRYLAMIDE DERIVATIVES

(75) Inventors: Yoshihiro Hasegawa; Shouichirou Shindou; Tomohisa Hattori; Yousuke Yamazaki; Tatsuhiro Obata; Fumiko Horiuchi; Hiroyuki Hayakawa; Hiroaki Kumazawa, all of Ibaraki (JP)

(73) Assignee: Tsumura & Co., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/463,511
(22) PCT Filed: Jul. 24, 1998
(86) PCT No.: PCT/JP98/03312
§ 371 Date: Jan. 21, 2000
§ 102(e) Date: Jan. 21, 2000
(87) PCT Pub. No.: WO99/05109
PCT Pub. Date: Feb. 4, 1999

(30) Foreign Application Priority Data

Jul. 25, 1997 (JP) .................................................. 9-200169
Oct. 21, 1997 (JP) .................................................. 9-288083

(51) Int. Cl.[7] ........................ C07D 213/42; A61K 31/44
(52) U.S. Cl. ...................... 514/357; 514/341; 546/275.1; 546/336
(58) Field of Search ............................. 546/336, 275.1; 514/357, 341

(56) References Cited

U.S. PATENT DOCUMENTS 3,494,936   2/1970   Weyer et al. .................. 260/332.2

FOREIGN PATENT DOCUMENTS 0 887 340    12/1998   (EP) ............................. C07C/235/34
6 509 697     2/1966   (NL) ............................. C07C/3/00
WO 93/04035 *  3/1993   (WO) ............................. 514/357
WO 96/33997   10/1996   (WO) ............................. C07D/471/04

OTHER PUBLICATIONS

Farbwerke Hoechst, Chem. Abstracts, vol. 65, No. 3, Abstract 5442b, Aug. 1996.*
Findlay, et al., "Triprolidine Radioimmunoassay: Disposition in Animals and Humans," Journal of Pharmaceutical Sciences (1984) vol. 73, No. 10, pp. 1339–1344.

* cited by examiner

Primary Examiner—Zinna Northington Davis
(74) Attorney, Agent, or Firm—Fish & Richardon P.C.

(57) ABSTRACT

The present invention relates to an agent for treating nephritis and a TGF-β inhibiting agent comprising as an effective ingredient a pyridylacrylamide derivative represented by the following formula (I):

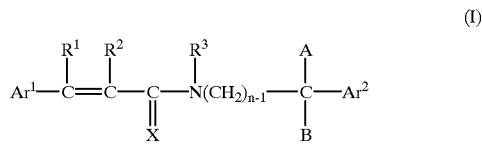

(I)

wherein $Ar^1$ is a substituted or unsubstituted pyridyl group, $Ar^2$ is a substituted or unsubstituted phenyl group, $R^1$ is a hydrogen atom, an alkyl group or an aryl group, $R^2$ is a hydrogen atom, an alkyl group, a cyano group or an alkoxycarbonyl group, $R^3$ is a hydrogen atom or an optionally substituted alkyl group, X is an oxygen or sulfur atom, A and B are same or different and each represent a hydrogen atom, a hydroxyl group, an alkoxy group or an alkylthio group, or A and B together form an oxo or thioxo group, or a group represented by the formula: $=N-Y$ in which Y is a dialkylamino, hydroxyl, aralkyloxy or alkoxy group, or a group represented by the formula: $-Z^1-M-Z^2-$ which $Z^1$ and $Z^2$ are same or different and each represent an oxygen or sulfur atom or an imino group optionally substituted by an alkyl group, and M is an alkylene group or a 1,2-phenylene group, or A is a hydroxyl group and B is a 1-alkylimidazol-2-yl group, and n is an integer of 1 to 3, or a pharmaceutically acceptable salt thereof; as well as the pyridylacrylamide derivatives.

16 Claims, No Drawings

US 6,313,153 B1

COMPOSITIONS AND METHODS FOR TREATING NEPHRITIS AND INHIBITING TGF-β RELATED CONDITIONS USING PYRIDYLACRYLAMIDE DERIVATIVES

RELATED APPLICATIONS

The present claims benefit of priority of Patent Convention Treaty (PCT) International Application Serial No.: PCT/JP98/03312, filed Jul. 24, 1997, which claims benefit of priority to JP 1997 288083, filed Oct. 21, 1997; and JP 1997 200169, filed Jul. 25, 1997. Each of the aforementioned applications are explicitly incorporated herein by reference in their entirety and for all purposes.

TECHNICAL FIELD

The present invention relates to pyridylacrylamide derivatives and anti nephritic agents and TGF-β inhibitors comprising the compounds.

BACKGROUND ART

There is no effective method or drug for treating nephritis and artificial dialysis is carried out in patients with chronic nephritis and reduced renal function. Chronic glomerulonephritis is said to play a main role in introducing the artificial dialysis and amounts to about 40% of the original diseases of patients introducing the artificial dialysis. Under these circumstances, the development of excellent agents for treating nephritis is expected from the standpoint of medical administration.

TGF-β (transforming growth factor-β) acts on various cells such as fibroblasts to enhance the production of extracellular matrices such as collagen, and prevents the degradation of the extracellular matrices by proteases. Further, it has been reported to promote the deposition of the extracellular matrices onto cell surfaces. Thus, diseases associated with TGF-β may include liver cirrhosis, pulmonary or other fibrosis, nephritis, chronic renal insufficiency, diabetic nephropathy, and retinopathy.

Therefore, it is expected that any substances inhibiting TGF-β would be effective for such fibrous diseases.

Japanese Patent Laid Open Publication No. 8-333249 discloses that compounds represented by the following formula (A):

(A)

$$HN=\overset{\overset{NH_2}{|}}{C}-A-Phe-E-Ar-R^1$$

wherein A is a single bond or —NH—, E is —OCO— or —COO—, Phe is a 1,4-phenylene group, Ar—R¹ is a phenyl group substituted a group represented by the following formula:

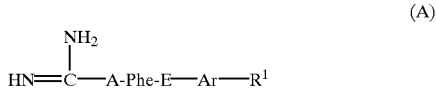

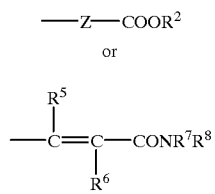

in which Z is a single bond, or a methylene, ethylene or vinylene group, $R^2$ is a hydrogen atom or a $C_{1-4}$ alkyl or —CH$_2$CONR$^3$R$^4$ group, $R^3$ and $R^4$ independently being a hydrogen atom or a $C^{1-4}$ alkyl group, $R^5$ and $R^6$ independently are a hydrogen atom or a $C_{1-4}$ alkyl group, $R^7$ is a $C_{2-6}$ alkenyl group, and $R^8$ is —(CH$_2$)$_n$—COOR$^9$, n being 0 or an integer of 1 to 4 and $R^9$ being a hydrogen atom or a $C_{1-4}$ alkyl group, or salts thereof are useful agents for inhibiting release, activation and synthesis of TGF-β. However, there is no description on the pyridylacrylamide derivatives represented by the formula (I) below which are used as effective ingredients in the pharmaceutical compositions of the present invention.

With respect to the pyridylacrylamide derivatives, on the other hand, WO93/04035 (Japanese Patent Laid Open Publication No. 6-510030) describes the compound represented by the following formula (B):

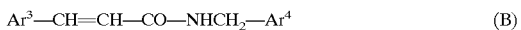

wherein $Ar^3$ is a 3-pyridyl group and $Ar^4$ is a 3,5-di-tert-butyl-4-hydroxyphenyl group as an example of many 3,5-di-tert-butyl-4-hydroxyphenyl derivatives, and shows that the compound is useful as agents for treating metabolic diseases, such as anti-atherosclerosis agents, and may act anti-inflammatory and cytophylatically as well as antasthmatically. However, there is no description suggesting that the compound (B) is useful as anti nephritic agents or TGF-β inhibitors.

DISCLOSURE OF THE INVENTION

It is an object of the present invention to provide a novel pyridylacrylamide derivative and a anti nephritic agent and TGF-β inhibitor comprising the novel or known pyridylacrylamide derivative.

The present inventors have continued researches and studies to develop anti nephritic agents and TGF-β inhibitors and found that specific pyridylacrylamide derivatives are effective as anti nephritic agents and TGF-β inhibitors. Thus, the present invention has been completed.

Accordingly, the present invention includes the following inventions:

(1) an agent for treating nephritis comprising as an effective ingredient a pyridylacrylamide derivative represented by the following formula (I):

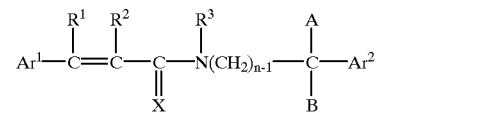

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —Z$^1$M—Z$^2$— in which Z$^1$ and Z$^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof;

(2) a anti nephritic agent of (1) above wherein in the aforementioned formula (I), $Ar^1$ is a pyridyl group substituted by at least one selected from the group consisting of halogen atoms, $C_{1-6}$ alkyl groups, $C_{1-6}$ alkoxy groups and $C_{1-6}$ alkoxy-carbonyl groups;

(3) a anti nephritic agent of (1) above wherein in the aforementioned formula (I), $Ar^2$ is a phenyl group substituted by at least one selected from the group consisting of halogen atoms, a hydroxyl group, optionally substituted amino groups, optionally substituted $C_{1-6}$ alkoxy groups, $C_{2-6}$ alkenyl-oxy groups, aryloxy groups, optionally substituted $C_{1-6}$ alkyl groups, aryl groups, $C_{1-6}$ alkylthio groups, a carboxyl group, $C_{1-6}$ alkoxy-carbonyl groups, a sulfamoyl group and —O—CO—$R^4$ groups in which $R^4$ is a $C_{1-6}$ alkyl, aryl, $C_{1-6}$ alkoxy or optionally substituted amino group;

(4) a TGF-β inhibiting agent comprising a pyridylacrylamide derivative represented by the aforementioned formula (I) or a pharmaceutically acceptable salt thereof as an effective ingredient;

(5) a TGF-β inhibiting agent of (4) above which is a treating agent for a TGF-β-involving disease selected from liver cirrhosis, fibrosis, nephritis, chronic renal insufficiency, diabetic nephropathy, and retinopathy;

(6) a pyridylacrylamide derivative represented by the following formula (I'):

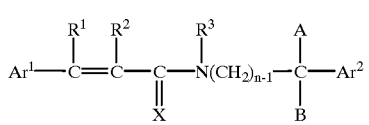

(I')

in $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof, provided that those compounds of the aforementioned formula (I') wherein $Ar^1$ is 3-pyridyl group, $Ar^2$ is 3,5-di-tert-butyl-4-hydroxyphenyl group, $R^1$, $R^2$ and $R^3$ each represent a hydrogen atom, X is an oxygen atom, A and B each represent a hydrogen atom, and n is 1, and salts thereof are excluded;

(7) a compound of (6) above wherein in the aforementioned formula (I'), $Ar^1$ is a pyridyl group substituted by at least one selected from the group consisting of halogen atoms, $C_{1-6}$ alkyl groups, $C_{1-6}$ alkoxy groups and $C_{1-6}$ alkoxy-carbonyl groups; and (8) a compound of (6) above wherein in the aforementioned formula (I'), $Ar^2$ is a phenyl group substituted by at least one selected from the group consisting of halogen atoms, a hydroxyl group, optionally substituted amino groups, optionally substituted $C_{1-6}$ alkoxy groups, $C_{2-6}$ alkenyl-oxy groups, aryloxy groups, optionally substituted $C_{1-6}$ alkyl groups, aryl groups, $C_{1-6}$ alkylthio groups, a carboxyl group, $C_{1-6}$ alkoxy-carbonyl groups, a sulfamoyl group and —O—Co—$R^4$ groups in which $R^4$ is a $C_{1-6}$ alkyl, aryl, $C_{1-6}$ alkoxy or optionally substituted amino group.

In the aforementioned formulae (I) and (I'), the pyridyl group represented by $Ar^1$ includes 2-pyridyl, 3-pyridyl and 4-pyridyl groups and the 2-pyridyl, 3-pyridyl and 4-pyridyl groups may be substituted by any suitable substituent(s), for example, at least one selected from halogen atoms, $C_{1-6}$ alkyl groups, $C_{1-6}$ alkoxy groups and $C_{1-6}$ alkoxy-carbonyl groups.

In the aforementioned formulae (I) and (I'), the substituted phenyl group represented by $Ar^2$ includes, for example, a phenyl group substituted by at least one selected from the group consisting of halogen atoms, a hydroxyl group, optionally substituted amino groups, optionally substituted $C_{1-6}$ alkoxy groups, $C_{2-6}$ alkenyl-oxy groups, aryloxy groups, optionally substituted $C_{1-6}$ alkyl groups, aryl groups, $C_{1-6}$ alkylthio groups, a carboxyl group, $C_{1-6}$ alkoxy-carbonyl groups, a sulfamoyl group and —O—CO—$R^4$ groups in which $R^4$ is a $C_{1-6}$ alkyl, aryl, $C_{1-6}$ alkoxy or optionally substituted amino group.

In the present specification, the $C_{1-6}$ alkyl group and the "$C_{1-6}$ alkyl" in each substituent may be any linear, branched or cyclic ($C_{3-6}$ cycloalkyl) and include, for example, methyl, ethyl, propyl, isopropyl, butyl, isobutyl, sec-butyl, tert-butyl, pentyl, isopentyl, hexyl, cyclopentyl, and cyclohexyl groups. The $C_{1-6}$ alkoxy group and the "$C_{1-6}$ alkoxy" in each substituent include any alkoxy groups derived from the $C_{1-6}$ alkyl groups, such as, for example, methoxy, ethoxy, propoxy, isopropoxy, butoxy, isobutoxy, sec-butoxy, tert-butoxy, pentyloxy, isopentyloxy, hexyloxy, cyclopentyloxy, and cyclohexyloxy groups. Among these groups, most preferred are methyl group for the $C_{1-6}$ alkyl group and methoxy group for the $C_{1-6}$ alkoxy group.

The $C_{1-6}$ alkylthio group includes any $C_{1-6}$ alkylthio groups derived from the $C_{1-6}$ alkyl groups, such as, for example, methylthio, ethylthio, propylthio, isopropylthio, butylthio, isobutylthio, sec-butylthio, tert-butylthio, pentylthio, isopentylthio, hexylthio, cyclopentylthio, and cyclohexylthio groups.

The di($C_{1-6}$ alkyl)amino group includes, for example, dimethylamino and diethylamino groups.

The 1-$C_{1-6}$ alkyl-imidazol-2-yl group includes, for example, 1-methylimidazol-2-yl group.

The $C_{1-6}$ alkoxy-carbonyl group includes any alkoxycarbonyl groups derived from the $C_{1-6}$ alkoxy groups, such as, for example, methoxycarbonyl, ethoxycarbonyl, isopropoxycarbonyl, and butoxycarbonyl groups.

The aryl group may be any optionally substituted phenyl group, such as phenyl or p-methoxyphenyl group. The aryloxy group may be any optionally substituted phenoxy group, such as, for example, phenoxy or p-methylphenoxy group. The aralkyloxy group may be any optionally substituted benzyloxy group.

The halogen atom includes fluorine, chlorine, bromine and iodine atoms.

The $C_{2-6}$ alkenyl-oxy group includes, for example, allyloxy and isobutenyloxy, and the $C_{1-6}$ alkylthio group includes, for example, methylthio and ethylthio groups.

The —O—CO—R⁴ group includes, for example, acetoxy, isobutyryloxy, pivaloyloxy, benzoyloxy, ethoxycarbonyloxy, ethylcarbamoyloxy, and dimethylcarbamoyloxy groups.

The $C_{1-6}$ alkyl group represented by $R^3$ and the $C_{1-6}$ alkyl group as a substituent in the phenyl group represented by $Ar^2$ may be substituted by any suitable substituent(s), for example, at least one selected from $C_{1-6}$ alkoxy-carbonyl groups and halogen atoms. The substituted $C_{1-6}$ alkyl group includes, for example, methoxycarbonylmethyl and trifluoromethyl groups.

The $C_{1-6}$ alkoxy group as a substituent in the phenyl group represented by $Ar^2$ may be substituted by any suitable substituent(s), for example, at least one selected from $C_{1-6}$ alkoxy groups, $C_{1-6}$ alkoxy-$C_{1-6}$ alkoxy groups, aryl groups, a carboxyl group, $C_{1-6}$ alkoxy-carbonyl groups, aralkyloxycarbonyl groups, halogen atoms and —CONR⁵R⁶ groups in which $R^5$ and $R^6$ are same or different from each other and represent a hydrogen atom, or an optionally substituted $C_{1-6}$ alkyl, optionally substituted $C_{1-6}$ alkoxy or hydroxyl group, or $R^5$ and $R^6$ may be combined with each other and together with the nitrogen atom to which they are attached to form a ring. The substituted $C_{1-6}$ alkoxy group includes, for example, methoxymethoxy, (2-methoxyethoxy)methoxy, benzyloxy, carboxymethoxy, methoxycarbonylmethoxy, ethoxycarbonylmethoxy, isopropoxycarbonylmethoxy, tert-butoxycarbonylmethoxy, 1-(ethoxycarbonyl)isopropoxy, 3-(ethoxycarbonyl)propoxy, benzyloxycarbonylmethoxy, trifluoromethoxy, (methylcarbamoyl)methoxy, (dimethylcarbamoyl)methoxy, (3-pyridylmethylcarbamoyl) methoxy, (ethylcarbamoyl)methoxy, (diethylcarbamoyl) methoxy, (hexylcarbamoyl)methoxy, (2-methoxyethyl) carbamoylmethoxy, (2-benzylthioethyl)carbamoylmethoxy, (propylcarbamoyl)methoxy, (isopropylcarbamoyl)methoxy, (methylmethoxycarbamoyl)methoxy, (ethoxycarbonylmethylcarbamoyl)methoxy, (cyclopentylcarbamoyl)methoxy, and morpholinocarbonylmethoxy groups.

When two or more optionally substituted $C_{1-6}$ alkoxy or alkyl groups are present on the phenyl group represented by $Ar^2$ as the substituents, these two groups may be combined through the alkyl moiety to form an alkylene group, such as tetramethylene or trimethylene group, or an alkylenedioxy group, such as methylenedioxy group. Further, these alkylene or alkylenedioxy groups may be substituted by any suitable substituent, for example, a $C_{1-6}$ alkoxy-carbonyl group, such as an ethoxycarbonyl group.

The amino group as a substituent on the phenyl group represented by $Ar^2$ and the amino group represented by $R^4$ in the aforementioned formula —O—CO—R⁴ may be substituted by any suitable substituent(s), for example, at least one selected from optionally substituted $C_{1-6}$ alkyl groups and optionally substituted $C_{1-6}$ alkoxy groups, and may be cyclic. The substituted amino group includes, for example, methylamino, dimethylamino, 3-pyridylmethylamino, ethylamino, diethylamino, (2-methoxyethyl)amino, (2-benzylthioethyl)amino, propylamino, isopropylamino, cyclopentylamino, hexylamino, ethoxycarbonylmethylamino, methylmethoxyamino, hydroxyamino, and morpholino groups.

The alkylene group represented by M is an alkylene group having 2 to 4 chain members, i.e., 2 to 4 carbon atoms constituting the alkylene chain, and these alkylene groups may have 1 to 4 side chains each having 1 to 3 carbon atoms, such as methyl, ethyl or propyl group.

Among the compounds represented by the aforementioned formula (I), the compounds other than those wherein $Ar^1$ is 3-pyridyl group, $Ar^2$ is 3,5-di-tert-butyl-4-hydroxyphenyl group, $R^1$, $R^2$ and $R^3$ are all hydrogen atom, X is oxygen atom, A and B are hydrogen atom, and n is 1, are novel.

The pharmaceutically acceptable salts of the compounds represented by the aforementioned formula (I) or (I') include, for example, inorganic acid salts, such as hydrochlorides, sulfates, hydrobromides, nitrates and phosphates, and organic acid salts, such as trifluoroacetates, tartrates, citrates, malates, maleates, fumarates, methanesulfonates, benzenesulfonates, and toluenesulfonates. Some compounds may form hydrates and they are encompassed within the scope of the present invention.

The compounds represented by the aforementioned formula (I) or (I') may be present in the form of stereoisomers, such as cis and trans, as can be seen from their chemical structural formulae. Of course, these stereoisomers will be encompassed within the scope of the present invention.

The compounds represented by the aforementioned formula (I) may be prepared in various manners. Typical examples of the methods includes those shown in the following (1) to (8).

(1) When in the formula (I), $R^2$ is a hydrogen atom or a $C_{1-6}$ alkyl group, and X is an oxygen atom, the compounds (I) can be prepared by reacting a carboxylic acid represented by the general formula (II):

(II)

wherein $Ar^1$, $R^1$ and $R^2$ are as defined above, or a reactive derivative thereof, with an amine represented by the general formula (III):

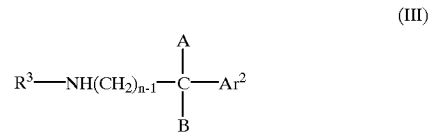

(III)

wherein $Ar^2$, $R^3$, A, B and n are as defined above, to effect amidization.

The starting materials, pyridylacrylic acid derivatives (II) and the amine compounds (III) may be commercially available, or obtained by any general methods.

This reaction is preferably carried out in the presence of a condensing agent, such as dicyclohexylcarbodiimide, N,N'-carbonyldiimidazole, 1-hydroxybenzotriazole, N-hydroxysuccinimide, diethylphosphoric acid cyanide, diphenylphosphoric acid azide, in particular if the compound (II) in the form of a carboxylic acid is reacted. More particularly, the combined use of the aforementioned diethylphosphoric acid cyanide with triethylamine is advantageous. The reactive derivatives of the compound (II) include acid anhydrides and mixed acid hydrides.

This reaction is preferably carried out in a suitable solvent which is not involved in the reaction, for example an organic solvent, such as tetrahydrofuran, N,N-dimethylformamide and dichloromethane, in particular under anhydrous conditions. The reaction temperature is not particularly limited but may usually be ice-cooled to approximately room temperature. The reaction period of time is typically 0.5 to 20 hours. After the reaction is completed, a desired material may be isolated in any conventional manner.

(2) When in the formula (I), $R^2$ is a cyano or $C_{1-6}$ alkoxy-carbonyl group, and X is an oxygen atom, the compounds (I) can be prepared by subjecting a nicotinaldehyde derivative represented by the general formula (IV):

$$Ar^1—CHO \quad (IV)$$

wherein $Ar^1$ is as defined above, and an active methylene compound represented by the general formula (V):

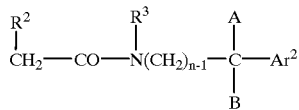

wherein $R^2$ is a cyano or $C_{1-6}$ alkoxy-carbonyl group, and $Ar^2$, $R^3$, A, B and n are as defined above, to Knoevenagel condensation reaction in the presence of a basic catalyst.

The starting materials, nicotinaldehyde derivative (IV) and active methylene compound (V), may be commercially available or obtained by a conventional method.

This reaction may be carried out in a suitable solvent which is not involved in the reaction, for example, an organic solvent, such as benzene, toluene or ethanol. The basic catalyst may be pyridine, piperidine or the like. The reaction temperature is 80 to 140° C. After the reaction is over, a desired substance may be isolated in a conventional manner.

(3) When X is a sulfur atom in the formula (I), the compound (I) may be prepared through thionization by reacting the compound obtained in the method (1) above, i.e., an amide represented by the general formula (VI):

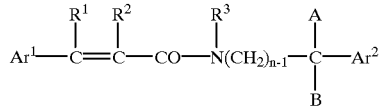

wherein $Ar^1$, $Ar^2$, $R^1$, $R^2$, $R^3$, A, B and n are as defined above, with a sulfurizing agent such as Lawesson reagent.

The solvent used in this reaction is a solvent which is not involved in the reaction, such as toluene or xylene. The reaction temperature is usually 110 to 140° C. After the completion of the reaction, a desired compound may be isolated in a conventional manner.

(4) The compounds of the formula (I) wherein X is an oxygen atom and the phenyl group represented by $Ar^2$ is substituted by at least one selected from $—OC(R^7)_2COR^8$ groups in which $R^7$ is a hydrogen atom or a methyl group and $R^8$ is a hydroxyl, $C_{1-6}$ alkoxy or optionally substituted amino group, and $—O—CO—R^4$ groups in which $R^4$ is as defined above, may be prepared by introducing the $—OC(R^7)_2COR^8$ or $—O—CO—R^4$ group into the hydroxyl group of the compounds obtained in the aforementioned method (1) and (2) wherein the phenyl group represented by $Ar^2$ is substituted by at least one hydroxyl group, according to any conventional manner for alkylating or acylating the hydroxyl group.

(5) The compounds of the formula (I) wherein A and B together represent an oxo group can also be prepared by preparing an alcohol compound of the formula (I) wherein A is a hydrogen atom and B is a hydroxyl group by the aforementioned method (1), (3) or (4) followed by oxidizing by an oxidizing agent such as pyridinium dichromate (PDC).

(6) The compounds of the formula (I) wherein A and B together represent a group represented by the following formula: $=N—Y$ in which Y is a di($C_{1-6}$ alkyl)amino, hydroxyl, aralkyloxy or $C_{1-6}$ alkoxy group can also be prepared by obtaining a compound of the formula (I) wherein A and B together represent an oxo group by the aforementioned method (1), (2), (4) or (5) followed by condensing with an amine represented by the following formula: $H_2N—Y$ in which Y is as defined above in a conventional manner.

(7) The compounds of the formula (I) wherein A and B together represent a group represented by the following formula: $—Z^1—M—Z^2—$ in which $Z^1$ and $Z^2$ are same or different and independently represent an oxygen or sulfur atom or imino group optionally substituted by $C_{1-6}$ alkyl group and M is an alkylene group having 2 to 4 chain members or a 1,2-phenylene group can also be prepared by condensing a compound of the formula (I) wherein A and B together represent an oxo group with a bifunctional compound represented by the following formula: $H—Z^1—M—Z^2—H$ in which $Z^1$, $Z^2$ and M are as defined above according to conventional methods.

For example, a compound of the formula (I) wherein A and B together represent an oxo group can be treated with ethylene glycol in the presence of p-toluenesulfonic acid in benzene to prepare a ketal form of the formula (I) wherein A and B together represent an ethylenedioxy group.

Also, a compound of the formula (I) wherein A and B together represent an oxo group can be treated with 1,2-ethanedithiol in chloroform in the presence of boron trifluoride-diethylether complex to prepare a thioketal form of the formula (I) wherein A and B together represent an ethylenedithio group.

(8) The compounds of the formula (I) wherein A is a hydroxyl group and B is a 1-$C_{1-6}$ alkyl-imidazol-2-yl group can be prepared by treating a compound of the formula (I) wherein A and B together represent an oxo group with 1-$C_{1-6}$ alkyl-imidazole in a conventional manner.

Resulting products may be purified by any procedures conventionally used, for example, column chromatography using such a carrier as silica gel or recrystallization using ethyl acetate, acetone, hexane, methanol, ethanol, chloroform, dimethylsulfoxide, water etc. Eluting solvents for the column chromatography include chloroform, methanol, acetone, hexane, dichloromethane, ethyl acetate and mixed solvents thereof.

The compounds represented by the aforementioned formula (I) and pharmaceutically acceptable salts thereof, hereinafter referred to "pyridylacrylamide derivatives (I)", are useful as agents for treating nephritis. Further, they have TGF-β inhibiting activity and are useful as agents for treating TGF-β-involving diseases, for example, such diseases as liver cirrhosis, pulmonary or other fibrosis, nephritis, chronic renal insufficiency, diabetic nephropathy, and retinopathy.

Dose amounts and formulation of the pyridylacrylamide derivatives (I) are described below.

The pyridylacrylamide derivative (I) may be administered as such or in combination with conventional formulation carriers to animals and humans. Dosage forms are not particularly limited and may be appropriately selected depending upon needs. They include oral formulations, such as tablets, capsules, granules, fine granules and powders, and parenteral formulations, such as injections and suppositories.

To have the oral formulations exhibit desired effects, the pyridylacrylamide derivative (I) may be generally administered to an adult in several times a day in a daily amount of 0.1 mg to 2 g although it may vary with the age, body weight and degree of disease of a patient.

Oral formulations may be prepared in a conventional manner using e.g. starch, lactose, sucrose, mannitol, carboxymethylcellulose, corn starch, and/or inorganic salts.

In addition to the aforementioned excipients, such formulations can also contain binders, disintegrators, surfactants, lubricants, enhancers for the fluidity, flavoring agents, colorants and perfumes, if necessary. Examples thereof are illustrated below.

Binders

Starch, dextrin, powdered acacia, gelatin, hydroxypropyl starch, methylcellulose, carboxymethylcellulose sodium, hydroxypropylcellulose, micro crystalline cellulose, ethylcellulose, polyvinylpyrrolidone, Macrogol.

Disintegrators

Starch, hydroxypropyl starch, carboxymethylcellulose sodium, carboxymethylcellulose calcium, carboxymethylcellulose, low-substituted hydroxypropylcellulose.

Surfactants

Sodium lauryl sulfate, soybean lecithin, sucrose esters of fatty acid, Polysorbate 80.

Lubricants

Talc, waxes, hydrogenated vegetable oils, sucrose esters of fatty acid, magnesium stearate calcium stearate, aluminum stearate, and polyethylene glycol.

Enhancers for the fluidity

Light anhydrous silicic acid, dried aluminum hydroxide gel, synthetic aluminum silicate, magnesium silicate.

The pyridylacrylamide derivative (I) may also be administered in the form of suspensions, emulsions, syrups and elixirs. These dosage forms may contain corrigents and colorants.

To have the parenteral formulations exhibit desired effects, intravenous injection or drip infusion, or subcutaneous or intramuscular injection of a daily dose amount of 0.01 to 600 mg of the pyridylacrylamide derivative (I) may be generally suitable to an adult although it may vary with the age, body weight and degree of disease of a patient.

These parenteral formulations may be prepared in any conventional manners. Generally, diluents, such as distilled water for injection, physiological saline, aqueous glucose solution, vegetable oils for injection, sesame oil, peanut oil, soybean oil, corn oil, propylene glycol and polyethylene glycol, may be used. If necessary, disinfectants, antiseptics and/or stabilizers may be added. In view of stability, the parenteral formulations may also be filled into a vial or the like, refrigerated, dehydrated by conventional freeze-drying techniques, and reconstituted from the freeze-dried product into a liquid immediately prior to use. Further, isotonicities, stabilizers, antiseptics and/or soothing agents may be added if necessary.

Other parenteral formulations include paints such as external liquid preparations and ointments, and suppositories for intrarectal administration and may be prepared in any conventional manners.

BEST MODE FOR CARRYING OUT THE INVENTION

Hereinafter, the present invention will be described in more detail by way of examples but the scope of the present invention is not limited thereto.

EXAMPLE 1

Synthesis of (E)-2-cyano-N-(4-methoxymethoxyphenethyl)-3-(3-pyridyl)-2-propenoic acid amide (Compound 1)

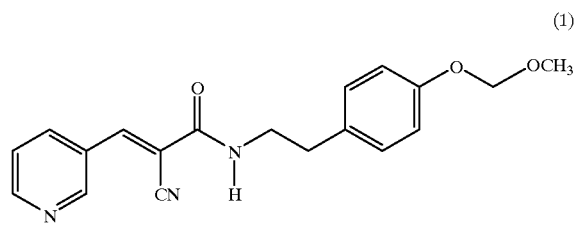

(1)

4-Methoxymethoxyphenethylamine (1.58 g, 8.7 mmol) and cyanoacetic acid (0.82 g, 9.6 mmol) were dissolved in dimethylformamide (10 ml) and under ice-cooling and stirring diethylphosphoric cyanide (1.51 ml, 9.6 mmol) and triethylamine (1.34 ml, 9.6 mmol) were sequentially added. After stirring at room temperature for 24 hours, saturated aqueous sodium bicarbonate solution was added to the reaction mixture, extracted with ethyl acetate, washed with water and dried over magnesium sulfate. The solvent was distilled out under reduced pressure and the residue was purified by silica gel column chromatography (chloroform:methanol=19:1) to yield 2-cyano-N-(4-methoxymethoxyphenethyl)acetamide (0.97 g, 45%).

Properties: solid $^1$H-NMR (CDCl$_3$) δ: 2.80 (2H, t, J=7 Hz), 3.32 (2H, s), 3.48 (3H, s), 3.53 (2H, td, J=7, 6 Hz), 5.16 (2H, s), 6.11 (1H, br), 7.00 (2H, br d, J=9 Hz), 7.12 (2H, br d, J=9 Hz)

Then, ethanol (10 ml), 3-pyridinecarbaldehyde (0.62 g, 5.8 mmol) and a drop of piperidine were added to the resulting 2-cyano-N-(4-methoxymethoxyphenethyl) acetamide (0.96 g, 3,87 mmol) and refluxed under heating for 19 hours. The reaction mixture was concentrated under reduced pressure and the residue was purified by silica gel column chromatography (chloroform:methanol=19:1) and recrystallized to yield the titled compound (0.83 g, 64%). Properties: mp 105–106° C. (ethyl acetate-hexane)

$^1$H-NMR (CDCl$_3$) δ: 2.87 (2H, t, J=7 Hz), 3.48 (3H, s), 3.66 (2H, td, J=7, 6 Hz), 5.17 (2H, s), 6.42 (1H, br), 7.02 (2H, br d, J=9 Hz), 7.16 (2H, br d, J=9 Hz), 7.45 (1H, dd, J=8, 5 Hz), 8.33 (1H, s), 8.41 (1H, ddd, J=8, 2, 2 Hz), 8.73 (1H, dd, J=5, 2 Hz), 8.94 (1H, d, J=2 Hz)

EXAMPLES 2 to 5

Compounds 2 to 5 were obtained according to the method similar to that of Example 1.

EXAMPLE 2

(2)

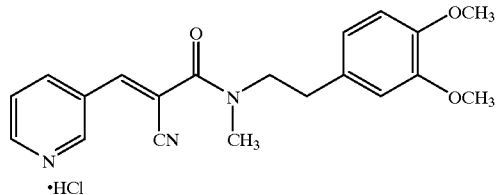

Compound 2

•HCl

Properties: mp 115–120° C. (ethanol-ether)

$^1$H-NMR (DMSO-d$_6$, 100° C.) δ: 2.87 (2H, t, J=7 Hz), 3.07 (3H, s), 3.71 (2H, t, J=7 Hz), 3.73 (6H, s), 6.73–6.89 (3H, m), 7.52 (1H, s), 7.60 (1H, dd, J=8, 5 Hz), 8.29 (1H, d, J=8 Hz), 8.71 (1H, d, J=5 Hz), 8.92 (1H, d, J=2 Hz)

EXAMPLE 3

(3)

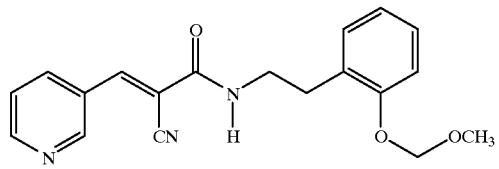

Compound 3

Properties: mp 109–110° C. (ethyl acetate-hexane)

$^1$H-NMR (CDCl$_3$) δ: 2.98 (2H, t, J=7 Hz), 3.51 (3H, S), 3.69 (2H, td, J=7, 5 Hz), 5.30 (2H, s), 6.73 (1H, br), 6.95–7.28 (4H, m), 7.45 (1H, dd, J=8, 5 Hz), 8.32 (1H, S), 8.41 (1H, d, J=8 Hz), 8.73 (1H, dd, J=5, 2 Hz), 8.93 (1H, d, J=2 Hz)

EXAMPLE 4

(4)

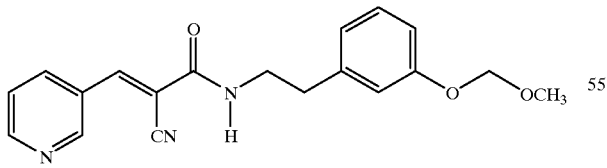

Compound 4

Properties: mp 101–102° C.

$^1$H-NMR (CDCl$_3$) δ: 2.90 (2H, t, J=7 Hz), 3.48 (3H, s), 3.69 (2H, td, J=7, 6 Hz), 5.19 (2H, s), 6.44 (1H, br), 6.86–7.00 (3H, m), 7.22–7.31 (1H, m), 7.45 (1H, dd, J=8, 5 Hz), 8.34 (1H, s), 8.41 (1H, d, J=8 Hz), 8.73 (1H, dd, J=5, 2 Hz), 8.94 (1H, d, J=2 Hz)

EXAMPLE 5

(5)

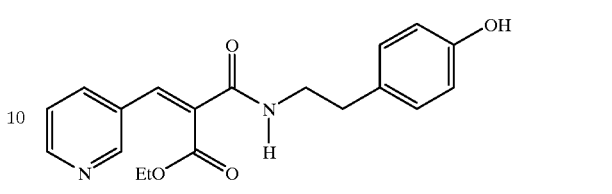

Compound 5

Properties: mp 134–135° C. (ethanol-ethyl acetate)

$^1$H-NMR (CDCl$_3$) δ: 1.34 (3H, t, J=7 Hz), 2.72 (2H, t, J=7 Hz), 3.59 (2H, td, J=7, 6Hz), 4.30 (2H, q, J=7 Hz), 6.24 (1H, t, J=6 Hz), 6.68 (2H, d, J=8 Hz), 6.88 (2H, d, J=8 Hz), 7.04 (1H, br s), 7.27–7.33 (1H, m), 7.63 (1H,s), 7.88 (1H, d, J=8Hz), 8.55 (2H, m)

EXAMPLE 6

Synthesis of (E)-2-cyano-N-(4-hydroxyphenethyl)-3-(3-pyridyl)-2-propenoic acid amide hydrochloride (Compound 6)

(6)

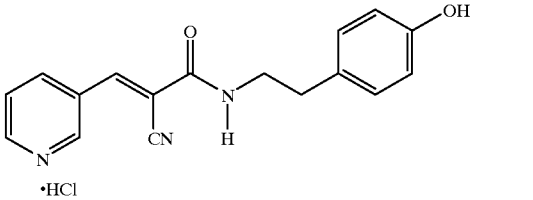

•HCl (E)-2-cyano-N-(4-methoxymethoxyphenethyl)-3-(3-pyridyl)-2-propenoic acid amide (0.81 g, 2.4 mmol) obtained in Example 1 was dissolved in a mixed solution of methanol (10 ml) and ethanol (10 ml) and concentrated hydrochloric acid (0.3 ml) was added and stirred for 3 days. The precipitated crystal was filtered and washed with ether to yield the titled compound (0.57 g, 72%).

Properties: mp 169–174° C.

$^1$H-NMR (CDCl$_3$)δ: 2.72 (2H, t, J=7 Hz), 3.35–3.41 (2H, m), 6.70 (2H, d, J=8 Hz), 7.03 (2H, d, J=8 Hz), 7.87 (1H, dd, J=8, 5 Hz), 8.33 (1H, s), 8.64 (1H, d, J=8 Hz), 8.74 (1H, t, J=6 Hz), 8.86 (1H, d, J=5 Hz), 9.12 (1H, s)

EXAMPLES 7 and 8

Compounds 7 and 8 were obtained according to the method similar to that of Example 6.

EXAMPLE 7

(7)

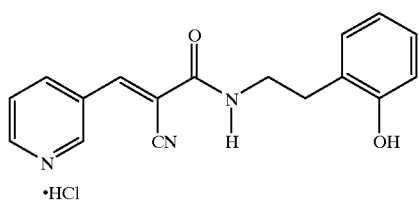

Compound 7

Properties: mp 111–116° C. (methanol)

$^1$H-NMR (DMSO-$d_6$) δ: 2.79 (2H, t, J=7 Hz), 3.39–3.48 (2H, m), 6.69–7.10 (4H, m), 7.85(1H, dd, J=8, 5 Hz), 8.30 (1H, s), 8.62 (1H, d, J=8 Hz), 8.72(1H, br t), 8.85 (1H, d, J=5 Hz), 9.11 (1H, s)

EXAMPLE 8

Compound 8

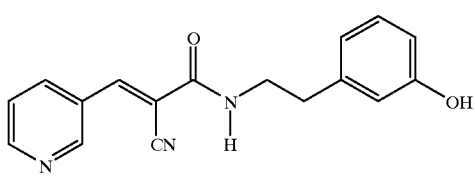

(8)

Properties: mp 173–175° C. (ethanol)

$^1$H-NMR (DMSO-$d_6$) δ: 2.74 (2H, t, J=7 Hz), 3.39 (2H, td, J=7, 6 Hz), 6.59–6.67 (3H, m), 7.10 (1H, t, J=8 Hz), 7.62 (1H, dd, J=8, 5 Hz), 8.21 (1H, s), 8.38 (1H, d, J=8 Hz), 8.62 (1H, t, J=6 Hz), 8.73 (1H, dd, J=5, 1 Hz), 8.99 (1H, d, J=2 Hz), 9.30 (1H, s)

EXAMPLE 9

Synthesis of (E)-N-methyl-3-(3-pyridyl)-N-(3,4,5-trimethoxyphenethyl)-2-propenoic acid amide hydrochloride (Compound 9)

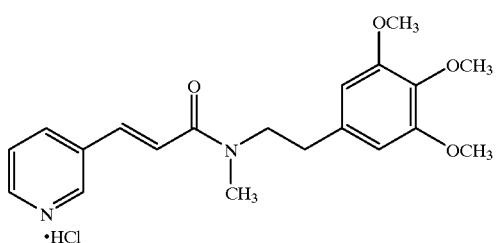

(9)

A mixture of 3,4,5-trimethoxybenzaldehyde (9.80 g, 50 mmol), nitromethane (18 ml), ammonium acetate (4.11 g) and acetic acid (38 ml) was heated and refluxed for 2 hours. After the reaction mixture was concentrated under reduced pressure, 10% aqueous sodium hydroxide solution was added to the residue and the reaction mixture was extracted with dichloromethane, washed with water and dried over anhydrous magnesium sulfate. The solvent was distilled out under reduced pressure and the residue was purified by silica gel chromatography (dichloromethane) and recrystallized to yield trans-3,4,5-trimethoxy-β-nitrostyrene (4.96 g, 41%). Properties: mp 116–118° C. (ethanol)

$^1$H-NMR (CDCl$_3$) δ: 3.91 (6H, s), 3.92 (3H, s), 6.77 (2H, s), 7.54 (1H, d, J=13.6 Hz), 7.94 (1H, d, J=13.6 Hz)

A solution of trans-3,4,5-trimethoxy-β-nitrostyrene (4.78 g, 20 mmol) in tetrahydrofuran (20 ml) was dropwise added to a suspension of lithium aluminum hydride (1.52 g) in tetrahydrofuran (20 ml) under ice-cooling and stirring. After stirring at room temperature for 3 hours, water (1.5 ml), 15% aqueous sodium hydroxide solution (1.5 ml), and water (4.5 ml) were sequentially added dropwise to the reaction mixture under ice-cooling and stirring. A small amount of potassium carbonate was added and stirred for a few minutes. Inorganic salts were filtered out and washed with tetrahydrofuran, and the filtrate was concentrated under reduced pressure. The residue was dissolved in 2N hydrochloric acid and washed with dichloromethane. The aqueous layer was made basic with sodium hydroxide and the released oil material was extracted with dichloromethane. After washed with water, the extract was dried over potassium carbonate and the solvent was distilled out under reduced pressure to yield a crude oil of 3,4,5-trimethoxyphenethyl-amine.

A solution of the crude oil of 3,4,5-trimethoxyphenethylamine in tetrahydrofuran (30 ml) was added to a mixed acid anhydride of acetic acid and formic acid, which had been synthesized by adding 98% formic acid (6.2 ml) to acetic anhydride (12.5 ml) under ice-cooling and reacting at 60° C. for 3 hours, under room temperature and stirred for 17 hours. The reaction mixture was concentrated under reduced pressure and tetrahydrofuran (40 ml) and borane-methyl sulfide complex (12 ml) were added to the residue under ice-cooling and stirring. The reaction mixture was heated and refluxed for 17 hours. After the reaction mixture was cooled, methanol was added to stop the reaction and concentrated under reduced pressure. A hydrogen chloride-methanol solution was added to the residue and heated and refluxed for 3 hours. The solvent was distilled out under reduced pressure and the residue was dissolved in 2N hydrochloric acid and washed with dichloromethane. The aqueous layer was made basic with sodium hydroxide and the released oil material was extracted with dichloromethane. After washed with water and dried over potassium carbonate, the solvent was distilled out under reduced pressure to yield N-methyl-3,4,5-trimethoxyphenethylamine (1.61 g) as a colorless oil.

$^1$H-NMR (CDCl$_3$) δ: 2.47 (3H, s), 2.68–2.91 (4H, m), 3.82 (3H, s), 3.86 (6H, s), 6.41(2H, s)

N-Methyl-3,4,5-trimethoxyphenethylamine (1.60 g, 7.11 mmol) and trans-3-(3-pyridyl)acrylic acid (1.17 g) were dissolved in dimethylformamide (8 ml), and diethylphosphoric cyanide (1.3 ml) and triethylamine (2.2 ml) were sequentially added under ice-cooling and stirring and stirred at room temperature for 1 hour. Saturated aqueous sodium bicarbonate solution was added to the reaction mixture, and the reaction mixture was extracted with dichloromethane, washed with water and dried over potassium carbonate. The solvent was distilled out under reduced pressure and the residue was purified by silica gel column chromatography (ethyl acetate:hexane=10:1) to yield amorphous (E)-N-methyl-3-(3-pyridyl)-N-(3,4,5-trimethoxyphenethyl)-2-propenoic acid amide (2.37 g, 94%). Then, hydrogen chloride-methanol was added to the product (1.80 g) to produce its hydrochloride, which was recrystallized in a mixed solvent of ethyl acetate-methanol to yield the titled compound (1.59 g, 57%).

Properties: mp 164–171° C. (ethyl acetate-methanol)

$^1$H-NMR (DMSO-$d_6$, 150° C.) δ: 3.04 (2H, t, J=7.1 Hz), 3.25 (3H, s), 3.87 (3H, s), 3.94 (2H, t, J=7.1 Hz), 3.99 (6H, s), 6.75 (2H, s), 7.24 (1H, d, J=15.6 Hz), 7.59 (1H, d, J=15.6 Hz), 7.67–7.71 (1H, m), 8.24–8.28 (1H, m),8.76–8.78 (1H, m), 8.99 (1H, br s)

EXAMPLES 10 to 64

Compounds 10 to 64 were obtained according to the method similar to that of Example 9.

EXAMPLE 10

Compound 10

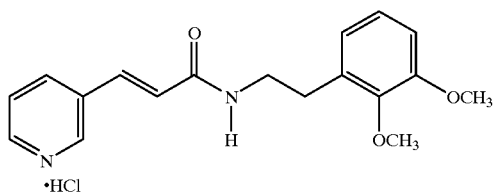

Properties: mp 150–155° C. (ethanol)

$^1$H-NMR (DMSO-$d_6$) δ: 2.78 (2H, t, J=7.4 Hz), 3.35–3.45 (2H, m), 3.74 (3H, s), 3.79 (3H, s), 6.77–6.82 (1H, m), 6.88–6.94 (1H, m), 6.92 (1H, d, J=15.9 Hz), 6.96–7.04 (1H, m), 7.58 (1H,d,J=15.9 Hz), 7.97–8.05 (1H, m), 8.49 (1H, t, J=5.7 Hz), 8.62–8.67 (1H, m), 8.82–8.86 (1H, m), 9.09 (1H, br s)

EXAMPLE 11

Compound 11

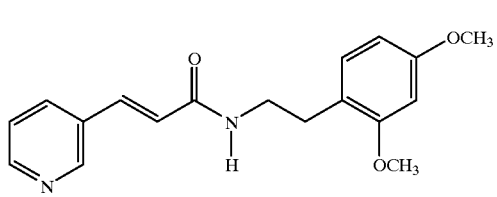

Properties: mp 135.5–136.5° C. (ethyl acetate-hexane)

$^1$H-NMR (DMSO-$d_6$) δ: 2.68 (2H, t, J=7.7 Hz), 3.29–3.38 (2H, m), 3.73 (3H, s), 3.78 (3H, s), 6.45 (1H, dd, J=8.2,2.3 Hz), 6.54 (1H, d, J=2.3 Hz), 6.71 (1H, d, J=15.9 Hz), 7.03 (1H, d, J=8.2 Hz), 7.41–7.49 (1H, m), 7.45 (1H, d, J=15.9 Hz), 7.94–8.00 (1H, m), 8.19 (1H, t, J=5.6 Hz), 8.53–8.56 (1H, m), 8.74 (1H, br s)

EXAMPLE 12

Compound 12

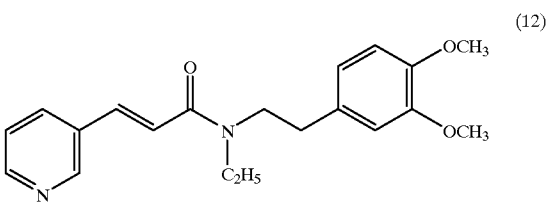

Properties: oil $^1$H-NMR (DMSO-$d_6$, 100° C.) δ: 1.13 (3H, t, J =7.3 Hz), 2.80 (2H, t, J=7.3 Hz), 3.45 (2H, q, J=7.3 Hz), 3.63 (2H, t, J=7.3 Hz), 3.70 (3H, s), 3.74 (3H, s), 6.75(1H, dd, J=8.3, 2.0 Hz), 6.82 (1H, d, J=2.0 Hz), 6.83 (1H, d, J=8.3 Hz), 6.96 (1H, d, J=15.6 Hz), 7.32–7.36 (1H, m), 7.38 (1H, d, J=15.6 Hz), 7.89–7.92 (1H, m), 8.48–8.51 (1H, m), 8.71(1H, br s)

EXAMPLE 13

Compound 13

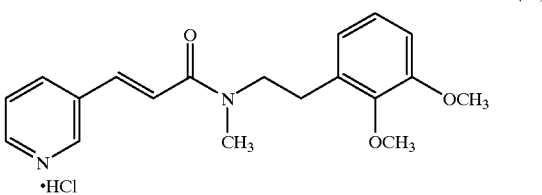

Properties: mp 160–163° C. (ethanol)

$^1$H-NMR (DMSO-$d_6$, 120° C.) δ: 2.85 (2H, t, J=7.2 Hz), 3.01 (3H, s), 3.61–3.69 (2H, m), 3.75 (3H, s), 3.77 (3H, s), 6.78 (1H, dd, J=7.1, 2.0 Hz), 6.85 (1H, dd, J=8.0, 2.0 Hz), 6.93 (1H, dd, J=8.0, 7.1 Hz), 7.10 (1H, d, J=15.6 Hz), 7.39 (1H, d, J=15.6 Hz), 7.54–7.61 (1H, m), 8.19 (1H, d, J=7.4 Hz), 8.59 (1H, d, J=4.8 Hz),8.83 (1H, s)

EXAMPLE 14

Compound 14

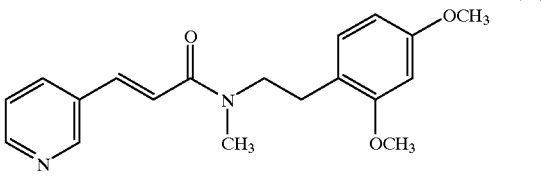

Properties: mp 84–88° C. (ethyl acetate-hexane)

$^1$H-NMR (DMSO-$d_6$, 100° C.) δ: 2.76 (2H, t, J=7.3 Hz), 2.96 (3H, s), 3.59 (2H, t,J=7.3 Hz), 3.68 (3H, s), 3.76(3H, s), 6.39–6.47 (2H, m), 6.93–7.05 (2H, m),7.28–7.41 (2H, m), 7.88–7.98 (1H, m), 8.50–8.52 (1H, m), 8.72 (1H, br s)

EXAMPLE 15

Compound 15

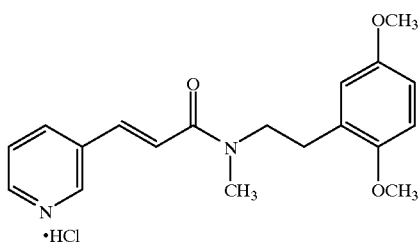
(15)

Properties: mp 153–156° C. (ethanol)

¹H-NMR (DMSO-d₆, 120° C.) δ: 2.82 (2H, t, J=7.1 Hz), 2.99 (3H, s) 3.65 (2H, t, J=7.1 Hz), 3.66 (3H, s), 3.75 (3H, s), 6.69 (1H, dd, J=8.7, 2.9 Hz), 6.75 (1H, d, J=2.9 Hz), 6.83 (1H, d, J=8.7 Hz), 7.08 (1H, d, J=15.6 Hz), 7.37 (1H, d, J=15.6 Hz), 7.59 (1H, dd, J=7.9, 5.1 Hz), 8.19 (1H, d, J=7.9 Hz), 8.59 (1H, d, J=5.1 Hz), 8.83 (1H, s)

EXAMPLE 16

Compound 16

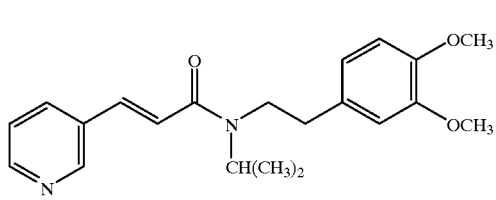
(16)

Properties: oil

¹H-NMR (DMSO-d₆, 100° C.) δ: 1.20 (6H, d, J=6.7 Hz), 2.80 (2H, t, J=7.3 Hz). 3.52 (2H, t, J=7.3 Hz), 3.70 (3H, s), 3.75 (3H, s), 4.45 (1H, septet, J=6.7 Hz), 6.74–6.87 (3H, m), 7.07 (1H, d, J=15.6 Hz), 7.33–7.40 (1H, m), 7.42 (1H, d, J=15.6 Hz), 7.95–7.99 (1H, m), 8.49–8.53 (1H, m), 8.76 (1H, m)

EXAMPLE 17

Compound 17

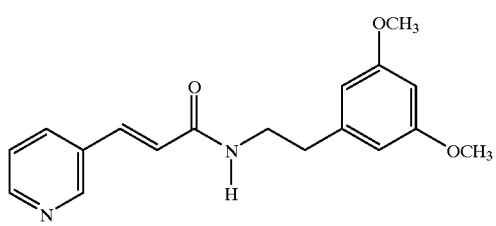
(17)

Properties: oil

¹H-NMR (CDCl₃) δ: 2.84 (2H, t, J=6.9 Hz), 3.61–3.71 (2H, m), 3.78 (6H, s), 6.13 (1H, br s), 6.34–6.39 (3H, m), 6.44 (1H, d, J=15.7 Hz), 7.28 (1H, dd, J=7.9, 4.8 Hz), 7.60 (1H, d, J=15.7 Hz), 7.75 (1H, d, J=7.9 Hz), 8.53 (1H, d, J=4.8 Hz), 8.68 (1H, br s)

EXAMPLE 18

Compound 18

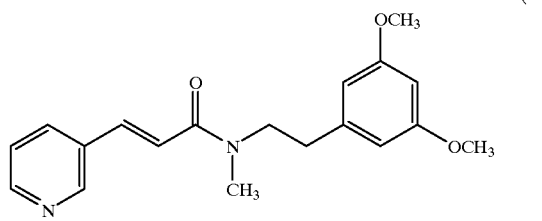
(18)

Properties: oil

¹H-NMR (DMSO-d₆, 100° C.) δ: 2.79 (2H, t, J=7.3 Hz), 2.97 (3H, s), 3.65–3.73 (2H, m), 3.69 (6H, s), 6.29 (1H, d, J=2.4 Hz), 6.40 (2H, d, J=2.4 Hz), 7.04 (1H, br),7.29–7.40 (2H, m), 7.92–8.01 (1H, m), 8.50–8.52 (1H, m), 8.74 (1H, br s)

EXAMPLE 19

Compound 19

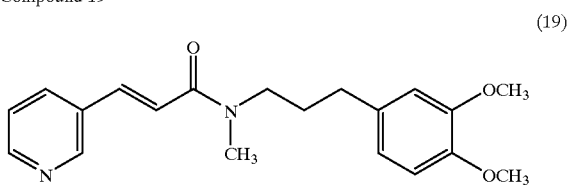
(19)

Properties: oil

¹H-NMR (DMSO-d₆, 100° C.) δ: 1.75–1.97 (2H, m), 2.50–2.55 (2H, m), 3.02 (3H, s), 3.46 (2H, t, J=7.2 Hz), 3.71 (3H, s), 3.73 (3H, s), 6.70–6.85 (3H, m), 7.09 (1H, d, J=15.7 Hz), 7.34–7.38 (1H, m), 7.44 (1H, d, J=15.7 Hz), 7.95–7.99 (1H, m), 8.50–8.52 (1H, m), 8.76 (1H, d, J=2.0 Hz)

EXAMPLE 20

Compound 20

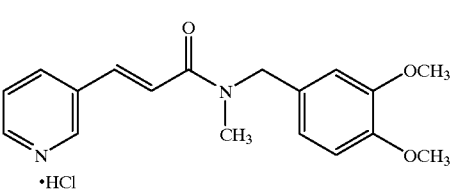
(20)

Properties: amorphous

¹H-NMR (DMSO-d₆, 100° C.) δ: 3.01 (3H, s), 3.74 (6H, s), 4.61 (2H, s), 6.65–6.94 (3H, m), 7.38 (1H, d, J=15.6 Hz), 7.57 (1H, d, J=15.6 Hz), 7.61–7.66 (1H, m), 8.33–8.37 (1H, m), 8.60–8.63 (1H, m), 8.95 (1H, br s)

EXAMPLE 21

Compound 21

(21)

·HCl

Properties: mp 182–186° C. (ether-methanol)

$^1$H-NMR (DMSO-d$_6$, 100° C.) δ: 1.27 (3H, t, J=6.9 Hz), 2.77 (2H, t, J=6.9 Hz), 2.99 (3H, s), 3.67–3.73 (5H, m), 3.94–4.03 (2H, m), 6.71–6.84 (3H, m), 7.04–7.14 (1H, m), 7.33–7.40 (1H, m), 7.56–7.66 (1H, m), 8.23–8.27 (1H, m), 8.65–8.67 (1H, m), 8.92 (1H, br s)

EXAMPLE 22

Compound 22

(22)

Properties: mp 152–154° C. (dichloromethane-hexane)

$^1$H-NMR (CDCl$_3$) δ: 2.78 (2H, t, J=6.7 Hz), 3.54–3.64 (2H, m), 3.87 (3H, s), 5.14 (2H, s), 5.64 (1H, m), 6.32 (1H, d, J=15.7 Hz), 6.75–6.88 (3H, m), 7.22–7.45 (6H, m), 7.59 (1H, d, J=15.7 Hz), 7.73–7.79 (1H, m), 8.56 (1H, dd, J=4.8,1.7 Hz), 8.70–8.71(1H, m)

EXAMPLE 23

Compound 23

(23)

Properties: mp 100–102° C. (ethyl acetate-hexane)

$^1$H-NMR (CDCl$_3$) δ: 4.64 (2H, d, J=6.0 Hz), 6.35 (1H, br t), 6.53 (1H, d, J=15.7 Hz), 7.27–7.81 (6H, m), 7.68 (1H, d, J=15.7 Hz), 8.55 (1H, dd, J=4.8,1.5 Hz), 8.74 (1H, d, J=1.8 Hz)

EXAMPLE 24

Compound 24

(24)

Properties: mp 134–135° C. (ethyl acetate-hexane)

$^1$H-NMR (CDCl$_3$) δ: 2.33 (3H, s), 2.86 (2H, t, J=6.9 Hz), 3.61–3.70 (2H, m), 5.79 (1H, br t), 6.39 (1H, d, J=15.7 Hz), 7.08–7.32 (5H, m), 7.60 (1H, d, J=15.7 Hz), 7.73–7.79 (1H, m), 8.53–8.72 (2H, m)

EXAMPLE 25

Compound 25

(25)

Properties: mp 112–114° C. (dichloromethane-hexane)

$^1$H-NMR (DMSO-d$_6$, 100° C.) δ: 2.87 (2H, t, J=7.0 Hz), 3.01 (3H, s), 3.71(2H, t, J=7.0 Hz), 7.13 (1H, d, J=15.5 Hz), 7.21 (1H, dd, J=8.2, 2.0 Hz), 7.31–7.49 (4H, m), 7.97–8.01 (1H, m), 8.50–8.53 (1H, m), 8.75–8.76 (1H, m)

EXAMPLE 26

Compound 26

(26)

Properties: mp 109–110° C. (ethyl acetate-hexane)

$^1$H-NMR (CDCl$_3$) δ: 2.88 (2H, t, J=6.9 Hz), 3.61–3.71 (2H, m), 5.88 (1H, br t),6.42 (1H, d, J=15.7 Hz), 7.08–7.33 (5H, m), 7.61 (1H, d, J=15.7 Hz), 7.74–7.80 (1H, m), 8.55 (1H, dd, J=4.8, 1.6 Hz), 8.71 (1H, d, J=2.1 Hz)

EXAMPLE 27

Compound 27

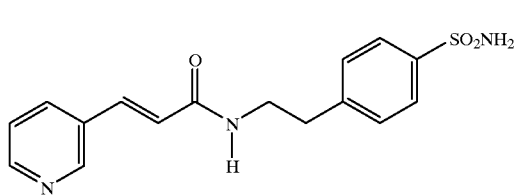
(27)

Properties: mp 226–231° C. (decomposition)

¹H-NMR (DMSO-d₆) δ: 2.87 (2H, t, J=7.0 Hz), 3.42–3.52 (2H, m), 6.71 (1H, d, J=15.9 Hz), 7.30–7.50 (5H, m), 7.76 (2H, d, J=8.2 Hz), 7.96–8.01 (1H, m), 8.29 (1H, br t), 8.53–8.75 (2H, m)

EXAMPLE 28

Compound 28

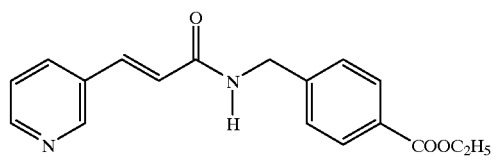
(28)

Properties: mp 140–141° C. (ethyl acetate-hexane)

¹H-NMR (CDCl₃) δ: 1.39 (3H, t, J=7.1 Hz), 4.36 (2H, q, J=7.1 Hz), 4.64 (2H, d, J=5.9 Hz), 6.42 (1H, br t), 6.52 (1H, d, J=15.7 Hz), 7.27–7.33 (1H, m), 7.39 (2H, d, J=8.4 Hz), 7.67 (1H, d, J=15.7 Hz), 7.74–7.80 (1H, m), 8.01 (2H, d, J=8.4 Hz), 8.55 (1H, dd, J=4.8, 1.6 Hz), 8.71 (1H, d, J=2.1 Hz)

EXAMPLE 29

Compound 29

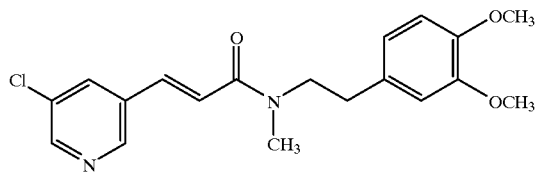
(29)

Properties: mp 138–140° C. (ethyl acetate-hexane)

¹H-NMR (DMSO-d₆, 150° C.) δ: 2.79 (2H, t, J=7.1 Hz), 2.99 (3H, s) 3.67 (2H, t, J=7.1 Hz), 3.69 (3H, s), 3.73 (3H, s), 6.70–6.84 (3H, m), 7.02 (1H, d, J=15.6 Hz), 7.29 (1H, d, J=15.6 Hz), 8.02 (1H, br s), 8.48 (1H, br s), 8.62 (1H, br s)

EXAMPLE 30

Compound 30

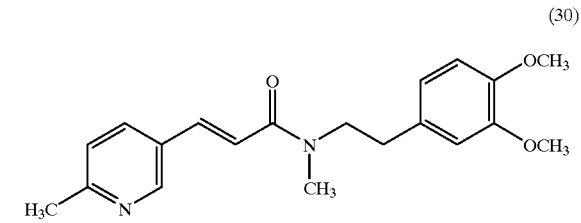
(30)

Properties: mp 124.5–125.5° C. (ethyl acetate-hexane)

¹H-NMR (DMSO-d₆, 150° C.) δ: 2.47 (3H, s), 2.79 (2H, t, J=7.2 Hz), 2.99 (3H, s), 3.66 (2H, t, J=7.2 Hz), 3.70 (3H, s), 3.74 (3H, s), 6.71–6.93 (4H, m), 7.19 (1H, d, J=8.1 Hz), 7.31 (1H, d, J=15.8 Hz), 7.77 (1H, d, J=8.1 Hz), 8.55 (1H, br s)

EXAMPLE 31

Compound 31

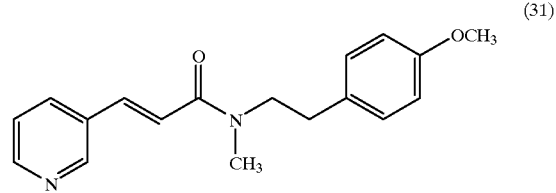
(31)

Properties: mp 81–84° C. (dichloromethane-hexane)

¹H-NMR (DMSO-d₆, 150° C.) δ: 2.80 (2H, t, J=7.2 Hz), 2.98 (3H, s), 3.64 (2H, t, J=7.2 Hz), 3.69 (3H, s), 6.81(2H, d, J=8.4 Hz), 6.95 (1H, d, J=15.6 Hz), 7.12 (2H, d, J=8.4 Hz), 7.33 (1H, d, J=15.6 Hz), 7.29–7.37 (1H, m), 7.88–7.93 (1H, m), 8.48–8.50 (1H, m), 8.69–8.70 (1H, m)

EXAMPLE 32

Compound 32

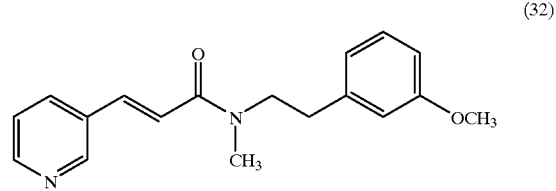
(32)

Properties: mp 81–84° C. (ethyl acetate-hexane)

¹H-NMR (DMSO-d₆, 100° C.) δ: 2.83(2H, t, J=7.3 Hz), 2.95(3H, s), 3.66–3.73 (2H, m), 3.71(3H, s), 6.70–6.82(3H, m), 6.98–7.20(2H, m), 7.32–7.40(2H, m), 7.94–7.98(1H, m), 8.49–8.52(1H, m), 8.73–8.74(1H, m)

EXAMPLE 33

Compound 33

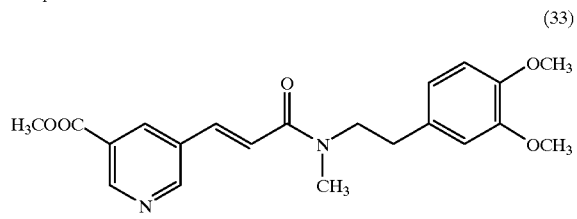
(33)

Properties: mp 165–167° C. (ethyl acetate-hexane)

$^1$H-NMR (DMSO-d$_6$, 150° C.) δ: 2.77–2.83 (2H, m), 3.00 (3H, s) 3.64–3.72 (2H, m), 3.68(3H, s), 3.73 (3H, s), 3.92 (3H, s), 6.71–6.84 (3H, m), 7.03 (1H, d, J=15.9 Hz), 7.37 (1H, d, J=15.9 Hz), 8.34 (1H, br s), 8.89 (1H, br s), 8.97 (1H, br s)

EXAMPLE 34

Compound 34

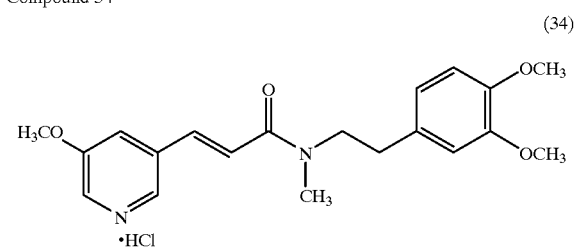
(34)

Properties: solid $^1$H-NMR (DMSO-d$_6$, 150° C.) δ: 2.79 (2H, t, J=7.2 Hz), 2.99 (3H, s), 3.67 (2H, t, J=7.2 Hz), 3.69 (3H, s), 3.73 (3H, s), 3.88 (3H, s), 6.71–6.84 (3H, m), 6.98 (1H, d, J=15.6 Hz), 7.32 (1H, d, J=15.6 Hz), 7.53 (1H, br s), 8.23–8.24 (1H, m), 8.32 (1H, br s)

EXAMPLE 35

Compound 35

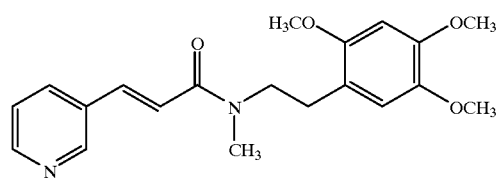
(35)

Properties: mp 71–74° C. (ethyl acetate-hexane)

$^1$H-NMR (DMSO-d$_6$, 100° C.) δ: 2.77 (2H, t, J=7.0 Hz), 2.98 (3H, s), 3.61 (2H, t, J=7.0 Hz), 3.68 (3H,S), 3.72 (3H, s), 3.74 (3H, s), 6.58 (1H, s), 6.74 (1H, s), 6.93 (1H, d, J=15.6 Hz), 7.28–7.36 (2H, m), 7.85–7.89 (1H, m), 8.48–8.50 (1H, m), 8.68 (1H, br s)

EXAMPLE 36

Compound 36

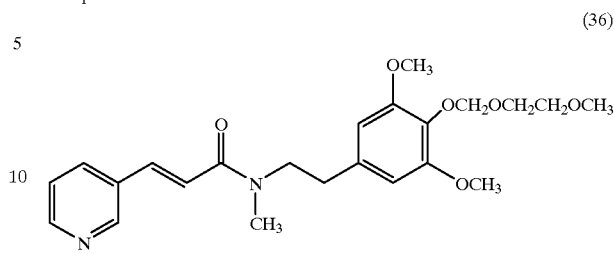
(36)

Properties: amorphous $^1$H-NMR (DMSO-d$_6$, 150° C.) δ: 2.78–2.85 (2H, m), 3.01 (3H, s) 3.25 (3H, s), 3.44–3.49 (2H, m), 3.63–3.81 (4H, m), 3.74 (6H, s), 4.96 (2H, s), 6.48–6.53 (2H, m), 6.94–7.02 (1H, m), 7.30–7.39 (2H, m), 7.87–7.91 (1H, m), 8.48–8.50 (1H, m), 8.70 (1H, br s)

EXAMPLE 37

Compound 37

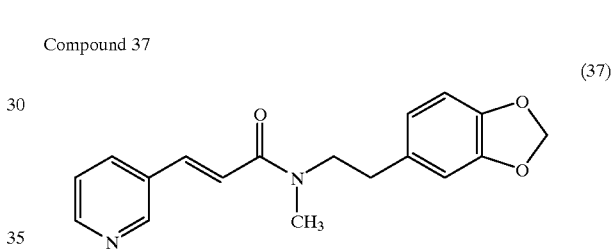
(37)

Properties: mp 93–95° C. (ethyl acetate-hexane)

$^1$H-NMR (DMSO-d$_6$, 150° C.) δ: 2.78 (2H, t, J=7.2 Hz), 2.99 (3H, s), 3.64 (2H, t, J=7.2 Hz), 5.85 (2H, s), 6.63–6.76 (3H, m), 6.97 (1H, d, J=15.6 Hz), 7.30–7.37 (2H, m), 7.89–7.93 (1H, m), 8.48–8.50 (1H, m), 8.70 (1H, br s)

EXAMPLE 38

Compound 38

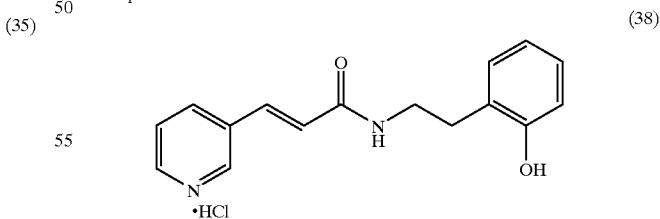
(38)

Properties: solid $^1$H-NMR (DMSO-d$_6$) δ: 2.74 (2H, t, J=7.4 Hz), 3.35–3.46 (2H, m) 6.67–6.75 (1H, br s), 6.81–7.09 (4H, m), 7.57 (1H, d, J=15.9 Hz), 7.93–8.00 (1H, m), 8.42–8.48 (1H, m), 8.57–8.61 (1H, m), 8.81–8.83 (1H, m), 9.06–9.07 (1H, m)

EXAMPLE 39

Compound 39

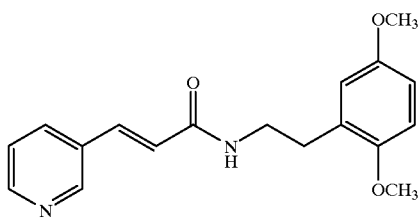
(39)

Properties: mp 105–107° C. (ethyl acetate)

$^1$H-NMR (DMSO-d$_6$) δ: 2.77 (2H, t, J=7.2 Hz), 3.36–3.47 (2H, m), 3.69 (3H, s), 3.75 (3H, s), 6.68 (1H, d, J=15.7 Hz), 6.69–6.75 (2H, m), 6.84–6.90 (1H, m), 7.34–7.41 (1H, m), 7.42 (1H, d, J=15.7 Hz), 7.70–7.86 (1H, br), 7.86–7.92 (1H, m), 8.49–8.52 (1H, m), 8.69–8.70 (1H, m)

EXAMPLE 40

Compound 40

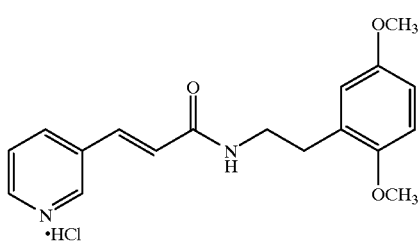
(40)

Properties: mp 144–146° C. (ethanol)

$^1$H-NMR (DMSO-d$_6$) δ: 2.75 (2H, t, J=7.2 Hz), 3.34–3.47 (2H, m), 3.68 (3H, s), 3.74 (3H, s), 6.72–6.78 (2H, m), 6.86–6.92 (1H, m), 6.94 (1H, d, J=15.9 Hz), 7.57 (1H, t, J=15.9 Hz), 7.95–8.02 (1H, m), 8.45–8.52 (1H, br), 8.61 (1H, d, J=8.1 Hz), 8.83 (1H, d, J=5.4 Hz), 9.08 (1H, s)

EXAMPLE 41

Compound 41

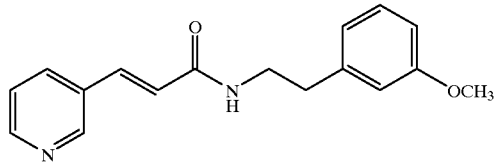
(41)

Properties: mp 90–92° C. (chloroform-hexane)

$^1$H-NMR (CDCl$_3$) δ: 2.88 (3H, t, J=6.8 Hz), 3.64–3.70 (2H, m), 3.80 (3H, s), 5.80–5.90 (1H, br), 6.40 (1H, d, J=15.6 Hz), 6.77–6.83 (3H, m), 7.24 (1H, t, J=7.8 Hz), 7.27–7.31 (1H, m), 7.61 (1H, d, J=15.6 Hz), 7.74–7.78 (1H, m), 8.53–8.56 (1H, m), 8.69–8.71 (1H, m)

EXAMPLE 42

Compound 42

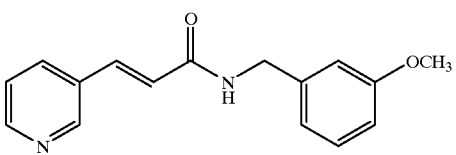
(42)

Properties: mp 81–83° C. (chloroform-ether)

$^1$H-NMR (CD$_3$OD) δ: 3.77 (3H, s), 4.45–4.49 (2H, m), 6.77 (1H, d, J=15.9 Hz), 6.79–6.92 (3H, m), 7.24 (1H, t, J=8.1 Hz), 7.43–7.50 (1H, m), 7.59 (1H, d, J=15.9 Hz), 8.01–8.08 (1H, m), 8.49–8.52 (1H, m), 8.71 (1H, br s)

EXAMPLE 43

Compound 43

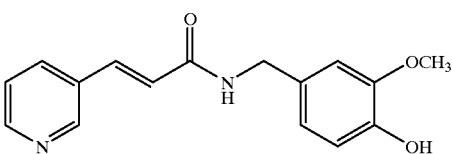
(43)

Properties: mp 160–162° C. (methanol)

$^1$H-NMR (CD$_3$OD) δ: 3.85 (3H, s), 4.41 (2H, s), 6.72–6.81 (2H, m), 6.75 (1H, d, J=15.9 Hz), 6.90–6.92 (1H, m), 7.46 (1H, dd, J=8.0, 4.9 Hz), 7.59 (1H, d, J=15.9 Hz), 8.00–8.07 (1H, m), 8.50 (1H, dd, J=4.9, 1.5 Hz), 8.71 (1H, d, J=2.1 Hz)

EXAMPLE 44

Compound 44

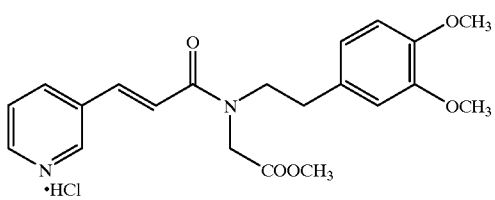
(44)

Properties: mp 168–170° C. (methanol)

$^1$H-NMR (DMSO-d$_6$, 100° C.) δ: 2.80 (2H, t, J=7.0 Hz), 3.60–3.80 (1H, m), 4.10–4.30 (2H, m), 6.72–6.86 (3H, m), 7.05 (1H, d, J=15.3 Hz), 7.40 (1H, d, J=15.3 Hz), 7.63 (1H, dd, J=8.1, 5.1 Hz), 8.22–8.27 (1H, m), 8.60–8.64 (1H, m), 8.87 (1H, s)

EXAMPLE 45

Compound 45

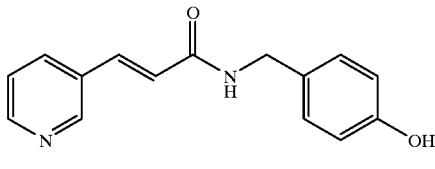
(45)

Properties: mp 193–195° C. (methanol)

$^1$H-NMR (DMSO-d$_6$) δ: 4.29 (2H, d, J=5.8 Hz), 6.72 (2H, d, J=8.4 Hz), 6.78 (1H, d, J=16.0 Hz), 7.11 (2H, d, J=8.4 Hz), 7.40–7.48 (1H, m), 7.49 (1H, d, J=16.0 Hz), 7.94–8.01 (1H, m), 8.53–8.57 (2H, m), 8.75 (1H, d, J=1.9 Hz), 9.32 (1H, s)

EXAMPLE 46

Compound 46

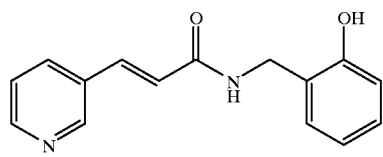
(46)

Properties: mp 172.5–174.5° C. (methanol)

$^1$H-NMR (DMSO-d$_6$) δ: 4.34 (2H, d, J=5.8 Hz), 6.72–6.84 (2H, m), 6.84 (1H, d, J=16.0 Hz), 7.04–7.16 (2H, m), 7.41–7.48 (1H, m), 7.51 (1H, d, J=16.0 Hz), 7.95–8.01 (1H, m), 8.54–8.60 (2H, m), 8.76 (1H, s), 9.64 (1H, s)

EXAMPLE 47

Compound 47

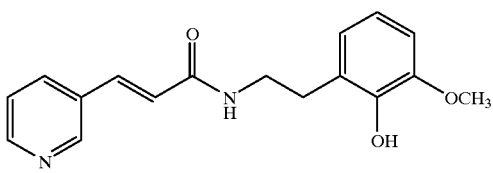
(47)

Properties: mp 174–176° C. (methanol)

$^1$H-NMR (DMSO-d$_6$) δ: 2.74. (2H, t, J=7.4 Hz), 3.30–3.42 (2H, m) 3.78 (3H, s),6.67–6.86 (3H, m), 6.71 (1H, d, J=15.9 Hz), 7.41–7.48 (1H, m), 7.45 (1H, d, J=15.9 Hz), 7.94–8.00 (1H, m), 8.21–8.27 (1H, br), 8.53–8.56 (1H, m), 8.56 (1H, s), 8.75 (1H, d, J=2.0 Hz)

EXAMPLE 48

Compound 48

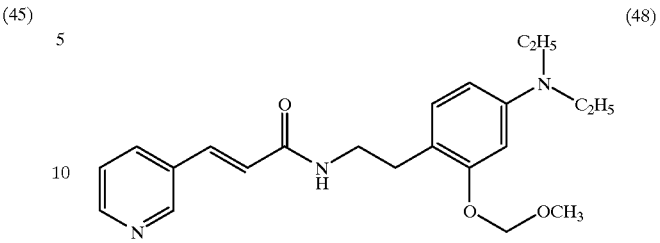
(48)

Properties: solid $^1$H-NMR (CDCl$_3$) δ: 1.16 (6H, t, J=7.0 Hz), 2.81 (2H, t, J=6.5 Hz), 3.33 (4H, q, J=7.0 Hz), 3.51 (3H, s), 3.56–3.65 (2H, m), 5.22 (2H, s), 5.95–6.05 (1H, br), 6.31 (1H, dd, J=8.4, 2.5 Hz), 6.40 (1H, d, J=15.7 Hz), 6.46 (1H, d, J=2.5 Hz), 6.98 (1H, d, J=8.4 Hz), 7.26–7.33 (1H, m), 7.58 (1H, d, J=15.7 Hz), 7.73–7.79 (1H, m), 8.53–8.57 (1H, m), 8.72 (1H, d, J=2.1 Hz)

EXAMPLE 49

Compound 49

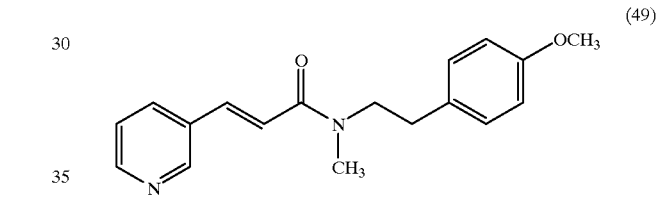
(49)

Properties: mp 113–115° C. (acetone)

$^1$H-NMR (DMSO-d$_6$, 100° C.) δ: 2.75–2.82 (2H, m), 2.98 (3H, s), 3.60–3.68 (2H, m), 3.68 (3H, s), 6.77–6.84 (2H, m), 6.98 (1H, d, J=15.7 Hz), 7.09–7.16 (2H, m), 7.30–7.36 (1H, m), 7.34 (1H, d, J=15.7 Hz), 7.89–7.96 (1H, m), 8.48–8.52 (1H, m), 8.71 (1H, d, J=2.1 Hz)

EXAMPLE 50

Compound 50

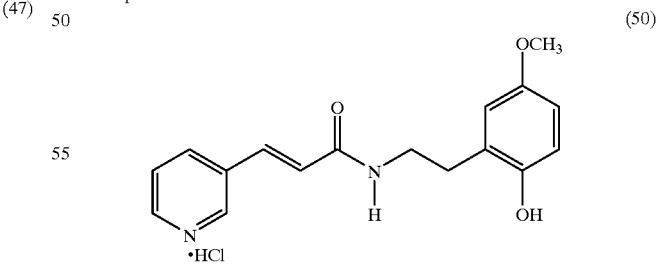
(50)

Properties: mp 185–187° C. (methanol)

$^1$H-NMR (CD$_3$OD) δ: 2.85 (2H, t, J=7.2 Hz), 3.57 (2H, t, J=7.2 Hz), 3.70 (3H, s), 6.59–6.73 (3H, m), 6.92 (1H, d, J=15.9 Hz), 7.63 (1H, d, J=15.9 Hz), 8.06–8.13 (1H, m), 8.80–8.83 (2H, m), 9.06 (1H, s)

EXAMPLE 51

Compound 51

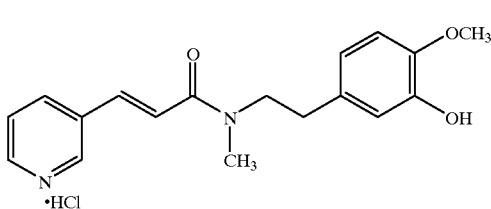
(51)

Properties: amorphous $^1$H-NMR (DMSO-$d_6$, 100° C.) δ: 2.75 (2H, t, J=7.5 Hz), 3.02 (3H, s) 3.66 (2H, t, J=7.5 Hz), 3.73 (3H, s), 6.64 (1H, dd, J=8.1, =2.1 Hz), 6.72 (1H, d, J=2.1 Hz), 6.82 (1H, d, J=8.1 Hz), 6.95–7.17 (1H, m), 7.41 (1H, d, J=15.7 Hz), 7.52–7.82 (1H, m), 8.17 (1H, m), 8.59–8.61 (1H, m), 8.85 (1H, m)

EXAMPLE 52

Compound 52

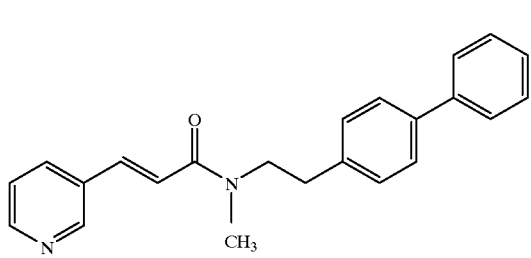
(52)

Properties: mp 123–124° C. (dichloromethane-hexane)

$^1$H-NMR (DMSO-$d_6$, 100° C.) δ: 2.90 (2H, t, J=7.2 Hz), 3.03 (3H, s), 3.74 (2H, t, J=7.2 Hz), 7.00–7.08 (1H, m), 7.26–7.44 (7H, m), 7.51–7.56 (4H, m), 7.95 (1H, m), 8.50 (1H, dd, J=4.8, 1.5 Hz), 8.73 (1H, m)

EXAMPLE 53

Compound 53

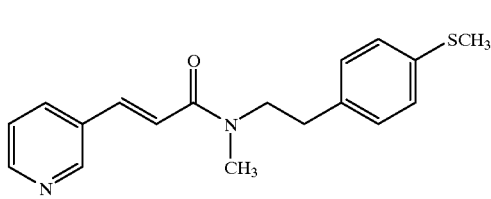
(53)

Properties: mp 121–122° C. (ethanol)

$^1$H-NMR (DMSO-$d_6$, 100° C.) δ: 2.38 (3H, s), 2.83 (2H, m) 2.99 (3H, s), 3.67 (2H, t, J=7.2 Hz), 6.99 (1H, d, J=15.5 Hz), 7.18 (4H, m), 7.21–7.34 (2H, m), 7.91–7.95 (1H, m), 8.50 (1H, dd, J=4.7, 1.4 Hz), 8.71 (1H, m)

EXAMPLE 54

Compound 54

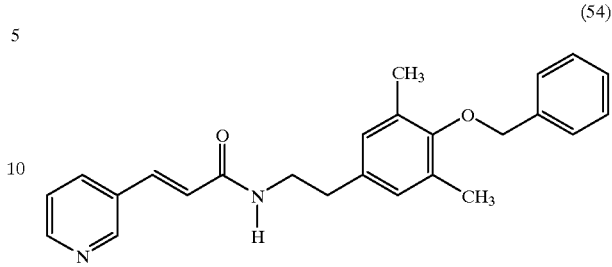
(54)

Properties: amorphous $^1$H-NMR (CDCl$_3$) δ: 2.29 (6H, s), 2.79 (2H, t, J=6.9 Hz), 3.58–3.68 (2H, m), 4.80 (2H, s), 5.88 (1H, m), 6.41 (1H, d, J=15.7 Hz), 6.89 (2H, s), 7.29–7.51 (6H, m), 7.62 (1H, d, J=15.7 Hz), 7.74–7.77 (1H, m), 8.55 (1H, dd, J=4.8, 1.5 Hz), 8.71 (1H, d, J=1.9 Hz)

EXAMPLE 55

Compound 55

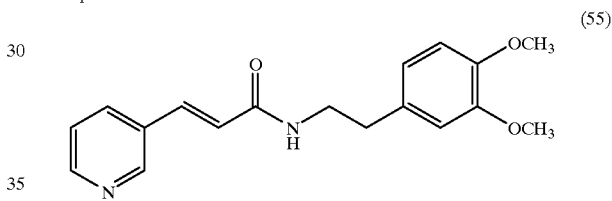
(55)

Properties: mp 113–114° C. (ethyl acetate-hexane)

$^1$H-NMR (CDCl$_3$) δ: 2.85 (2H, t, J=6.8 Hz), 3.66 (2H, td, J=6.8, 6.8 Hz), 3.87 (6H, s), 5.73 (1H, br), 6.39 (1H, d, J=15.6 Hz), 6.74–6.86 (3H, m), 7.30 (1H, dd, J=7.6, 4.9 Hz), 7.62 (1H, d, J=15.6 Hz), 7.77 (1H, ddd, J=7.6, 2.2, 1.7 Hz), 8.56 (1H, dd, J=4.9, 1.7 Hz), 8.72 (1H, d, J=2.2 Hz)

EXAMPLE 56

Compound 56

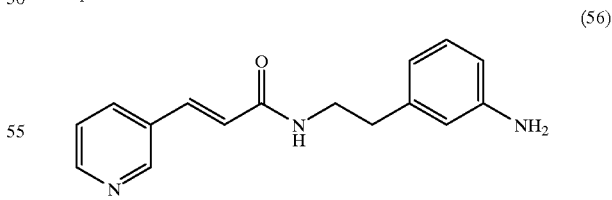
(56)

Properties: mp 182–183° C. (ethanol-ethyl acetate)

$^1$H-NMR (DMSO-$d_6$) δ: 4.22 (2H, d, J=6 Hz), 6.52 (2H, d, J=8 Hz), 6.78 (1H, d, J=16 Hz), 6.96 (2H, d, J=8 Hz), 7.44 (1H, dd, J=8, 5 Hz), 7.48 (1H, d, 16 Hz), 7.96 (1H, d, J=8 Hz), 8.45 (1H, t, J=6 Hz), 8.54 (1H, d, J=5 Hz), 8.75 (1H, d, J=2 Hz)

EXAMPLE 57

Compound 57

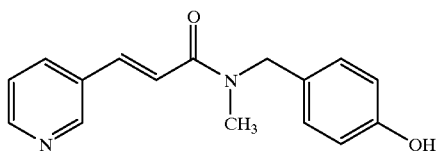
(57)

Properties: mp 179–181° C. (ethanol-ethyl acetate)

$^1$H-NMR (DMSO-$d_6$, 100° C.) δ: 2.97 (3H, S), 4.56 (2H, s), 6.73 (2H, d, J=8 Hz), 7.06 (2H, d, J=8 Hz), 7.26 (1H, d, J=16 Hz), 7.37 (1H, dd, J=8, 5 Hz), 7.51 (1H, d, J=16 Hz), 8.03 (1H, ddd, J=8, 2, 2 Hz), 8.51 (1H, dd, J=5, 2 Hz), 8.79 (1H, d, J=2 Hz), 8.93 (1H, br)

EXAMPLE 58

Compound 58

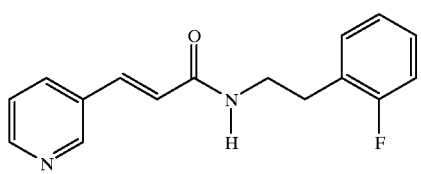
(58)

Properties: mp 90–91° C. (ethyl acetate-hexane)

$^1$H-NMR (DMSO-$d_6$) δ: 2.83 (2H, t, J=7 Hz), 3.43 (2H, td, J=7, 6 Hz), 6.70 (1H, d, J=16 Hz), 7.10–7.36 (4H, m), 7.42–7.50 (1H, m), 7.46 (1H, d, J=16 Hz), 7.98 (1H, ddd, J=8, 2, 2 Hz), 8.32 (1H, t, J=6 Hz), 8.55 (1H, dd, J=5, 2 Hz), 8.75 (1H, d, J=2 Hz)

EXAMPLE 59

Compound 59

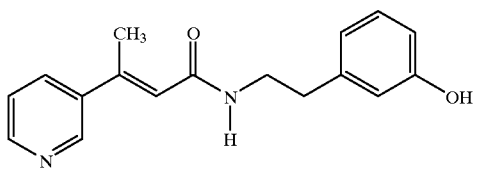
(59)

Properties: mp 96–97° C. (ethyl acetate)

$^1$H-NMR (CD$_3$OD) δ: 2.49 (3H, d, J=1Hz), 2.78 (2H, t, J=7 Hz), 3.48 (2H, t, J=7 Hz), 6.22 (1H, d, J=1Hz), 6.60–6.73 (3H, m), 7.10 (1H, t, J=8 Hz), 7.44 (1H, dd, J=8, 5 Hz), 7.94 (1H, d, J=8 Hz), 8.49 (1H, d, J=5 Hz), 8.64 (1H, d, J=2 Hz)

EXAMPLE 60

Compound 60

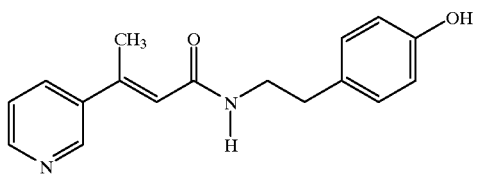
(60)

Properties: mp 176–179° C. (ethyl acetate)

$^1$H-NMR (DMSO-$d_6$) δ: 2.48 (3H, d, J=1Hz), 2.64 (2H, t, J=7 Hz), 3.25–3.32 (2H, m), 6.25 (1H, d, J=1Hz), 6.68 (2H, d, J=8 Hz), 7.02 (2H, d, J=8 Hz), 7.43 (1H, dd, J=8, 5 Hz), 7.88 (1H, d, J=8 Hz), 8.10 (1H, t, J=6 Hz), 8.55 (1H, dd, J=5, 2 Hz), 8.70 (1H, d, J=2 Hz), 9.20 (1H, s)

EXAMPLE 61

Compound 61

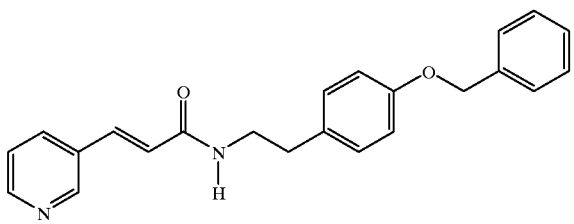
(61)

Properties: mp 157–158° C. (ethanol-ethyl acetate)

$^1$H-NMR (CDCl$_3$) δ: 2.84 (2H, t, J=7 Hz), 3.64 (2H, td, J=7, 6 Hz), 5.01 (2H, s), 5.67 (1H, br), 6.38 (1H, d, J=16 Hz), 6.94 (2H, d, J=9 Hz), 7.14 (2H, d, J=9 Hz), 7.29–7.45 (6H, m), 7.61 (1H, d, J=16 Hz), 7.77 (1H, d, J=8 Hz), 8.56 (1H, dd, J=5, 2 Hz), 8.72 (1H, d, J=2 Hz)

EXAMPLE 62

Compound 62

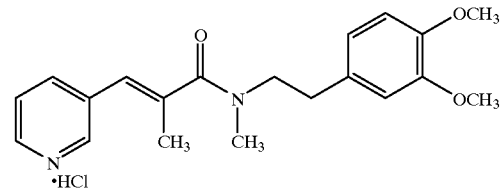
(62)

Properties: amorphous $^1$H-NMR (DMSO-$d_6$, 100° C.) δ: 1.89 (3H, d, J=1Hz), 2.80 (2H, t, J=7 Hz), 2.95 (3H, s), 3.59 (2H, t, J=7 Hz), 3.70 (3H, S), 3.72 (3H, s), 6.26 (1H, br s), 6.72 (1H, dd, J=8, 2 Hz), 6.79 (1H, d, J=2 Hz), 6.84 (1H, d, J=8 Hz), 7.34–7.38 (1H, m), 7.68–7.70 (1H, m), 8.44–8.45 (1H, m), 8.49–8.50 (1H, m)

EXAMPLE 63

Compound 63

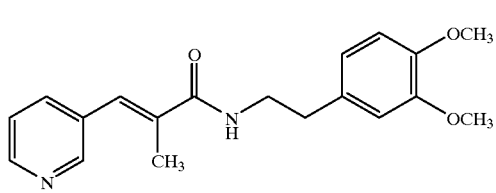
(63)

Properties: oil

¹H-NMR (CDCl$_3$) δ: 2.05 (3H, d, J=1Hz), 2.86 (2H, t, J=7 Hz), 3.63 (2H, td, J=7, 6 Hz), 3.87 (6H, s), 6.12 (1H, t, J=6 Hz), 6.75–6.86 (3H, m), 7.25–7.34 (2H, m), 7.59–7.63 (1H, m), 8.49–8.54 (2H, m)

EXAMPLE 64

Compound 64

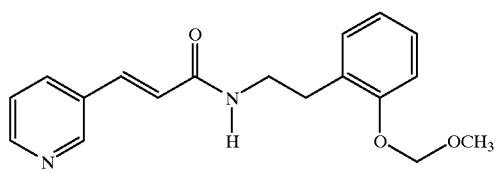
(64)

Properties: mp 75–77° C. (ethyl acetate-hexane)

¹H-NMR (CDCl$_3$) δ: 2.94 (2H, t, J=7 Hz), 3.51 (3H, s), 3.67 (2H, td, J=7, 6 Hz), 5.24 (2H, s), 5.96 (1H, br), 6.40 (1H, d, J=16 Hz), 6.93–7.30 (5H, m), 7.59 (1H, d, J=16 Hz), 7.76 (1H, d, J=8 Hz), 8.56 (1H, dd, J=5, 1 Hz), 8.72 (1H, d, J=2 Hz)

EXAMPLES 65 to 68

The compounds obtained in Examples 28, 36, 48 and 54 were alkali- or acid hydrolyzed in a conventional manner to yield Compounds 65, 66, 67 and 68, respectively.

EXAMPLE 65

Compound 65

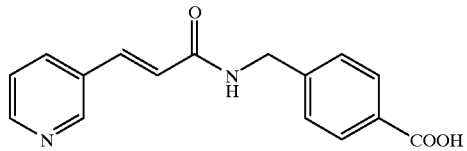
(65)

Properties: mp 245–248° C.

¹H-NMR (DMSO-d$_6$) δ: 4.49 (2H, d, J=6 Hz), 6.82 (1H, d, J=16 Hz), 7.39–7.46 (1H, m), 7.41 (2H, d, J=8 Hz), 7.53 (1H, d, J=16 Hz), 7.92 (2H, d, J=8 Hz), 8.01 (1H, d, J=8 Hz), 8.56 (1H, d, J=5 Hz), 8.75–8.81 (2H, m), 12.9 (1H, br)

EXAMPLE 66

Compound 66

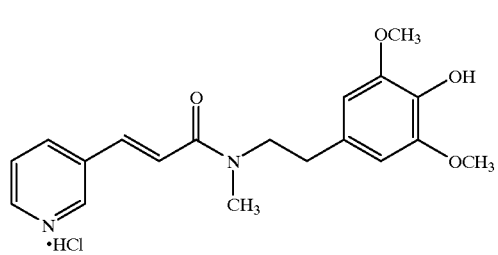
(66)

Properties: mp 152–155° C. (methanol)

¹H-NMR (DMSO-d$_6$, 150° C.) δ: 2.75 (2H, t, J=7.1 Hz), 2.99 (3H, s), 3.66 (2H, t, J=7.1 Hz), 3.73 (6H, s), 6.64 (2H, s), 6.98 (1H, d, J=15.6 Hz), 7.33 (1H, d, J=15.6 Hz), 7.34–7.40 (1H, m), 7.92–7.96 (1H, m), 8.49–8.51 (1H, m), 8.72 (1H, br s)

EXAMPLE 67

Compound 67

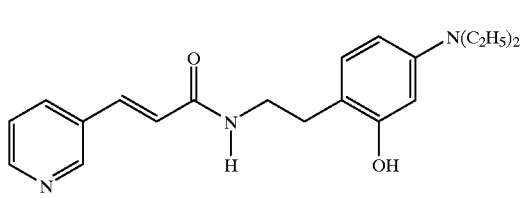
(67)

Properties: mp 150–152° C. (acetone-methanol)

¹H-NMR (DMSO-d$_6$) δ: 1.06 (6H, t, J=6.9 Hz), 2.59 (2H, t, J=7.4 Hz), 3.23 (4H, q, J=6.9 Hz), 3.25–3.35 (2H, m), 6.06 (1H, dd, J=8.3, 2.4 Hz), 6.17 (1H, d, J=2.4 Hz), 6.73 (1H, d, J=15.9 Hz), 6.82 (1H, d, J=8.3 Hz), 7.40–7.48 (1H, m), 7.45 (1H, d, J=15.9 Hz), 7.94–8.00 (1H, m), 8.19 (1H, t, J=5.5 Hz), 8.53–8.57 (1H, m), 8.75 (1H, d, J=1.9 Hz), 8.97 (1H, s)

EXAMPLE 68

Compound 68

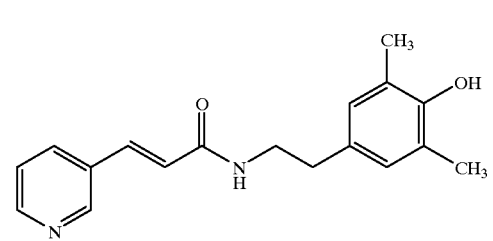
(68)

Properties: mp 137–138° C. (ethyl acetate-hexane)

¹H-NMR (CDCl$_3$) δ: 2.24 (6H, s), 2.76 (2H, t, J=7 Hz), 3.58–3.67 (2H, m), 5.00 (1H, br s), 5.81 (1H, br s), 6.40 (1H, d, J=16 Hz), 6.83 (2H, s), 7.30 (1H, dd, J=8, 5 Hz), 7.60 (1H, d, J=16 Hz), 7.77 (1H, dt, J=8, 2 Hz), 8.55 (1H, dd, J=5, 2 Hz), 8.68 (1H, d, J=2 Hz)

EXAMPLE 69

Synthesis of (Z)-N-(3-methoxyphenethyl)-3-phenyl-3-(3-pyridyl)-2-propenoic acid amide (Compound 69)

Compound 69

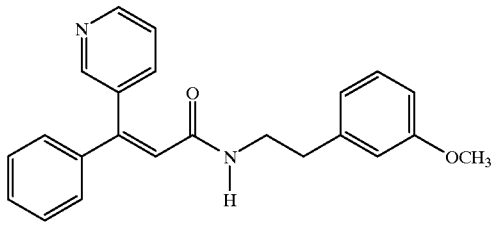
(69)

A mixture of 60% sodium hydride (528 mg), methyl dimethylphosphonoacetate (2.20 g) and tetrahydrofuran (100 ml) was stirred at room temperature for 1 hour and under ice-cooling and stirring 3-benzoylpyridine (2.01 g) was added and stirred at room temperature for 18 hours. The reaction mixture was poured into ice water, extracted with ethyl acetate, washed with water and dried over magnesium sulfate. The solvent was distilled out under reduced pressure and sodium hydroxide (4.40 g)/water (22 ml)-methanol (22 ml) was added to the residue and stirred at room temperature for 5 hours. The reaction mixture was made acidic with hydrogen chloride/methanol and concentrated under reduced pressure and the precipitated inorganic salts were washed with ethanol-ethyl acetate and filtered out. The filtrate was concentrated and the residue was recrystallized to yield (Z)-3-phenyl-3-(3-pyridyl)-2-propenoic acid hydrochloride (1.00 g, 35%) as a primary crystal.

$^1$H-NMR (CD$_3$OD) δ: 6.74 (1H, s), 7.35–7.52 (5H, m), 8.09– 8.16 (1H, m), 8.43–8.49 (1H, m), 8.73–8.90 (2H, m)

Further, (E)-3-phenyl-3-(3-pyridyl)-2-propenoic acid hydrochloride (0.40 g, 14%) as a secondary crystal was obtained from the mother liquor.

$^1$H-NMR (CD$_3$OD) δ: 6.73 (1H, s), 7.27–7.50 (5H, m), 8.05–8.15 (1H, m), 8.49–8.57 (1H, m), 8.78–8.91 (2H, m)

Starting from (Z)-3-phenyl-3-(3-pyridyl)-2-propenoic acid hydrochloride (1.00 g) and 3-methoxyphenethylamine (0.60 g), the titled compound (1.33 g, 98%) was obtained according to the method similar to that of Example 9.

Properties: oil $^1$H-NMR (CDCl$_3$) δ: 2.66 (2H, t, J=7 Hz), 3.41–3.51 (2H, m), 3.79 (3H, s), 5.50–5.68 (1H, m), 6.34 (1H, s), 6.64–6.68 (2H, m), 6.73–6.79 (1H, m), 7.18–7.35 (7H, m), 7.52–7.58 (1H, m), 8.45–8.46 (1H, m), 8.57–8.60 (1H, m)

EXAMPLE 70

Synthesis of (E)-N-(2-hydroxyphenethyl)-3-(3-pyridyl)-2-propenoic acid amide (Compound 70)

Compound 70

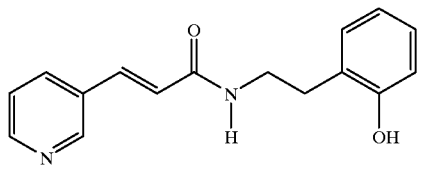
(70)

Trans-3-(3-pyridyl)acrylic acid (22.35 g) and N,N'-carbonyldiimidazole (24.54 g) were dissolved in dimethylformamide (300 ml) and stirred at 40° C. for 40 minutes. Then, potassium carbonate (41.4 g) and 2-hydroxyphenethylamine hydrobromide (32.70 g) were added under room temperature and stirred for 1 hour. Insoluble materials were filtered out and the filtrate was concentrated under reduced pressure. Dilute hydrochloric acid was added to the residue under ice-cooling and stirring. The precipitated crystal was filtered out, washed with water, purified by silica gel column chromatography (chloroform:methanol=20:1) and then recrystallized in methanol to yield the titled compound (24.98 g, 62%).

Properties: mp 170–172° C. (methanol)

$^1$H-NMR (CD$_3$OD) δ: 2.87 (2H, t, J=7 Hz), 3.55 (2H, t, J=7 Hz), 6.72–6.78 (3H, m), 6.99–7.10 (2H, m), 7.42–7.57 (2H, m), 7.99–8.04 (1H, m), 8.48–8.51 (1H, m), 8.68–8.69 (1H, m)

EXAMPLES 71 to 80

Compounds 71 to 80 were obtained according to the method similar to that of Example 70.

EXAMPLE 71

Compound 71

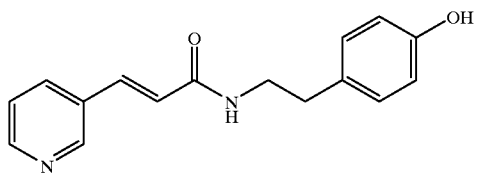
(71)

Properties: mp 217–219° C. (methanol)

$^1$H-NMR (DMSO-d$_6$) δ: 2.51 (2H, t, J=7.1 Hz), 3.16–3.26 (2H, m), 6.53 (2H, d, J=8.4 Hz), 6.57 (1H, d, J=15.9 Hz), 6.87 (2H, d, J=8.4 Hz), 7.28–7.34 (1H, m), 7.30 (1H, d, J=15.9 Hz), 7.79–7.85 (1H, m), 8.06 (1H, br t, J=5.5 Hz), 8.40 (1H, dd, J=4.7, 1.6 Hz), 8.60 (1H, d, J=2.0 Hz), 9.04 (1H, s)

EXAMPLE 72

Compound 72

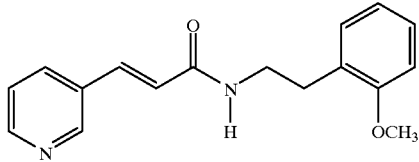
(72)

Properties: oil

¹H-NMR (CDCl₃) δ: 2.91 (2H, t, J=7 Hz), 3.59–3.68 (2H, m), 3.84 (3H, s), 6.14–6.34 (1H, m), 6.42 (1H, d, J=16 Hz), 6.83–7.31 (5H, m), 7.57 (1H, d, J=16 Hz), 7.72–7.78 (1H, m), 8.51–8.54 (1H, m), 8.69–8.70 (1H, m)

EXAMPLE 73

Compound 73

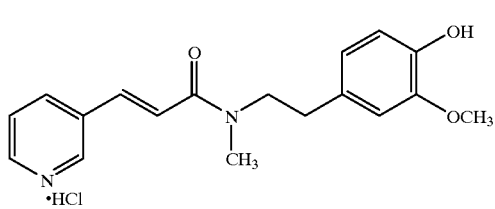
(73)

Properties: mp 192–199° C. (ethanol-methanol)

¹H-NMR (DMSO-d₆, 100° C.) δ: 2.75 (2H, t, J=7 Hz), 2.99 (3H, s), 3.67 (2H, t, J=7 Hz), 3.74 (3H, 8), 6.60 (1H, dd, J=8, 2 Hz), 6.68 (1H, d, J=8 Hz), 6.77 (1H, m), 6.89 (1H, br s), 7.17 (1H, d, J=16 Hz), 7.38 (1H, d, J=16 Hz), 7.73 (1H, dd, J=8, 5 Hz), 8.39 (1H, d, J=8 Hz), 8.66 (1H, dd, J=5, 1 Hz), 8.95 (1H, s)

EXAMPLE 74

Compound 74

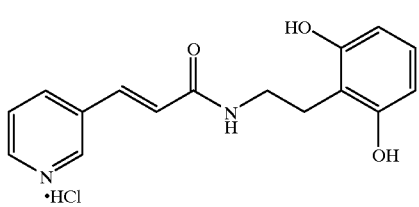
(74)

Properties: mp 215° C. (decomposition) (ethyl acetate-methanol)

¹H-NMR (CD₃OD) δ: 2.92 (2H, t, J=7 Hz), 3.50 (2H, t, J=7 Hz) 6.31 (2H, d, J=8 Hz), 6.82 (1H, t, J=8 Hz), 6.94 (1H, d, J=16 Hz), 7.61 (1H, d, J=16 Hz), 8.08–8.14 (1H, m), 8.80–8.84 (2H, m), 9.07 (1H, s)

EXAMPLE 75

Compound 75

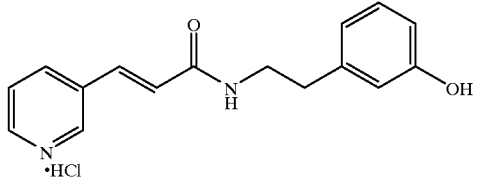
(75)

Properties: mp 155–159° C. (ethanol)

¹H-NMR (DMSO-d₆) δ: 2.70 (2H, t, J=7.3 Hz), 3.35–3.45 (2H, m), 6.57–6.67 (3H, m), 6.88 (1H, d, J=15.9 Hz), 7.04–7.12 (1H, m), 7.55 (1H, d, J=15.9 Hz), 7.84–7.92 (1H, m), 8.40 (1H, t, J=5.6 Hz), 8.49 (1H, d, J=8.2 Hz), 8.78 (1H, d, J=5.Hz), 9.01 (1H, s)

EXAMPLE 76

Compound 76

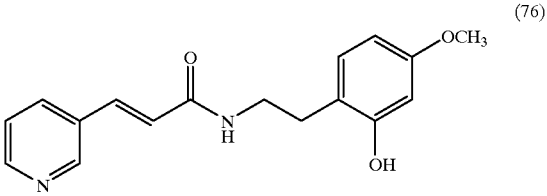
(76)

Properties: mp 203–205° C. (methanol)

¹H-NMR (DMSO-d₆) δ: 2.65 (2H, t, J=7.3 Hz), 3.27–3.39 (2H, m), 3.66 (3H, s), 6.31 (1H, dd, J=8.2, 2.5 Hz), 6.39 (1H, d, J=2.5 Hz), 6.72 (1H, d, J=15.8 Hz), 6.95 (1H, d, J=8.2 Hz), 7.40–7.48 (1H, m), 7.45 (1H, d, J=15.8 Hz), 7.94–8.00 (1H, m), 8.18–8.24 (1H, br), 8.53–8.56 (1H, m), 8.75 (1H, d, J=1.9 Hz), 9.43 (1H, s)

EXAMPLE 77

Compound 77

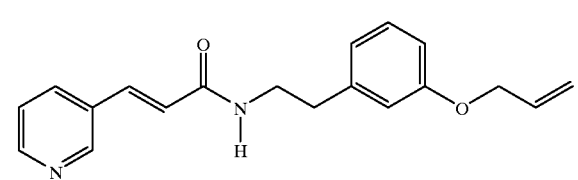
(77)

Properties: mp 82.5–84.5° C. (ethyl acetate)

¹H-NMR (CDCl₃) δ: 2.87 (2H, t, J=6.8 Hz), 3.62–3.72 (2H, m), 4.51–4.55 (2H, m), 5.28 (1H, dd, J=10.5, 1.5 Hz), 5.41 (1H, dd, J=17.3, 1.5 Hz), 5.72–5.80 (1H, br), 6.04 (1H, ddd, J=17.3, 10.5, 5.3 Hz), 6.39 (1H, d, J=15.7 Hz), 6.78–6.84 (3H, m), 7.19–7.33 (2H, m), 7.61 (1H, d, J=15.7 Hz), 7.73–7.80 (1H, m), 8.53–8.57 (1H, m), 8.71 (1H, d J=1.7 Hz)

EXAMPLE 78

Compound 78

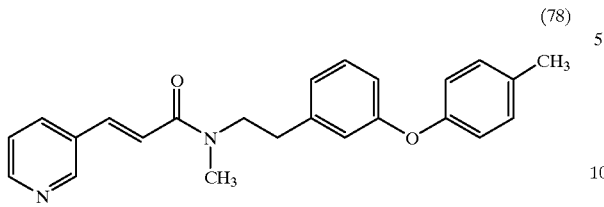
(78)

Properties: oil $^1$H-NMR (DMSO-d$_6$, 100° C.) δ: 2.25 (3H, s), 2.80–2.88 (2H, m), 2.93 (3H, s), 3.64–3.72 (2H, m), 6.71–7.15 (8H, m), 7.19–7.28 (1H, m), 7.33–7.40 (1H, m), 7.37 (1H, d, J=15.2 Hz), 7.94–7.99 (1H, m), 8.49–8.53 (1H, m), 8.73–8.74 (1H, m)

EXAMPLE 79

Compound 79

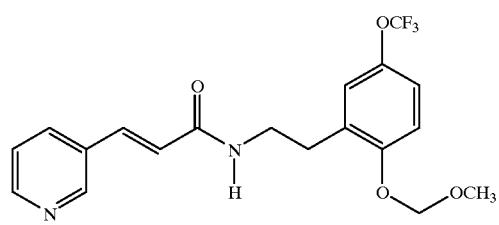
(79)

Properties: oil $^1$H-NMR (CDCl$_3$) δ: 2.93 (2H, t, J=6.7 Hz), 3.50 (3H, s), 3.60–3.71 (2H, m), 5.22 (2H, s), 5.85–5.93 (1H, br), 6.40 (1H, d, J=15.7 Hz), 7.02–7.14 (3H, m), 7.26–7.34 (1H, m), 7.60 (1H, d, J=15.7 Hz), 7.77 (1H, d, J=7.9 Hz), 8.56 (1H, d, J=4.6 Hz), 8.71 (1H, s)

EXAMPLE 80

Compound 80

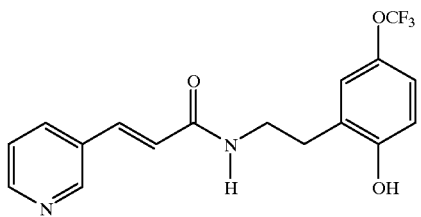
(80)

Properties: mp 178–180° C. (acetone)

$^1$H-NMR (DMSO-d$_6$) δ: 2.75 (2H, t, J=7.1 Hz), 3.36–3.46 (2H, m), 6.70 (1H, d, J=15.8 Hz), 6.86 (1H, d, J=8.9 Hz), 6.99–7.15 (2H, m), 7.40–7.48 (1H, m), 7.45 (1H, d, J=15.8 Hz), 7.93–8.00 (1H, m), 8.25 (1H, t, J=5.6 Hz), 8.53–8.56 (1H, m), 8.74 (1H, d, J=1.5 Hz), 9.83 (1H, s)

EXAMPLE 81

Synthesis of (E)-N-(3-hydroxyphenethyl)-3-(3-pyridyl)-2-propenoic acid amide (Compound 81)

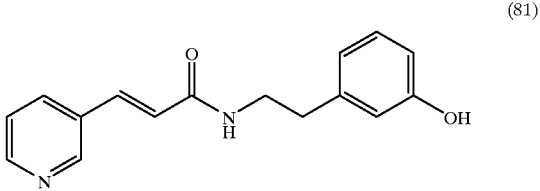
(81)

To a solution of trans-3-(3-pyridyl)acrylic acid (179 g) in dichloromethane (4.8 L), triethylamine (584 ml) and pivaloyl chloride (148 ml) were sequentially added under ice-cooling and stirring and stirred for 15 minutes. Subsequently, 3-hydroxyphenethylamine hydrobromide (263 g) was added at the same temperature and stirred for 2 hours. After the solvent was distilled out under reduced pressure, water was added to the residue and the precipitated crystal was filtered, washed with water and recrystallized in ethanol to yield the titled compound (251.4 g, 78%).

Properties: mp 163.0–164.5° C.(ethanol)

$^1$H-NMR (DMSO-d$_6$) δ: 2.70 (2H, t, J=7 Hz), 3.40 (2H, td, J=7, 5 Hz), 6.59–6.66 (3H, m), 6.73 (1H, d, J=16 Hz), 7.04–7.12 (1H, m), 7.39–7.45 (1H, m), 7.46 (1H, d, J=16 Hz), 7.94–7.98 (1H, m), 8.24 (1H, t, J=5 Hz), 8.52–8.56 (1H, m), 8.73–8.74 (1H, m), 9.25 (1H, s)

EXAMPLES 82 and 83

Compounds 82 and 83 were obtained according to the method similar to that of Example 81.

EXAMPLE 82

Compound 82

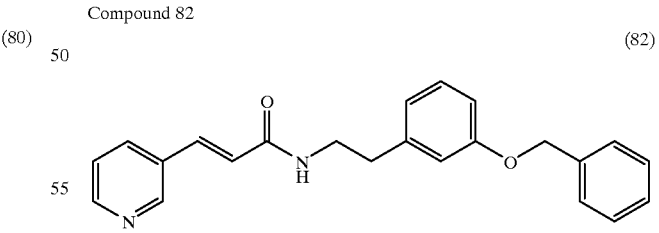
(82)

Properties: mp 115–116° C. (dichloromethane-hexane)

$^1$H-NMR (CDCl$_3$) δ: 2.87 (2H, t, J=6.8 Hz), 3.46–3.71 (2H, m), 5.06 (2H, s), 5.73 (1H, m), 6.37 (1H, d, J=15.7 Hz), 6.81–6.89 (3H, m), 7.21–7.46 (7H, m), 7.61 (1H, d, J=15.7 Hz), 7.73–7.79 (1H, m), 8.56 (1H, dd, J=4.8, 1.5 Hz), 8.72 (1H, d, J=1.9 Hz)

EXAMPLE 83

Compound 83

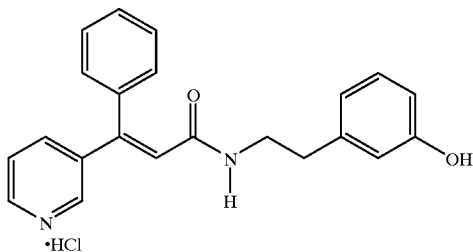
(83)
·HCl

Properties: mp 130–135° C. (ethyl acetate-methanol)

$^1$H-NMR (DMSO-d$_6$) δ: 2.53 (2H, t, J=7 Hz), 3.19–3.25 (2H, m), 6.50 (1H, s), 6.56–6.61 (3H, m), 7.04–7.08 (1H, m), 7.13–7.16 (2H, m), 7.35–7.39 (4H, m), 7.54–7.57 (1H, m), 8.02–8.05 (1H, m), 8.45–8.46 (1H, m), 8.53–8.54 (1H, m), 9.25 (1H, br s)

EXAMPLE 84

Synthesis of (E)-N-(3,4-dimethoxyphenethyl)-N-methyl-3-(3-pyridyl)-2-propenoic acid amide (Compound 84)

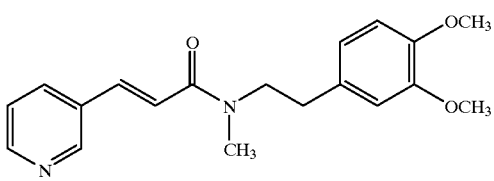
(84)

A mixture of methyl trans-3-(3-pyridyl)acrylate (326 mg), 3,4-dimethoxy-N-methylphenethylamine (390 mg), 60% sodium hydride (80 mg) and diethylene glycol dimethyl ether (2 ml) was stirred at room temperature for 24 hours. Water was added to the reaction mixture, extracted with ethyl acetate, washed with water and dried over magnesium sulfate. After the solvent was distilled out under reduced pressure, the residue was purified by silica gel column chromatography (chloroform:methanol=50:1) and recrystallized to yield the titled compound (278 mg, 43%).

Properties: mp 84–86° C. (ethyl acetate-hexane)

$^1$H-NMR (DMSO-d$_6$, 150° C.) δ: 2.78 (2H, t, J=7.2 Hz), 3.00 (3H, s), 3.67 (2H, t, J=7.2 Hz), 3.69 (3H, s), 3.74 (3H, s), 6.72–6.75 (1H, m), 6.81–6.83 (2H, m), 6.95 (1H, d, J=15.6 Hz), 7.31–7.36 (2H, m), 7.87–7.90 (1H, m), 8.48–8.50 (1H, m), 8.69–8.70 (1H, m)

EXAMPLE 85

Synthesis of (E)-N-(3,4-dihydroxyphenethyl)-N-methyl-3-(3-pyridyl)-2-propenoic acid amide (Compound 85)

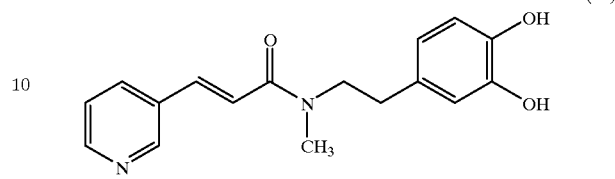
(85)

(E)-N-(3,4-dimethoxyphenethyl)-N-methyl-3-(3-pyridyl)-2-propenoic acid amide (2.65 g, 8.31 mmol) obtained in Example 84 was dissolved in dichloromethane (66 ml) and 1M boron tribromide-dichloromethane solution (33 ml) was dropwise added under argon at −30° C. and stirred for 14 hours. After methanol was added at the same temperature to stop the reaction, the solvent was distilled out under reduced pressure and hydrogen chloride/methanol solution was added to the residue and heated and refluxed for 1 hour. The solvent was distilled out under reduced pressure and potassium hydroxide/methanol solution was added to the residue to neutralize. The precipitated inorganic salts were filtered out and the filtrate was concentrated under reduced pressure. The residue was purified by silica gel column chromatography (chloroform:methanol=30:1) and recrystallized to yield the titled compound (2.19 g, 90%).

Properties: mp 155–158° C. (dichloromethane-hexane-methanol)

$^1$H-NMR (DMSO-d$_6$, 100° C.) δ: 2.68 (2H, t, J=6.8 Hz), 2.98 (3H, s), 3.60 (2H, t, J=6.8 Hz), 6.46–6.51 (1H, m), 6.62–6.66 (2H, m), 7.00 (1H, d, J=16.1 Hz), 7.35–7.39 (1H, m), 7.37 (1H, d, J=16.1 Hz), 7.94–7.98 (1H, m), 8.08 (1H, br s), 8.16 (1H, br s), 8.49–8.52 (1H, m), 8.73–8.74 (1H, m)

EXAMPLES 86 to 93

Starting from the compounds obtained in Examples 11, 31, 32, 39, 42, 55 and 69, Compounds 86, 87, 88, 89, 90, 91 and 92 were obtained, respectively, according to the method similar to that of Example 85. Further, Compound 92 was converted into its hydrochloride in a conventional manner to yield Compound 93.

EXAMPLE 86

Compound 86

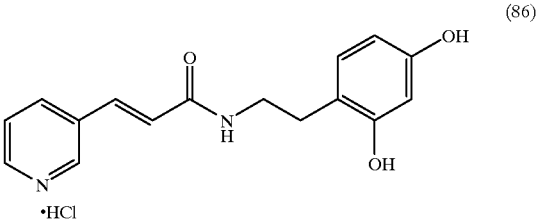
(86)
·HCl

Properties: mp 190–196° C. (methanol)

$^1$H-NMR (DMSO-d$_6$) δ: 2.60 (2H, t, J=7.3 Hz), 3.28–3.36 (2H, m), 6.14 (1H, dd, J=8.2, 2.3 Hz), 6.31 (1H, d, J=2.3 Hz), 6.81 (1H, d, J=8.2 Hz), 6.88 (1H, d, J=15.9 Hz), 7.55 (1H, d, J=15.9 Hz), 7.92 (1H, dd, J=8.2, 5.4 Hz), 8.34 (1H, t, J=5.6 Hz), 8.54 (1H, d, J=8.2 Hz), 8.79 (1H, d, J=5.4 Hz), 9.03 (1H, s)

EXAMPLE 87

Compound 87

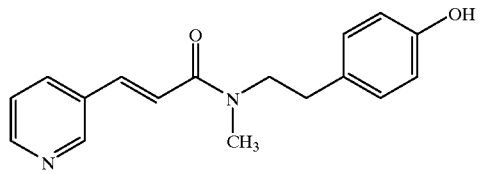
(87)

Properties: mp 155–157° C. (ethyl acetate-methanol)

¹H-NMR (DMSO-d₆, 100° C.) δ: 2.74 (2H, t, J=6.8 Hz), 2.98 (3H, s), 3.62 (2H, t, J=6.8 Hz), 6.66–6.70 (2H, m), 6.99–7.03 (3H, m) 77.3 2–7.40 (2H, m), 7.95–7.99 (1H, m), 8.50–8.52 (1H, m) 8.74 (1H, m), 8.77 (1H, s)

EXAMPLE 88

Compound 88

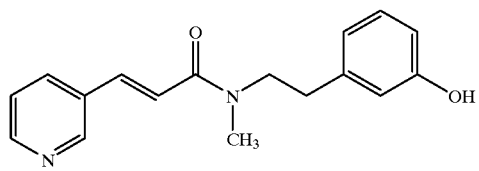
(88)

Properties: amorphous

¹H-NMR (DMSO-d₆, 150° C.) δ: 2.78 (2H, t, J=7.3 Hz), 2.99 (3H, s), 3.65 (2H, t, J=7.3 Hz), 6.57–6.66 (3H, m), 6.93–7.07 (2H, m), 7.30–7.39 (2H, m), 7.88–7.92 (1H, m), 8.47–8.50 (1H, m), 8.70–8.71 (1H, m)

EXAMPLE 89

Compound 89

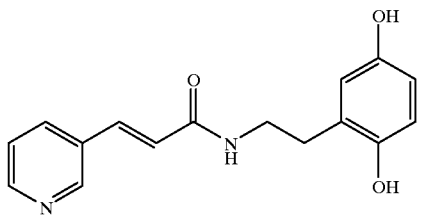
(89)

Properties: mp 193–195° C. (methanol)

¹H-NMR (DMSO-d₆) δ: 2.65 (2H, t, J=7.3 Hz), 3.33–3.38 (2H, m), 6.43 (1H, dd, J=8.5, 2.9 Hz), 6.50 (1H, d, J=2.9 Hz), 6.60 (1H, d, J=8.5 Hz), 6.73 (1H, d, J=15.9 Hz), 7.42–7.46 (1H, m), 7.46 (1H, d, J=15.9 Hz), 7.96–7.99 (1H, m), 8.24 (1H, t, J=5.6 Hz), 8.53–8.56 (1H, m), 8.57 (1H, S), 8.65 (1H, S), 8.74–8.76 (1H, m)

EXAMPLE 90

Compound 90

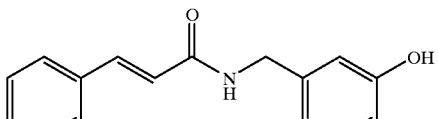
(90)

Properties: mp 164–166° C. (methanol)

¹H-NMR (CD₃OD) δ: 4.43 (2H, s), 6.65–6.81 (3H, m), 6.77 (1H, d, J=15.9 Hz), 7.10–7.18 (1H, m), 7.42–7.50 (1H, m), 7.59 (1H, d, J=15.9 Hz), 8.01–8.08 (1H, m), 8.49–8.53 (1H, m), 8.70–8.72 (1H, m)

EXAMPLE 91

Compound 91

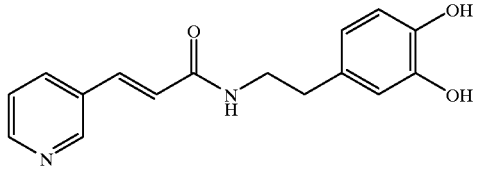
(91)

Properties: mp 222–223° C. (water-methanol)

¹H-NMR (CD₃OD) δ: 2.59 (2H, t, J=7.8 Hz), 3.23–3.41 (2H, m), 6.46 (1H, dd, J=7.8, 2.2 Hz), 6.61 (1H, d, J=2.2 Hz), 6.64 (1H, d, J=7.8 Hz), 6.72 (1H, d, J=16.1 Hz), 7.44 (1H, dd, J=8.3, 4.9 Hz), 7.44 (1H, d, J=16.1 Hz), 7.97 (1H, ddd, J=8.3, 2.2, 1.7 Hz), 8.55 (1H, dd, J=4.9, 1.7 Hz), 8.75 (1H, d, J=2.2 Hz)

EXAMPLE 92

Compound 92

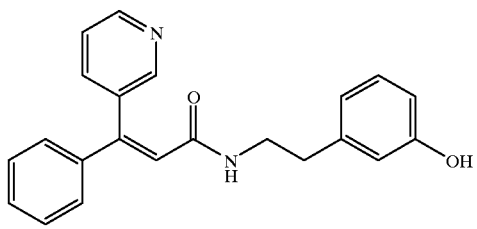
(92)

Properties: amorphous

¹H-NMR (CD₃OD) δ: 2.63 (2H, t, J=7.1 Hz), 3.31–3.38 (2H, m) 6.52 (1H, s), 6.62–6.76 (3H, m), 7.04–7.12 (1H, m), 7.22–7.63 (7H, m), 8.34–8.35 (1H, m), 8.48–8.51 (1H, m)

EXAMPLE 93

Compound 93

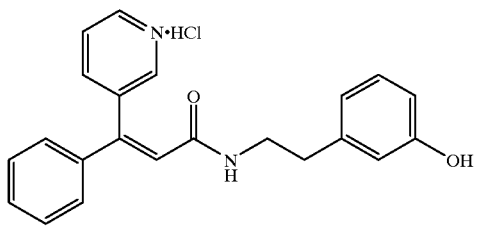
(93)

Properties: mp 188–193° C. (methanol)

$^1$H-NMR (DMSO-d$_6$) δ: 2.57–2.64 (2H, m), 3.19–3.29 (2H, m) 6.59–6.64 (3H, m),6.84 (1H, s), 7.03–7.11 (1H, m), 7.28–7.33 (2H, m), 7.40–7.47 (3H, m), 7.99–8.05 (1H, m), 8.23–8.29 (1H, m), 8.60–8.65 (1H, m), 8.82–8.83 (1H, m), 8.87–8.89 (1H, m)

EXAMPLE 94

Synthesis of methyl [3-[2-[(E)-3-(3-pyridyl)acryloylamino]ethyl]phenoxy]acetate (Compound 94)

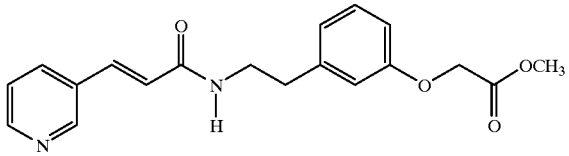
(94)

(E)-N-(3-hydroxyphenethyl)-3-(3-pyridyl)-2-propenoic acid amide (1.07 g, 4.0 mmol) obtained in Example 81 and methyl chloroacetate (0.52 g, 4.8 mmol) were dissolved in dimethylformamide (12 ml) and potassium carbonate (1.66 g, 12 mmol) was added and stirred at 60° C. for 8 hours. After allowing to cool, ethyl acetate was added to the reaction mixture and insoluble materials were filtered out. The filtrate was washed with water and dried over magnesium sulfate. After the solvent was distilled out under reduced pressure, the residue was recrystallized to yield the titled compound (0.83 g, 61%).

Properties: mp 102–104° C. (ethyl acetate)

$^1$H-NMR (DMSO-d$_6$) δ: 2.78 (2H, t, J=7 Hz), 3.44 (2H, td, J=7, 6 Hz), 3.71 (3H, s), 4.79 (2H, s), 6.74 (1H, d, J=16 Hz), 6.76–6.88 (3H, m), 7.23 (1H, t, J=8 Hz), 7.44–7.51 (1H, m), 7.47 (1H, d, J=16 Hz), 7.99 (1H, d, J=8 Hz), 8.27 (1H, t, J=6 Hz), 8.57 (1H, dd, J=5, 1 Hz), 8.77 (1H, d, J=2 Hz)

EXAMPLES 95 to 109

Compounds 95 to 111 were obtained according to the method similar to that of Example 94.

EXAMPLE 95

Compound 95

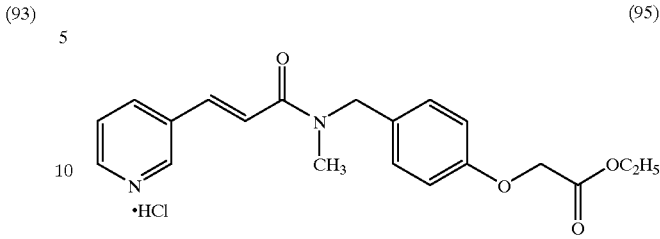
(95)

Properties: mp 126–129° C. (ethanol-ethyl acetate)

$^1$H-NMR (DMSO-d$_6$, 100° C.) δ: 1.20 (3H, t, J=7 Hz), 3.00 (3H, s), 4.17 (2H,q, J=7 Hz), 4.62 (2H, s), 4.68 (2H, s), 6.90 (2H, d, J=9 Hz), 7.19 (2H, d, J=9 Hz), 7.37 (1H, d, J=16 Hz), 7.52–7.63 (2H, m), 8.32 (1H, d, J=8 Hz), 8.61 (1H, dd, J=5, 1 Hz), 8.93 (1H, d, J=2 Hz)

EXAMPLE 96

Compound 96

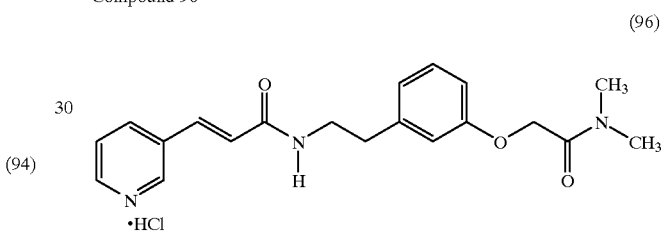
(96)

Properties: amorphous $^1$H-NMR (DMSO-d$_6$) δ: 2.76 (2H, t, J=7 Hz), 2.83 (3H, s), 2.99 (3H, s), 3.44 (2H, td, J=7, 6 Hz), 4.77 (2H, s), 6.72–6.96 (4H, m), 7.20 (1H, t, J=8 Hz), 7.56 (1H, d, J=16 Hz), 7.89–7.96 (1H, m), 8.46–8.56 (2H, m), 8.79 (1H, d, J=5 Hz), 9.03 (1H, S)

EXAMPLE 97

Compound 97

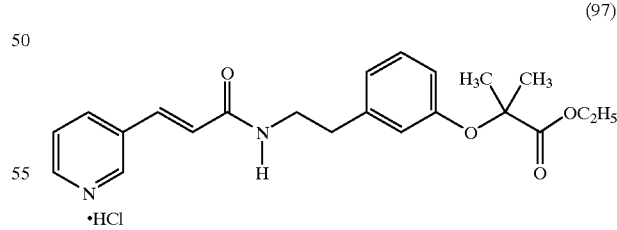
(97)

Properties: mp 111–114° C. (ethanol-ethyl acetate)

$^1$H-NMR (DMSO-d$_6$) δ: 1.16 (3H, t, J=7 Hz), 1.50 (6H, s), 2.74 (2H, t, J=7 Hz), 3.41 (2H, td, J=7, 6 Hz), 4.16 (2H, q, J=7 Hz), 6.59–6.67 (2H, m),6.85–6.89 (1H, m), 6.89 (1H, d, J=16 Hz), 7.19 (1H, t, J=8 Hz), 7.56 (1H, d, J=16 Hz), 7.91 (1H, dd, J=8, 5 Hz), 8.44 (1H, t, J=6 Hz), 8.52 (1H, br d, J=8 Hz), 8.79 (1H, dd, J=5, 1 Hz), 9.03 (1H, d, J=2 Hz)

EXAMPLE 98

Compound 98

(98)

Properties: mp 64–66° C. (ethyl acetate-hexane)

$^1$H-NMR (CDCl$_3$) δ: 1.25 (3H, t, J=7.1 Hz), 2.03–2.16 (2H, m) 2.50 (2H, t, J=7.1 Hz),2.86 (2H, t, J=6.8 Hz), 3.63–3.72 (2H, m), 4.00 (2H, t, J=6.1 Hz), 4.14 (2H, q, J=7.1 Hz), 5.87 (1H, br s), 6.42 (1H, d, J=15.7 Hz), 6.75–6.82 (3H, m), 7.18–7.32 (2H, m), 7.61 (1H, d, J=15.7 Hz),7.74–7.80 (1H, m), 8.54–8.56 (1H, m), 8.71 (1H, br s)

EXAMPLE 99

Compound 99

(99)

Properties: mp 91–93° C. (ethyl acetate)

$^1$H-NMR (CDCl$_3$) δ: 1.28 (3H, t, J=7.1 Hz), 2.86 (2H, t, J=6.7 Hz), 3.60–3.70 (2H, m), 4.24 (2H, q, J=7.1 Hz), 4.62 (2H, s), 5.98 (1H, brt), 6.44 (1H, d, J=15.7 Hz), 6.74–6.88 (3H, m), 7.19–7.32 (2H, m), 7.60 (1H, d, J=15.7 Hz), 7.74–7.80 (1H, m), 8.52–8.56 (1H, m), 8.69–8.71 (1H, m)

EXAMPLE 100

Compound 100

(100)

Properties: mp 129–132° C. (ethanol)

$^1$H-NMR (DMSO-d$_6$) δ: 1.20 (3H, t, J=7.1 Hz), 2.77 (2H, t, J=7.1 Hz), 3.38–3.49 (2H, m), 4.16 (2H, q, J=7.1 Hz), 4.75 (2H, s), 6.73–6.87 (3H, m), 6.91 (H, d, J=16.1 Hz), 7.17–7.26 (1H, m), 7.56 (1H, d, J=16.1 Hz), 7.91–7.98 (1H, m), 8.45 (1H, t, J=5.6 Hz), 8.57 (1H, d, J=8.1 Hz), 8.81 (1H, d, J=5.3 Hz), 9.05 (1H, s)

EXAMPLE 101

Compound 101

(101)

Properties: mp 106–108° C. (ethyl acetate)

$^1$H-NMR (CDCl$_3$) δ: 1.30 (3H, t, J=7.1 Hz), 2.84 (2H, t, J=6.7 Hz), 3.58–3.68 (2H, m), 4.27 (2H, q, J=7.1 Hz), 4.61 (2H, S), 5.70–5.80 (1H, brt), 6.40 (1H, d, J=15.7 Hz), 6.86 (2H, d, J=8.6 Hz), 7.14 (2H, d, J=8.6 Hz), 7.29–7.33 (1H, m), 7.61 (1H, d, J=15.7 Hz), 7.75–7.80 (1H, m), 8.54–8.57 (1H, m), 8.71–8.72 (1H, m)

EXAMPLE 102

Compound 102

(102)

Properties: mp 155.5–157.5° C. (ether-methanol)

$^1$H-NMR (DMSO-d$_6$) δ: 2.84 (2H, t, J=7.2 Hz), 3.40–3.50 (2H, m), 3.71 (3H, s), 4.86 (2H, s), 6.86–6.94 (2H, m), 6.90 (1H, d, J=15.9 Hz), 7.14–7.21 (2H, m), 7.56 (1H, d, J=15.9 Hz), 7.93 (1H, dd, J=8.1, 5.4 Hz),8.39 (1H, t, J=5.3 Hz), 8.54 (1H, d, J=8.1 Hz), 8.80 (1H, d, J=5.4 Hz), 9.04 (1H, s)

EXAMPLE 103

Compound 103

(103)

Properties: mp 131–133° C. (ethanol-ethyl acetate)

$^1$H-NMR (DMSO-d$_6$, 100° C.) δ: 1.20 (3H, t, J=7.1 Hz), 1.21 (3H, t, J=7.1 Hz), 2.77 (2H, t, J=7.0 Hz), 2.98 (3H, s), 3.66 (2H, t, J=7.0 Hz), 4.15 (2H,q, J=7.1 Hz), 4.16 (2H, q, J=7.1 Hz), 4.62 (2H, s), 4.67 (2H, s), 6.75–6.87 (3H, m), 7.10 (1H, d, J=15.7 Hz), 7.39 (1H, d, J=15.7 Hz), 7.52–7.60 (1H, m), 8.18–8.23 (1H, m), 8.57–8.61 (1H, m), 8.85 (1H, s)

EXAMPLE 104

Compound 104 (104)

·HCl

Properties: mp 138–140° C. (ethanol-ethyl acetate)

¹H-NMR (DMSO-d₆, 100° C.) δ: 1.23 (6H, t, J=7.1 Hz), 2.81 (2H, t, J=7.1 Hz), 3.00 (3H, s), 3.67 (2H, t, J=7.1 Hz), 4.29 (4H, q, J=7.1 Hz), 6.77–6.97 (3H, m),7.15 (1H, d, J=15.4 Hz), 7.40 (1H, d, J=15.4 Hz), 7.54–7.61 (1H, m), 8.23 (1H, d, J=8.3 Hz), 8.58–8.62 (1H, m), 8.87 (1H, s)

EXAMPLE 105

Compound 105 (105)

Properties: mp 105–107° C (ethyl acetate)

¹H-NMR (CDCl₃) δ: 1.28 (3H, t, J=7.1 Hz), 3.85 (3H, s), 4.25 (2H, q, J=7.1 Hz),4.51 (2H, d, J=5.7 Hz), 4.66 (2H, s), 6.30–6.40 (1H, br), 6.49 (1H, d, J=15.7 Hz), 6.77 (1H, d, J=8.1 Hz), 6.81–6.89 (2H, m), 7.27–7.34 (1H, m), 7.65 (1H, d, J=15.7 Hz), 7.74–7.80 (1H, m), 8.52–8.56 (1H, m), 8.68–8.69 (1H, m)

EXAMPLE 106

Compound 106 (106)

Properties: oil

¹H-NMR (CDCl₃) δ: 1.10 (3H, t, J=7.1 Hz), 1.22 (3H, t, J=7.1 Hz), 2.86 (2H, t, J=6.6 Hz), 3.37 (2H, q, J=7.1 Hz), 3.39 (2H, q, J=7.1 Hz), 3.60–3.70 (2H, m), 4.69 (2H, s), 6.12–6.16 (1H, br), 6.54 (1H, d, J=15,7 Hz), 6.77–6.85 (3H, m), 7.18–7.37 (2H, m), 7.60 (1H, d, J=15.7 Hz), 7.76–8.47 (1H, m), 8.53–8.56 (1H, m), 8.71 (1H, d, J=1.7 Hz)

EXAMPLE 107

Compound 107 (107)

Properties: oil

¹H-NMR (CDCl₃) δ: 2.86 (2H, t, J=6.6 Hz), 3.20 (3H, s), 3.60–3.70 (2H, m), 3.76 (3H, s), 4.83 (2H, s), 5.98–6.05 (1H, br), 6.48 (1H, d, J=15,7 Hz), 6.77–6.86 (3H, m), 7.19–7.32 (2H, m), 7.59 (1H, d, J=15.7 Hz), 7.75–7.82 (1H, m), 8.53–8.56 (1H, m), 8.71 (1H, s)

EXAMPLE 108

Compound 108 (108)

Properties: mp 115.5–117.5° C. (ethyl acetate)

¹H-NMR (CDCl₃) δ: 1.26 (6H, d, J=6.3 Hz), 2.86 (2H, t, J=6.7 Hz), 3.61–3.71 (2H, m), 4.59 (2H, s), 5.11 (1H, septet, J=6.3 Hz), 5.75–5.85 (1H, br), 6.42 (1H, d, J=15.7 Hz), 6.74–6.80 (2H, m), 6.83–6.88 (1H, m), 7.20–7.33 (2H, m), 7.61 (1H, d, J=15.7 Hz), 7.75–7.82 (1H, m), 8.54–8.58 (1H, m), 8.72 (1H, d, J=2.0 Hz)

EXAMPLE 109

Compound 109 (109)

Properties: mp 130–132° C. (ethanol)

¹H-NMR (CDCl₃) δ: 1.28 (3H, t, J=7.1 Hz), 2.89 (2H, t, J=6.8 Hz), 3.62–3.73 (2H, m), 4.12 (2H, d, J=5.5 Hz), 4.22 (2H, q, J=7.1 Hz), 4.55 (2H, s), 5.75–5.90 (1H, br), 6.41 (1H, d, J=15.7 Hz), 6.79–6.95 (3H, m), 7.00–7.15 (1H, br), 7.23–7.33 (2H, m), 7.62 (1H, d, J=15.7 Hz), 7.75–7.82 (1H, m), 8.54–8.58 (1H, m), 8.73 (1H, d, J=1.9 Hz)

EXAMPLE 110

Compound 110

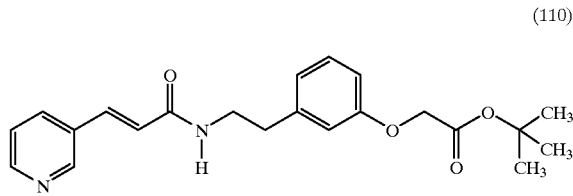
(110)

Properties: mp 87–88° C. (ethyl acetate-hexane)

$^1$H-NMR (CDCl$_3$) δ: 1.48 (9H, s), 2.86 (2H, t, J=6.7 Hz), 3.60–3.70 (2H, m), 4.51 (2H, s), 6.03 (1H, m), 6.44 (1H, d, J=15.7 Hz), 6.72–6.86 (3H, m), 7.18–7.32 (2H, m), 7.60 (1H, d, J=15.7 Hz), 7.74–7.79 (1H, m), 8.54 (1H, dd, J=4.8, 1.5 Hz), 8.70 (1H, d, J=1.9 Hz)

EXAMPLE 111

Compound 111

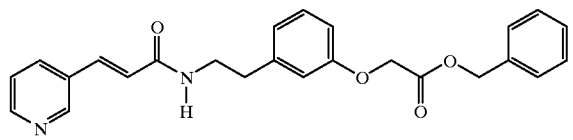
(111)

Properties: mp 114–116° C. (ethyl acetate-hexane)

$^1$H-NMR (CDCl$_3$) δ: 2.84 (2H, t, J=6.7 Hz), 3.58–3.68 (2H, m), 4.67 (2H, s), 5.22 (2H, s), 5.76 (1H, m), 6.40 (1H, d, J=15.7 Hz), 6.75–6.88 (3H, m), 7.19–7.38 (7H, m), 7.60 (1H, d, J=15.7 Hz), 7.77 (1H, m), 8.55 (1H, dd, J=4.8, 1.6 Hz), 8.71 (1H, d, J=2.5 Hz)

EXAMPLES 112 and 113

Compounds 112 and 113 were obtained by alkali or acid hydrolyzing the compound obtained in Example 99.

EXAMPLE 112

Compound 112

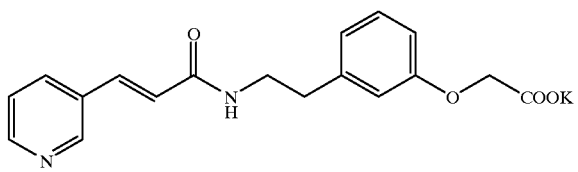
(112)

Properties: mp 272–275° C. (decomposition)

$^1$H-NMR (DMSO-d$_6$) δ: 2.71 (2H, t, J=7.2 Hz), 3.35–3.38 (2H, m), 4.05 (2H, s), 6.59–6.71 (3H, m), 6.83 (1H, d, J=15.9 Hz), 7.12 (1H, t, J=8.0), 7.39–7.49 (1H, m), 7.45 (1H, d, J=15.9 Hz), 7.98–8.04 (1H, m), 8.40 (1H, t, J=5.5 Hz), 8.52–8.55 (1H, m), 8.75–8.76 (1H, m)

EXAMPLE 113

Compound 113

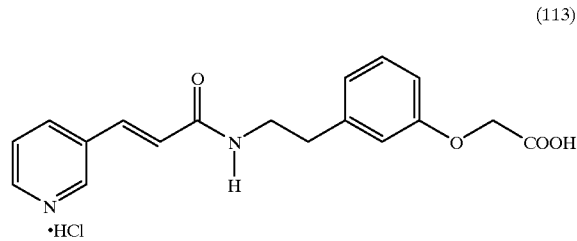
(113)

Properties: mp 180–190° C. (1N hydrochloric acid)

$^1$H-NMR (DMSO-d$_6$) δ: 2.77 (2H, t, J=7.2 Hz), 3.38–3.49 (2H, m), 4.65 (2H, s), 6:.72–6.86 (3H, m), 6.90 (1H, d, J=16.Hz), 7.17–7.25 (1H, m), 7.56 (1H, d, J=16.0 Hz), 7.87–7.95 (1H, m), 8.44 (1H, t, J=5.6 Hz), 8.51–8.55 (1H, m), 8.77–8.80 (1H, m), 9.03 (1H, s)

EXAMPLE 114

Synthesis of (E)-N-[3-[(methyl-carbamoyl)methoxy]phenethyl]-3-(3-pyridyl)-2-propenoic acid amide (Compound 114)

(Compound 114)

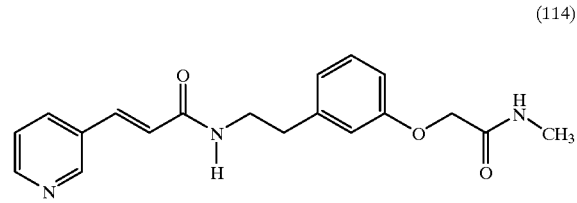
(114)

Methyl [3-[2-[(E)-3-(3-pyridyl)acryloylamino]-ethyl]phenoxy]acetate (0.34 g, 1.0 mmol) obtained in Example 94 was dissolved in methanol (6 ml) and 40% methylamine-methanol solution (0.8 ml) was added and stirred at room temperature for 17 hours. After concentrating the reaction mixture under reduced pressure, the residue was recrystallized to yield the titled compound (0.30 g, 88%).

Properties: mp 140–141° C. (ethyl acetate-methanol)

$^1$H-NMR (DMSO-d$_6$) δ: 2.65 (3H, d, J=5 Hz), 2.76 (2H, t, J=7 Hz), 3.43 (2H, td, J=7, 6 Hz), 4.44 (2H, s), 6.72 (1H, d, J=16 Hz), 6.78–6.87 (3H, m), 7.23 (1H, t, J=8 Hz), 7.41–7.50 (1H, m), 7.46 (1H, d, J=16 Hz), 7.95–8.03 (2H, m), 8.26 (1H, t, J=6 Hz), 8.55 (1H, dd, J=5, 1 Hz), 8.75 (1H, d, J=2 Hz)

EXAMPLES 115 to 125

Compounds 115 to 125 were obtained according to the method similar to that of Example 114.

EXAMPLE 115

Compound 115

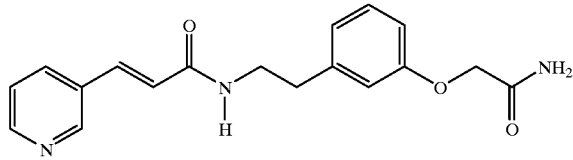
(115)

Properties: mp 146–147° C. (ethyl acetate-methanol)

$^1$H-NMR (DMSO-d) δ: 2.59 (2H, t, J=7 Hz), 3.25 (2H, td, J=7, 6 Hz), 4.23 (2H, s), 6.55 (1H, d, J=16 Hz), 6.61–6.69 (3H, m) 7.05 (1H, t, J=8 Hz), 7.23–7.33 (3H, m), 7.29 (1H, d, J=16 Hz), 7.81 (1H, d, J=8 Hz), 8.09 (1H, t, J=6 Hz), 8.38 (1H, dd, J=5, 1 Hz), 8.58 (1H, d, J=2 Hz)

EXAMPLE 116

Compound 116

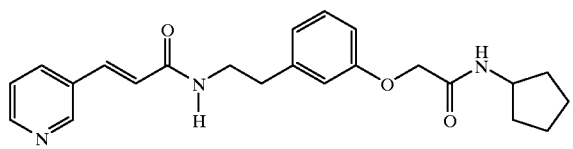
(116)

Properties: mp 154–155° C. (ethyl acetate-methanol)

$^1$H-NMR (DMSO-d$_6$) δ: 1.37–1.84 (8H, m), 2.75 (2H, t, J=7 Hz), 3.35–3.47 (2H, m), 4.01–4.12 (1H, m), 4.43 (2H, s), 6.73 (1H, d, J=16 Hz), 6.82–6.86 (3H, m), 7.22 (1H, t, J=8 Hz), 7.42–7.50 (1H, m), 7.46 (1H, d, J=16 Hz), 7.93–8.01 (2H, m), 8.27 (1H, t, J=6 Hz), 8.55 (1H, dd, J=5, 1 Hz), 8.75 (1H, d, J=2 Hz)

EXAMPLE 117

Compound 117

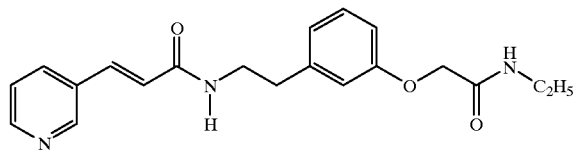
(117)

Properties: mp 137–139° C. (ethyl acetate-methanol)

$^1$H-NMR (DMSO-d$_6$) δ: 1.03 (3H, t, J=7 Hz), 2.76 (2H, t, J=7 Hz), 3.08–3.22 (2H, m), 3.37–3.48 (2H, m), 4.43 (2H, s), 6.72 (1H, d, J=16 Hz), 6.78–6.87 (3H, m), 7.23 (1H, t, J=8 Hz), 7.42–7.50 (1H, m), 7.46 (1H, d, J=16 Hz), 7.98 (1H, d, J=8 Hz), 8.09 (1H, t, J=5 Hz), 8.27 (1H, t, J=6 Hz), 8.55 (1H, dd, J=5, 1 Hz), 8.75 (1H, d, J=2 Hz)

EXAMPLE 118

Compound 118

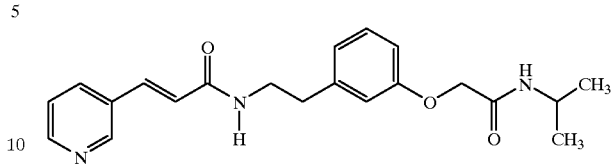
(118)

Properties: mp 143–144° C. (ethyl acetate-methanol)

$^1$H-NMR (DMSO-d$_6$) δ: 1.08 (6H, d, J=7 Hz), 2.76 (2H, t, J=7 Hz), 3.36–3.48 (2H, m), 3.86–4.03 (1H, m), 4.42 (2H, s), 6.73 (1H, d, J=16 Hz), 6.77–6.87 (3H, m), 7.22 (1H, t, J=8 Hz), 7.41–7.50 (1H, m), 7.46 (1H, d, J=16 Hz), 7.87 (1H, d, J=8 Hz) 7.98 (1H, d, J=8 Hz), 8.27 (1H, t, J=6 Hz), 8.55 (1H, dd, J=5, 2 Hz), 8.75 (1H, d, J=2 Hz)

EXAMPLE 119

Compound 119

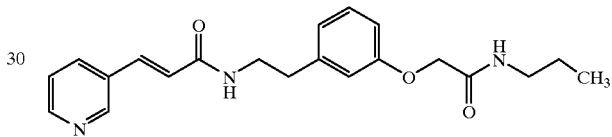
(119)

Properties: mp 140–142° C. (ethyl acetate-methanol)

$^1$H-NMR (DMSO-d$_6$) δ: 0.81 (3H, t, J=7 Hz), 1.34–1.52 (2H, m), 2.76 (2H, t, J=7 Hz), 3.08 (2H, td, J=7,6 Hz ), 3.35–3.47 (2H, m), 4.45 (2H, s), 6.72 (1H, d, J=16 Hz) 6.76–6.87 (3H, m) 7.23 (1H, t, J=8 Hz), 7.43–7.50 (1H, m), 7.46 (1H, d, J=16 Hz) 7.98 (1H, d, J=8 Hz), 8.06 (1H, t, J=6 Hz), 8.26 (1H, t, J=6 Hz) 8.55 (1H, dd, J=5, 2 Hz), 8.75 (1H, d, J=2 Hz)

EXAMPLE 120

Compound 120

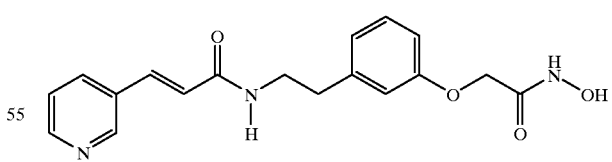
(120)

Properties: mp 145–148° C. (methanol)

$^1$H-NMR (DMSO-d$_6$) δ: 2.76 (2H, t, J=7 Hz), 3.37–3.47 (2H, m) 4.45 (2H, s), 6.73 (1H, d, J=16 Hz), 6.77–6.86 (3H, m), 7.22 (1H, t, J=8 Hz), 7.41–7.50 (1H, m), 7.46 (1H, d, J=16 Hz), 7.98 (1H, d, J=8 Hz), 8.26 (1H, t, J=6 Hz), 8.55 (1H, dd, J=5, 1 Hz), 8.75 (1H, d, J=2 Hz), 8.98 (1H, br s), 10.8 (1H, br)

EXAMPLE 121

Compound 121

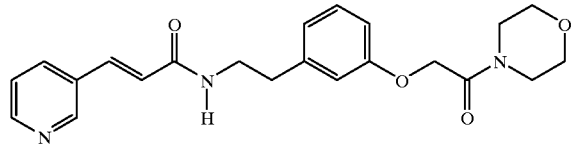

Properties: amorphous

¹H-NMR (CDCl₃) δ: 2.87 (2H, t, J=6.7 Hz), 3.56–3.71 (10H, m), 4.71 (2H, s), 5.91–5.99 (1H, br), 6.49 (1H, d, J=15.7 Hz), 6.77–6.89 (3H, m), 7.20–7.33 (2H, m), 7.61 (1H, d, J=15.7 Hz), 7.75–7.82 (1H, m), 8.54–8.58 (1H, m), 8.72 (1H, d, J=1.3 Hz)

EXAMPLE 122

Compound 122

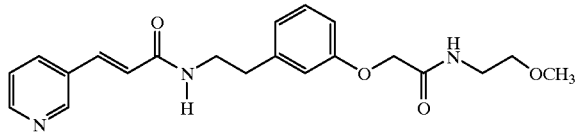

Properties: mp 122–123° C. (ethyl acetate-hexane)
¹H-NMR (CDCl₃) δ: 2.89 (2H, t, J=6.8 Hz), 3.34 (3H, s, 3.46–3.55 (4H, m), 3.62–3.72 (2H, m), 4.48 (2H, s), 5.94 (1H, m), 6.44 (2H, d, J=15.7 Hz), 6.76–6.95 (4H, m), 7.23–7.33 (2H, m), 7.62 (4H, d, J=15.7 Hz),7.75–7.80 (H, m), 8.56 (1H, dd, J=4.8, 1.4 Hz), 8.72 (5H, d, J=1.7 Hz)

EXAMPLE 123

Compound 123

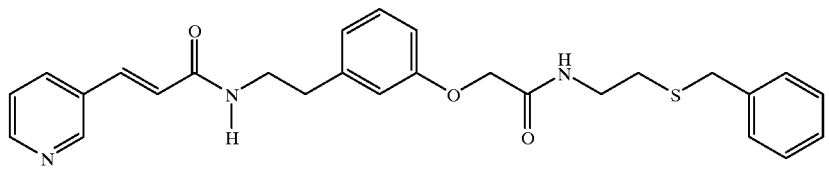

Properties: mp 148–149° C. (ether-methanol)

¹H-NMR (CDCl₃) δ: 2.88 (2H, t, J=6.7 Hz), 3.59–3.69 (2H, m) 4.54 (2H, s), 4.57 (2H, s) 6.44 (H, d, J=15.7 Hz), 6.51 (1H, m), 6.77–6.79 (2H, m z, 6.90 (6H, d, J=7.6 Hz), 7.03 (1H, m), 7.21–7.31 (3H, m), 7.59–7.61 (1H, m), 7.60 (1H, d, J=15.7 Hz), 7.71–7.77 (1H, m), 8.34 (1H, d, J=2.1 Hz), 8.48–8. 56 (2H, m) 8.68 (1H, d, J=2.0 Hz)

EXAMPLE 124

Compound 124

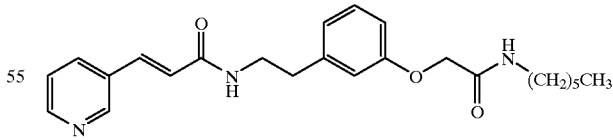

Properties: mp 108–110° C. (methylene chloride-hexane)
¹H-NMR (CDCl₃) δ: 2.59 (2H, t J=6.3 Hz), 2.88 (2H, t, J=6.9 Hz), 3.49 (2H, q, J=6.3 Hz), 3.62–3.71 (2H, m) 3.71 (2H, s), 4.47 (2H, s), 5.79 (2H, m),, 6 .38 (H, d, J=15.7 Hz), 6.77–6.92 (4H, m), 7.21–7.32 (7H, m), 7.62 (1H, d, J=15.7 Hz), 7.74–7.79 (1H, m), 8.56 (1H, dd, J=4.8, 1.6 Hz), 8.72 (2H, d, J=2.0 Hz)

EXAMPLE 125

Compound 125

Properties: mp 102–103° C. (ethyl acetate-hexane)
¹H-NMR (CDCl₃) δ: 0.84–0.91 (3H, m), 1.28–1.34 (6H, m), 1.46–1.57 (2H, m), 2.89 (2H, t, J=6.9 Hz), 3.28–3.38 (2H, m), 3.62–3.72 (2H, m), 4.47 (2H, s), 5.85 (1H, m), 6.43 (1H, d, J=15.7 Hz), 6.57 (1H, m), 6.76–6.81 (2H, m), 6.90 (1H, d, J=7.7 Hz), 7.23–7.33 (2H, m), 7.62 (1H, d, J=15.7 Hz), 7.75–7.81 (1H, m), 8.52 (1H, dd, J=4.8, 1.6 Hz), 8.72 (1H, d, J=2.0 Hz)

EXAMPLE 126

Synthesis of 3-[2-[[(E) -3-(3-pyridyl)-acryloyl] amino]ethyl]phenyl acetate (Compound 126)

(126)

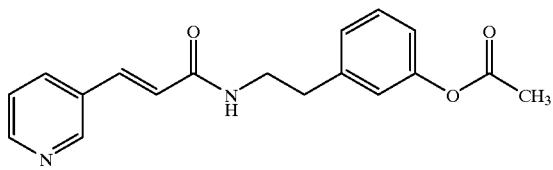

(E)-N-(3-hydroxyphenethyl)-3-(3-pyridyl)-2-propenoic acid amide (600 mg, 2.24 mmol) obtained in Example 81 was dissolved in pyridine (4.0 ml) and acetic anhydride (0.40 ml, 4.24 mmol) was added under ice-cooling and stirred at room temperature for 1.5 hours. Ethyl acetate was added to the reaction mixture and the mixture was washed with water and dried over magnesium sulfate. The solvent was distilled out under reduced pressure, and the residue was purified by silica gel column chromatography (methanol:dichloromethane=1:30) and recrystallized to yield the titled compound (574 mg, 82%).

Properties: mp 99° C. (ethyl acetate-hexane)
$^1$H-NMR (CDCl$_3$) δ: 2.29 (3H, s), 2.90 (2H, t, J=6.7 Hz), 3.61–3.71 (2H, m), 5.85–5.95 (1H, br), 6.44 (1H, d, J=15.7 Hz), 6.95–6.99 (2H, m), 6.99–7.11 (1H, m), 7.28–7.38 (2H, m), 7.60 (1H, d, J=15.7 Hz), 7.75–7.81 (1H, m), 8.54–8.56 (1H, m), 8.73 (1H, s)

EXAMPLE 127

Synthesis of (E)-N-[3-[(ethylcarbamoyl)oxy]-phenethyl]-3-(3-pyridyl)-2-propenoic acid amide (Compound 127)

(127)

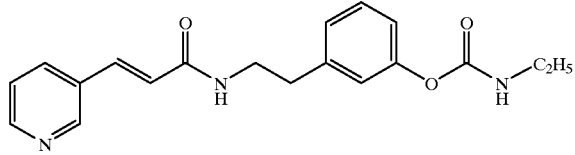

(E)-N-(3-hydroxyphenethyl)-3-(3-pyridyl)-2-propenoic acid amide (700 mg, 2.61 mmol obtained in Example 81 was dissolved in dimethylformamide (5.0 ml) and ethyl isocyanate (0.25 ml, 3.20 mmol) and triethylamine (0.40 ml, 2.89 mmol) were added under ice-cooling and stirred at room temperature for 2 hours. Ethyl acetate was added to the reaction mixture and the mixture was washed with water and dried over magnesium sulfate. The solvent was distilled out under reduced pressure, and the residue was purified by silica gel column chromatography (methanol:dichloromethane=1:30) and recrystallized to yield the titled compound (590 mg, 66%).

Properties: mp 130° C. (acetone)
$^1$H-NMR (CDCl$_3$) δ: 1.20 (3H, t, J=7.2 Hz), 2.88 (2H, t, J=6.5 Hz), 3.22–3.37 (2H, m), 3.59–3.69 (2H, m), 5.10–5.20 (1H, br), 6.00–6.10 (1H, br), 6.48 (1H, d, J=15.7 Hz), 6.98–7.07 (3H, m), 7.25–7.35 (2H, m), 7.59 (1H, d, J=15.7 Hz), 7.79 (1H, d, J=7.9 Hz), 8.52–8.56 (1H, m), 8.71–8.72 (1H, m)

EXAMPLES 128 to 134

Compounds 128 to 134 were obtained according to the method similar to that of Example 126 or 127.

EXAMPLE 128

Compound 128

(128)

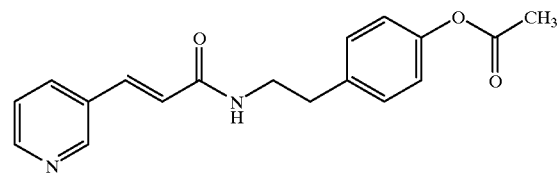

Properties: mp 118–121° C. (ethyl acetate)
$^1$H-NMR (CDCl$_3$) δ: 2.30 (3H, s), 2.89 (2H, t, J=7 Hz), 3.65 (2H, td, J=7, 6 Hz), 5.91 (1H, br t), 6.42 (1H, d, J=16 Hz) 7.03 (2H, d, J=9 Hz), 7.22 (2H, d, J=9 Hz), 7.30 (1H, dd, J=8,5 Hz), 7.61 (1H, d, J=16 Hz), 7.78 (1H, d, J=8 Hz), 8.55 (1H, d, J=5 Hz), 8.72 (1H, d, J=2 Hz)

EXAMPLE 129

Compound 129

(129)

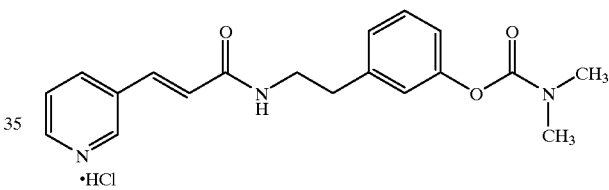

·HCl

Properties: mp 142–144° C. (ethanol)
$^1$H-NMR (DMSO-d$_6$) δ: 2.81 (2H, t, J=7.2 Hz), 2.90 (3H, s), 3.03 (3H, s), 3.39–3.50 (2H, m), 6.93–7.12 (3H, m), 6.95 (1H, d, J=16.0 Hz), 7.26–7.35 (1H, m), 7.57 (1H, d, J=16.0 Hz), 7.94–8.02 (1H, m), 8.53 (1H, t, J=5.5 Hz), 8.61 (1H, d, J=8.2 Hz), 8.83 (1H, d, J=5.0 Hz), 9.07 (1H, s)

EXAMPLE 130

Compound 130

(130)

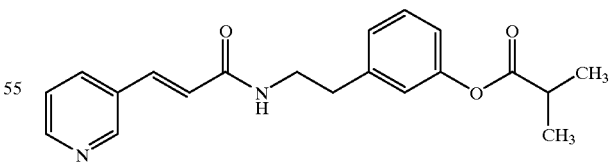

Properties: mp 96° C. (ethyl acetate-hexane)
$^1$H-NMR (CDCl$_3$) δ: 1.30 (6H, d, J=7.0 Hz) 2.80 (1H, septet, J=7.0 Hz), 2.90 (2H, t, J=6.6 Hz), 3.60–3.70 (2H, m), 5.85–5.95 (1H, br), 6.45 (1H, d, J=15.7 Hz), 6.92–6.98 (2H, m), 7.06–7.10 (1H, m), 7.25–7.46 (2H, m), 7.60 (1H, d, J=15.7 Hz), 7.76–7.82 (1H, m), 8.53–8.57 (1H, m), 8.72–8.74 (1H, m)

EXAMPLE 131

Compound 131

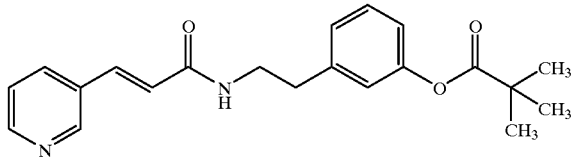
(131)

Properties: mp 106° C. (ethyl acetate-hexane)

¹H-NMR (CDCl₃) δ: 1.34 (9H, s), 2.90 (2H, t, J=6.6 Hz), 3.60–3.70 (2H, m), 5.85–5.95 (1H, br), 6.46 (1H, d, J=15.7 Hz), 6.91–6.96 (2H, m), 7.06–7.10 (1H, m), 7.26–7.38 (2H, m), 7.60 (1H, d, J=15.7 Hz), 7.77–7.83 (1H, m), 8.54–8.57 (1H, m), 8.74 (1H, br s)

EXAMPLE 132

Compound 132

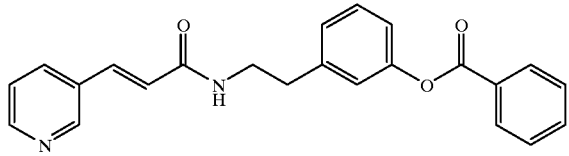
(132)

Properties: mp 114° C. (ethyl acetate-hexane)

¹H-NMR (CDCl₃) δ: 2.93 (2H, t, J=6.6 Hz), 3.63–3.73 (2H, m), 5.90–6.00 (1H, br), 6.47 (1H, d, J=15.7 Hz), 7.08–7.16 (3H, m), 7.26–7.69 (6H, m), 7.76–7.82 (1H, m), 8.15–8.21 (2H, m), 8.53–8.66 (1H, m), 8.73–8.74 (1H, m)

EXAMPLE 133

Compound 133

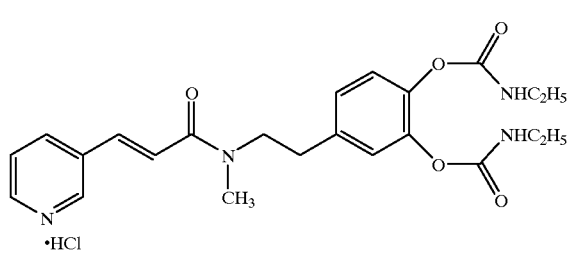
(133)

·HCl

Properties: amorphous

¹H-NMR (DMSO-d₆, 100° C.) δ: 0.99 (3H, t, J=7.2 Hz), 1.09 (3H, t, J=7.2 Hz), 2.85 (2H, t, J=7.3 Hz), 2.95–3.11 (7H, m), 3.69 (2H, t, J=7.3 Hz), 7.03–7.19 (3H, m), 7.15 (1H, d, J=15.4 Hz), 7.42 (1H, d, J=15.4 Hz), 7.53–7.60 (1H, m), 8.21–8.26 (1H, m), 8.57–8.61 (1H, m), 8.87 (1H, s)

EXAMPLE 134

Compound 134

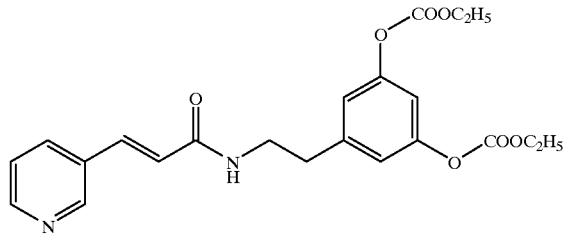
(134)

Properties: mp 85–88° C. (ethyl acetate-hexane)

¹H-NMR (CDCl₃) δ: 1.37 (6H, t, J=7.1 Hz), 2.88–2.96 (2H, m), 3.61–3.70 (2H, m), 4.30 (4H, q, J=7.1 Hz), 5.80–5.86 (1H, m), 6.46 (1H, d, J=15.7 Hz), 6.95–6.99 (3H, m), 7.27–7.33 (1H, m), 7.60 (1H, d, J=15.7 Hz), 7.77–7.83 (1H, m), 8.55–8.58 (1H, m), 8.75–8.76 (1H, m)

EXAMPLE 135

Synthesis of (E)-N-(3,4-dimethoxyphenethyl)-N-methyl-3-(3-pyridyl)-2-propenoic acid thioamide hydrochloride (Compound 135)

(Compound 135)

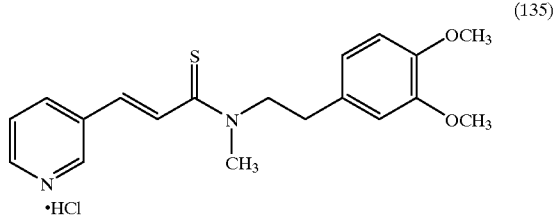
(135)

·HCl

A mixture of (E)-N-(3,4-dimethoxyphenethyl)-N-methyl-3-(3-pyridyl)-2-propenoic acid amide (1.63 g) obtained in Example 84, Lawesson's reagent (1.03 g) and xylene (10 ml) was heated and refluxed for 2 hours. After the solvent was distilled out under reduced pressure, the residue was purified by silica gel column chromatography (chloroform: methanol=30:1) to yield (E)-N-(3,4-dimethoxyphenethyl)-N-methyl-3-(3-pyridyl)-2-propenoic acid thioamide (1.66 g, 97%) as an oily material. Then hydrogen chloride-methanol was added thereto to produce its hydrochloride and recrystallized in a mixed solvent of ethyl acetate and methanol to yield the titled compound (1.68 g, 89%).

Properties: mp 167–169° C. (ethyl acetate-methanol)

¹H-NMR (DMSO-d₆, 100° C.) δ: 2.79 (2H, t, J=7.1 Hz), 3.00 (3H, s), 3.67–3.74 (2H, m), 3.67 (3H, s), 3.72 (3H, s), 6.70–6.83 (3H, m), 7.15 (1H, d, J=15.1 Hz), 7.37 (1H, d, J=15.1 Hz), 7.66–7.73 (1H, m), 8.33–8.37 (1H, m), 8.63–8.66 (1H, m), 8.93 (1H, br s)

EXAMPLES 136 to 139

Compounds 136 to 139 were obtained according to the method similar to that of Example 135.

EXAMPLE 136

Compound 136

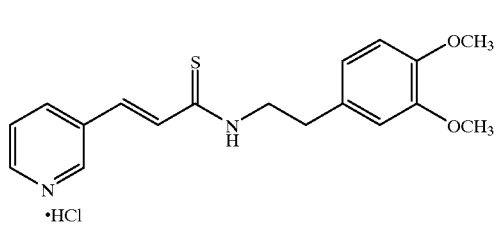
(136)
·HCl

Properties: mp 182–187° C. (methanol)

¹H-NMR (DMSO-$d_6$) δ: 2.88–2.95 (2H, m), 3.72 (3H, s), 3.75 (3H, s), 3.81–3.92 (2H, m), 6.76–6.91 (3H, m), 7.44 (1H, d, J=15.6 Hz), 7.77 (1H, d, J=15.6 Hz), 7.96 (1H, dd, J=8.2, 5.4 Hz), 8.58 (1H, d, J=8.2 Hz), 8.82 (1H, d, J=5.4 Hz), 9.08 (1H, br s), 10.62 (1H, t, J=5.2 Hz)

EXAMPLE 137

Compound 137

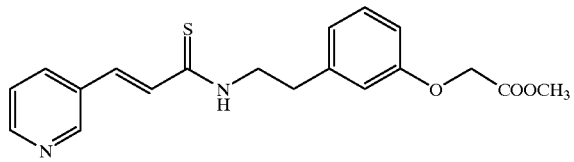
(137)

Properties: mp 102–104° C. (dichloromethane-ether)

¹H-NMR (CDCl₃) δ: 3.03 (2H, t, J=6.8 Hz), 3.78 (3H, s), 4.04–4.14 (2H, m), 4.64 (2H, s), 6.74–6.92 (3H, m), 6.83 (1H, d, J=15.4 Hz), 7.20–7.33 (2H, m), 7.60–7.72 (1H, br), 7.76 (1H, d, J=15.4 Hz), 7.76–7.84 (1H, m), 8.50–8.55 (1H, m), 8.71 (1H, d, J=2.1 Hz)

EXAMPLE 138

Compound 138

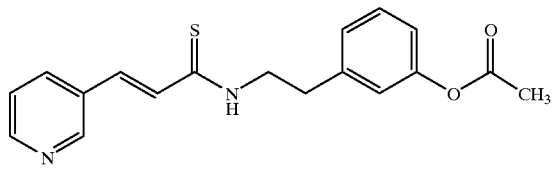
(138)

Properties: amorphous

¹H-NMR (CDCl₃) δ: 2.29 (3H, s), 3.06 (2H, t, J=6.7 Hz), 4.03–4.15 (2H, m), 6.84 (1H, d, J=15.4 Hz), 6.95–7.01 (2H, m), 7.09–7.15 (1H, m), 7.25–7.41 (2H, m), 7.50–7.62 (1H, br), 7.75 (1H, d, J=15.4 Hz), 7.78–7.86 (1H, m), 8.51–8.56 (1H, m), 8.73–8.76 (1H, m)

EXAMPLE 139

Compound 139

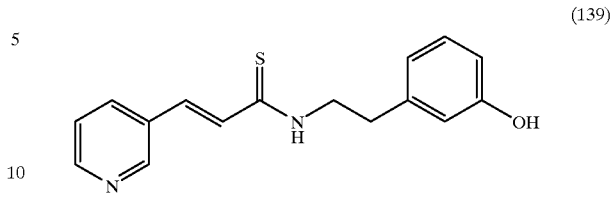
(139)

Properties: mp 199–201° C. (methanol)

¹H-NMR (DMSO-$d_6$) δ: 2.87 (2H, t, J=7.5 Hz), 3.77–3.89 (2H, m), 6.58–6.71 (3H, m), 7.05–7.15 (1H, m), 7.16 (1H, d, J=15.5 Hz), 7.41–7.49 (1H, m), 7.70 (1H, d, J=15.5 Hz), 7.96–8.04 (1H, m), 8.54–8.59 (1H, m), 8.76–8.79 (1H, m), 9.32 (1H, s), 10.20–10.30 (1H, br)

EXAMPLES 140 to 147

(E)-N-(3,4-dimethoxyphenethyl)-N-methyl-3-(3-pyridyl)-2-propenoic acid amide obtained in Example 84 as a starting material was treated with an inorganic or organic acid to obtain Compounds 140 to 147.

EXAMPLE 140

Compound 140

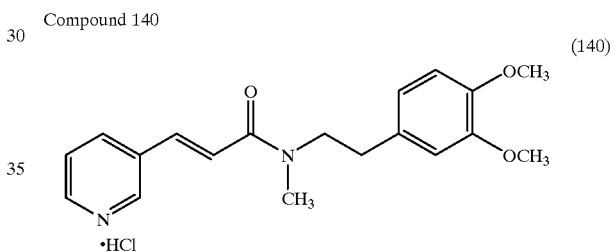
(140)
·HCl

Properties: mp 165–170° C. (isopropanol)

¹H-NMR (DMSO-$d_6$, 100° C.) δ: 2.78 (2H, t, J=7.1 Hz), 3.00 (3H, s) 3.66 (3H, s), 3.66–3.72 (2H, m), 3.72 (3H, s), 6.70–6.84 (3H, m), 7.08 (1H, d, J=14.8 Hz), 7.36 (1H, d, J=14.8 Hz), 7.53–7.60 (1H, m), 8.17–8.22 (1H, m), 8.57–8.60 (1H, m), 8.84 (1H, s)

EXAMPLE 141

Compound 141

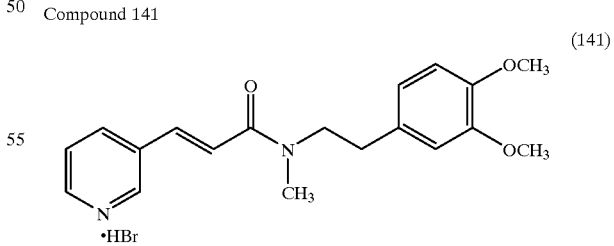
(141)
·HBr

Properties: mp 201–205° C. (ether-methanol)

¹H-NMR (DMSO-$d_6$, 100° C.) δ: 2.78 (2H, t, J=7.Hz), 3.00 (3H, s), 3.66 (3H, s), 3.66–3.72 (2H, m), 3.72 (3H, s), 6.70–6.82 (3H, m), 7.11 (1H, d, J=15.6 Hz), 7.37 (1H, d, J=15.6 Hz), 7.60–7.67 (1H, m), 8.26–8.31 (1H, m), 8.61–8.65 (1H, m), 8.88 (1H, S)

EXAMPLE 142

Compound 142

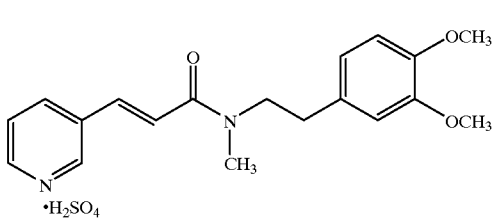
(142)

Properties: mp 138° C. (ether-methanol)

¹H-NMR (DMSO-d$_6$, 100° C.) δ: 2.78 (2H, t, J=7.Hz), 3.00 (3H, s), 3.66 (3H, s), 3.66–3.72 (2H, m), 3.72 (3H, s), 6.71–6.81 (3H, m), 7.07–7.16 (1H, m), 7.33–7.41 (1H, m), 7.63–7.71 (1H, m), 8.29–8.34 (1H, m), 8.62–8.66 (1H, m), 8.88 (1H, s)

EXAMPLE 143

Compound 143

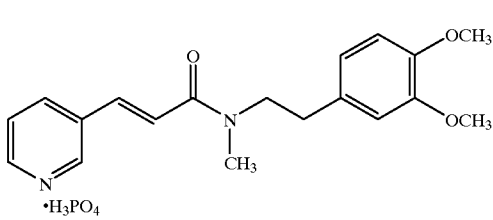
(143)

Properties: mp 152° C. (ether-methanol)

¹H-NMR (DMSO-d$_6$, 100° C.) δ: 2.78 (2H, t, J=7.1 Hz), 2.99 (3H, s), 3.63–3.71 (2H, m), 3.67 (3H, s), 3.72 (3H, s), 6.70–6.84 (3H, m), 6.96–7.04 (1H, m), 7.20–7.40 (2H, m), 7.93–7.98 (1H, m), 8.48–8.52 (1H, m), 8.72 (1H, s)

EXAMPLE 144

Compound 144

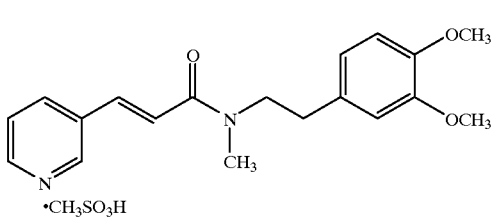
(144)

Properties: amorphous

¹H-NMR (DMSO-d$_6$, 100° C.) δ: 2.44 (3H, s), 2.78 (2H, t, J=7.1 Hz), 3.00 (3H, s), 3.67 (3H, s), 3.66–3.72 (2H, m), 3.72 (3H, s), 6.71–6.84 (3H, m), 7.09 (1H, d, J=15.2 Hz), 7.36 (1H, d, J=15.2 Hz), 7.58–7.66 (1H, m), 8.23–8.28 (1H, m), 8.60–8.63 (1H, m), 8.85 (1H, s)

EXAMPLE 145

Compound 145

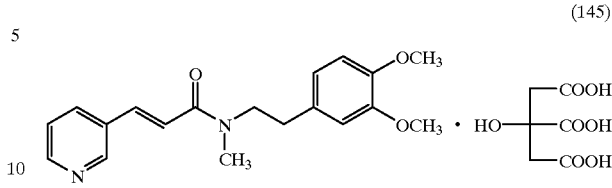
(145)

Properties: mp 129.5–131.5° C. (acetone)

¹H-NMR (DMSO-d$_6$, 100° C.) δ: 2.71–2.82 (6H, m), 2.99 (3H, s), 3.63–3.71 (2H, m), 3.67 (3H, s), 3.72 (3H, s), 6.70–6.76 (1H, m), 6.79–6.84 (2H, m), 6.95–7.04 (1H, m), 7.29–7.40 (2H, m), 7.92–7.97 (1H, m), 8.48–8.52 (1H, m), 8.72 (1H, s)

EXAMPLE 146

Compound 146

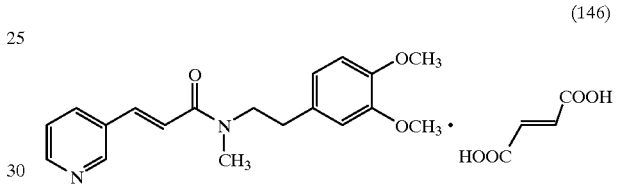
(146)

Properties: mp 128.5–130° C. (ethanol)

¹H-NMR (DMSO-d$_6$, 100° C.) δ: 2.78 (2H, t, J=7.1 Hz), 2.99 (3H, s), 3.67 (3H, s), 3.67 (2H, t, J=7.1 Hz), 3.72 (3H, s), 6.63 (2H, s), 6.70–6.76 (1H, m), 6.80–6.85 (2H, m), 6.95–7.04 (1H, m), 7.29–7.39 (2H, m), 7.92–7.97 (1H, m), 8.48–8.52 (1H, m), 8.72 (1H, s)

EXAMPLE 147

Compound 147

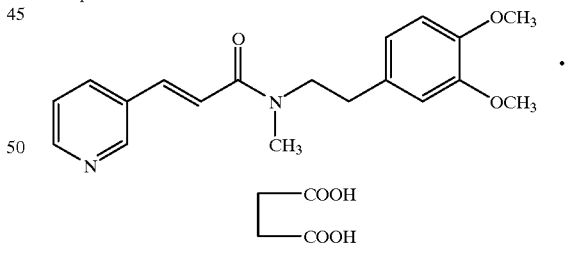
(147)

Properties: mp 104–106° C. (acetone)

¹H-NMR (DMSO-d$_6$, 100° C.) δ: 2.43 (4H, s), 2.78 (2H, t, J=7.1 Hz), 2.99 (3H, s), 3.63–3.72 (2H, m), 3.67 (3H, s), 3.72 (3H, s), 6.70–6.85 (3H, m), 6.95–7.04 (1H, m), 7.30–7.40 (2H, m), 7.92–7.97 (1H, m), 8.48–8.52 (1H, m), 8.73 (1H, s)

EXAMPLE 148

Compounds 148 to 152 were obtained according to the method similar to that of Example 112.

EXAMPLE 148

Compound 148 (148)

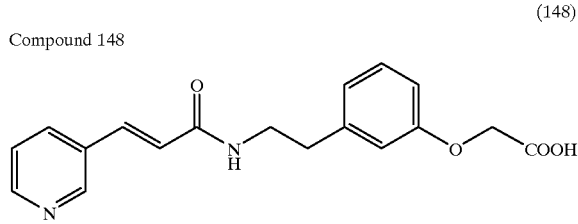

Properties: solid

¹H-NMR (DMSO-d$_6$) δ: 2.75 (2H, t, J=7.3 Hz), 3.33–3.47 (2H, m), 4.65 (2H, S), 6.71–6.85 (3H, m), 6.72 (1H, d, J=16.0 Hz), 7.21 (1H, t, J=7.7 Hz), 7.41–7.47 (1H, m), 7.46 (1H, d, J=16.Hz), 7.94–8.00 (1H, m), 8.25 (1H, t, J=5.4 Hz), 8.53–8.56 (1H, m), 8.75 (1H, s)

EXAMPLE 149

Compound 149 (149)

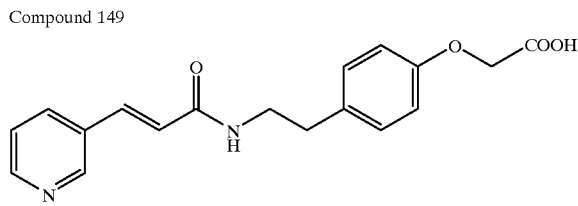

Properties: solid

¹H-NMR (DMSO-d$_6$) δ: 2.72 (2H, t, J=7.3 Hz), 3.33–3.44 (2H, m), 4.62 (2H, S), 6.72 (1H, d, J=16.Hz), 6.84 (2H, d, J=8.6 Hz), 7.15 (2H, d, J=8.6 Hz), 7.41–7.47 (1H, m), 7.45 (1H, d, J=16.Hz), 7.94–8.00 (1H, m), 8.23 (1H, t, J=5.6 Hz) 8.53–8.57 (1H, m), 8.74–8.76 (1H, m)

EXAMPLE 150

Compound 150 (150)

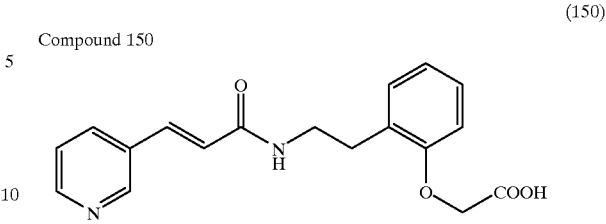

Properties: solid

¹H-NMR (DMSO-d$_6$) δ: 2.82 (2H, t, J=7.2 Hz), 3.30–3.50 (2H, m), 4.72 (2H, S), 6.73 (1H, d, J=15.9 Hz), 6.83–6.94 (2H, m), 7.13–7.22 (2H, m), 7.40–7.47 (1H, m), 7.45 (1H, d, J=15.9 Hz), 7.93–8.01 (1H, m), 8.21 (1H, t, J=5.6 Hz), 8.52–8.56 (1H, m), 8.73–8.75 (1H, m)

EXAMPLE 151

Compound 151 (151)

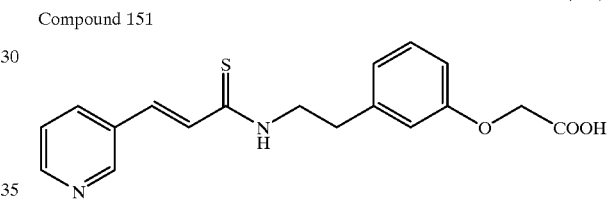

Properties: solid

¹H-NMR (DMSO-d$_6$) δ: 2.94 (2H, t, J=7.4 Hz), 3.80–3.92 (2H, m), 4.65 (2H, S), 6.73–6.90 (3H, m), 7.17 (1H, d, J=15.5 Hz), 7.18–7.28 (1H, m), 7.41–7.49 (1H, m), 7.70 (1H, d, J=15.5 Hz), 7.98–8.03 (1H, m), 8.54–8.58 (1H, m), 8.77–8.79 (1H, m), 10.27 (1H, t, J=4.9 Hz)

EXAMPLE 152

Compound 152 (152)

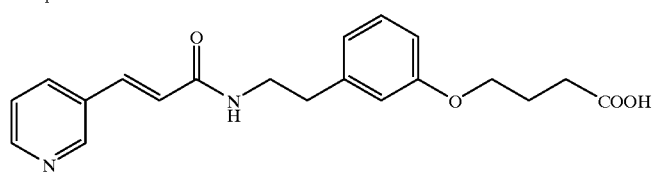

Properties: solid

¹H-NMR (DMSO-d₆) δ: 1.85–1.99 (2H, m), 2.37 (2H, t, J=7 Hz), 2.75 (2H, t, J=7 Hz), 3.37–3.47 (2H, m), 3.96 (2H, t, J=6 Hz), 6.73 (1H, d, J=16 Hz), 6.74–6.81 (3H, m), 7.20 (1H, t, J=8 Hz), 7.43–7.50 (1H, m), 7.46 (1H, d, J=16 Hz), 7.97 (1H, d, J=8 Hz), 8.24 (1H, t, J=6 Hz), 8.55 (1H, dd, J=5, 1 Hz), 8.75 (1H, d, J=2 Hz)

EXAMPLES 153 and 154

Compounds 153 and 154 were obtained according to the method similar to that of Example 9.

EXAMPLE 153

Compound 153

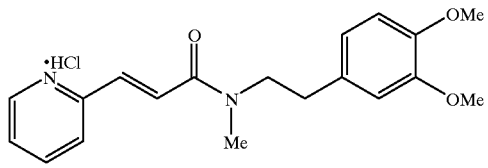
(153)

Properties: mp 172–174° C. (methanol-ether)

¹H-NMR (DMSO-d₆, 100° C.) δ: 2.79 (2H, t, J=7.0 Hz), 3.00 (3H, s), 3.66–3.72 (8H, m), 6.70–6.83 (3H, m), 7.30–7.50 (3H, m), 7.72–7.76 (1H, m), 7.94–8.02 (1H, m), 8.61–8.64 (1H, m)

EXAMPLE 154

Compound 154

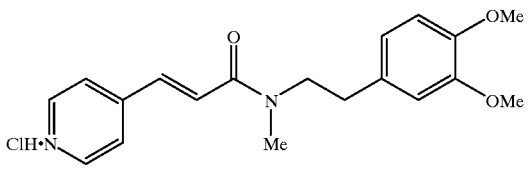
(154)

Properties: mp 192–195° C. (methanol-ether)

¹H-NMR (DMSO-d₆, 100° C.) δ: 2.78 (2H, t, J=7.Hz), 3.01 (3H, s), 3.65–3.71 (8H, m), 6.69–6.80 (3H, m), 7.29 (2H, m), 7.86–7.90 (2H, m), 8.70–8.73 (2H, m)

EXAMPLE 155

Synthesis of (E) -N-[2-(3,4-dimethoxyphenyl)-2-oxoethyl]-N-methyl-3-(3-pyridyl)-2-propenoic acid amide (Compound 155)

(Compound 155)

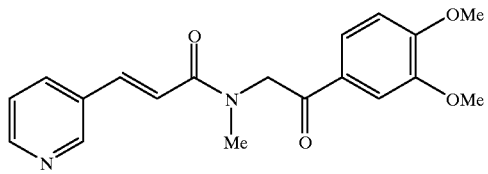
(155)

To 3',4'(14.65 g, 81 mmol), ether (250 ml) and chloroform (100 ml) were added and stirred under ice-cooling. Bromine (4.1 ml) was dissolved in chloroform (22 ml) and dropwise added to the reaction mixture over 1 hour. After the reaction mixture was stirred at room temperature for 1 hour, the reaction mixture was sequentially washed with water, aqueous saturated sodium bicarbonate solution and water. The organic phase was dried over magnesium sulfate and the solvent was distilled out under reduced pressure. The residue was purified by silica gel column chromatography (dichloromethane:ethyl acetate=30:1) to yield 2-bromo-1-(3, 4-dimethoxyphenyl) ethanone (14.90 g, 71%).

¹H-NMR (CDCl₃) δ: 3.95 (3H, s), 3.97 (3H, s), 4.41 (2H, s), 6.91 (1H, d, J=8 Hz), 7.55 (1H, d, J=2 Hz), 7.62 (1H, dd, J=8 Hz, 2 Hz)

To isopropanol (200 ml), 40% aqueous methylamine solution (133 ml) was added and stirred under ice-cooling. 2-Bromo-1-(3,4-dimethoxyphenyl)ethanone (8.47 g, 33 mmol) was dissolved in isopropanol (10 ml) and dichloromethane (10 ml) and dropwise added to the reaction mixture over 1 hour. After the dropwise addition, the mixture was stirred for 15 minutes under ice-cooling. The solvent in the reaction mixture was distilled out at room temperature under reduced pressure and the precipitated crystal was filtered to yield 1-(3,4-dimethoxyphenyl)-2-(methylamino)ethanone hydrobromide (6.36 g, 67%).

¹H-NMR (CDCl₃+MeOH-d₄) δ: 2.81 (3H, s), 3.96 (3H, s), 3.98 (3H, s), 4.60 (2H, s), 6.99 (1H, d, J=8Hz), 7.53 (1H, d, J=2 Hz), 7.64 (1H, dd, J=8 Hz, 2 Hz)

Dichloromethane (50 ml) and triethylamine (2.69 ml, 19.30 mmol) were sequentially added to trans-3-(3-pyridyl) acrylic acid (1.44 g, 9.65 mmol) and stirred for 10 minutes. Then, pivaloyl chloride (1.18 ml, 9.65 mmol) was added and stirred for 13 minutes. 1-(3,4-Dimethoxyphenyl)-2-(methylamino)ethanone hydrobromide (2.79 g, 9.65 mmol) was dissolved in dichloromethane (4 ml) and triethylamine (1.34 ml, 9.65 mmol), added to the reaction mixture and stirred at room temperature for 30 minutes. After the reaction mixture was washed with water and aqueous saturated sodium bicarbonate solution, the organic phase was dried over magnesium sulfate and the solvent was distilled out under reduced pressure. The residue was purified by silica gel column chromatography (dichloromethane:methanol= 10:1) to yield a crude product. The crude product was recrystallized to yield the titled compound (1.84 g, 5.41 mmol, 56%).

Properties: mp 193–194° C. (dichloromethane/methanol/hexane)

¹H-NMR (DMSO-d₆, 100° C.) δ: 2.95 (3H, s), 3.83 (3H, s), 3.87 (3H, s), 4.97 (2H, br), 7.09 (1H, d, J=8 Hz), 7.26 (1H, br), 7.34 (1H, dd, J=8 Hz, 5 Hz), 7.48 (1H, d, J=15 Hz), 7.51 (1H, d, J=2 Hz), 7.65 (1H, dd, J=8 Hz, 2 Hz), 8.01 (1H, m), 8.49–8.52 (1H, m), 8.79 (1H, m)

EXAMPLE 156

Synthesis of (E)-N-[2-(3,4-dimethoxyphenyl)-2-(hydroxyimino)ethyl]-N-methyl-3-(3-pyridyl)-2-propenoic acid amide (Compound 156)

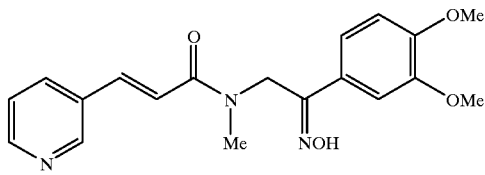

(156)

Acetic acid (3 ml) was added to (E)-N-[2-(3,4-dimethoxyphenyl)-2-oxoethyl]-N-methyl-3-(3-pyridyl)-2-propenoic acid amide (165 mg, 0.5 mmol) and allowed to stand at −20° C. After acetic acid was solidified, 50% aqueous hydroxylamine solution (0.62 ml, 10 mmol) was added under ice-cooling and reacted at the same temperature. After warming to room temperature and reacting for further 22 hours, water (10 ml) and ethyl acetate (10 ml) were added and extracted three times with ethyl acetate (10 ml). The organic layer was washed sequentially with water (40 ml) and aqueous saturated sodium chloride solution (40 ml) and dried over anhydrous magnesium sulfate (10 g). The drying agent was removed out and the filtrate was concentrated. The resulting dry product was purified by a column chromatography using silica gel (20 g) (elution with dichloromethane: methanol=100:3.5). After purification, the product was recrystallized in ethyl acetate (5 ml) and n-hexane (15 ml) to yield the titled compound (91 mg, yield 51%).

Properties: mp 172–173° C. (ethyl acetate-hexane)

$^1$H-NMR (DMSO-$d_6$, 100° C.) δ: 11.2 (1H, brs), 8.78–8.88 (1H, d), 8.50–8.53 (1H, dd, $J_1$=1.4 Hz, $J_2$=5.4 Hz), 8.00–8.04 (1H, d, J=1.88 Hz), 7.42–7.50 (1H, d), 7.33–7.40 (1H, m), 7.10–7.18 (2H, m), 7.18, 7.19 (1H, d, 4.4 Hz), 6.89–6.93 (1H, d), 4.82 (2H, s), 3.75 (3H, s), 3.72 (3H, s), 2.91 (3H, s)

EXAMPLE 157

Synthesis of (E)-N-[2-(3-hydroxyphenyl)-2-hydroxyethyl-3-(3-pyridyl)-2-propenoic acid amide (Compound 157)

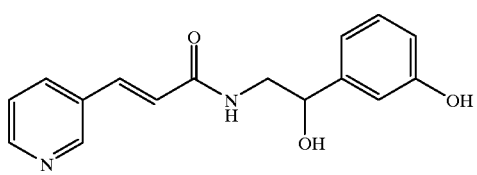

(157)

Pivaloyl chloride (5.17 ml, 1.05 eq.) was added to a solution of trans-3-(3-pyridyl)acrylic acid (5.96 g, 40 mmol) and triethylamine (5.6 ml, 40 mmol) in dichloromethane (80 ml) and stirred at room temperature for 10 minutes. A solution of dl-α-aminomethyl-3-hydroxybenzylalcohol hydrochloride (7.58 g, 40 mmol) and triethylamine (11.1 ml, 80 mmol) in dichloromethane (80 ml) was added and stirred at room temperature for 1 hour. The precipitated crystal was collected to yield the titled compound (7.51 g, 66%).

Properties: solid $^1$H-NMR (DMSO-$d_6$) δ: 3.10–3.30 (1H, m), 3.31–3.55 (1H, m), 4.50–4.65 (1H, m), 5.50 (1H, d, J=4.3 Hz), 6.62–6.67 (1H, m), 6.75–6.88 (3H, m), 7.09–7.16 (1H, m), 7.42–7.50 (2H, m), 7.94–8.00 (1H, m), 8.24 (1H, t,5.7 Hz), 8.53–8.57 (1H, m), 8.75 (1H, d, J=1.9 Hz), 9.33 (1H, s)

EXAMPLE 158

Synthesis of (E)-N-[2-hydroxy-2-(3-methoxy-4-hydroxyphenyl)ethyl]-N-methyl-3-(3-pyridyl)-2-propenoic acid amide (Compound 158)

The titled compound was obtained according to the method similar to that of Example 157.

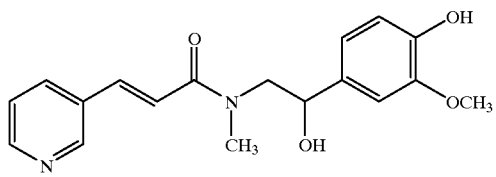

(158)

Properties: amorphous $^1$H-NMR (DMSO-$d_6$, 150° C.) δ: 3.00 (3H, s), 3.47–3.70 (2H, m), 3.76 (3H, s), 4.66–4.91 (2H, m), 6.71 (1H, d, J=8.Hz), 6.78 (1H, dd, J=8.0,1.8 Hz), 6.93 (1H, d, J=1.8 Hz), 7.00 (1H, d, J=15.6 Hz), 7.25–7.42 (1H, m), 7.34 (1H, d, J=15.6 Hz), 7.79–8.02 (2H, m), 8.49 (1H, dd, J=4.8,1.6 Hz), 8.71 (1H, d, J=2.2 Hz)

EXAMPLE 159

Synthesis of ethyl [3-[1-hydroxy-2-((E) -3-(3-pyridyl)acryloylamino]ethyl]phenoxy]acetate (Compound 159)

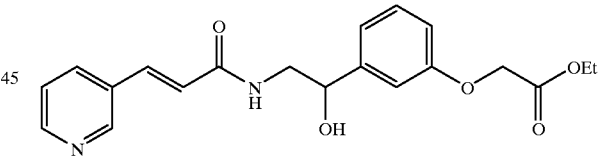

(159)

(E)-N-[2-(3-hydroxyphenyl)-2-hydroxyethyl]-3-(3-pyridyl)-2-propenoic acid amide (5.68 g, 20 mmol) and ethyl chloroacetate (5.2 ml, 48 mmol) were dissolved in dimethylformamide (60 ml) and potassium carbonate (8.28 g, 60 mmol) was added and stirred at 50° C. for 7 hours. After allowing to cool, insoluble materials were filtered out and water was added to the filtrate, extracted with ethyl acetate and dried over magnesium sulfate. The solvent was distilled out under reduced pressure and the residue was purified by silica gel column chromatography (chloroform:hexane:methanol=20:2:1) and dried under reduced pressure to yield the titled compound (3.80 g, 51%).

Properties: amorphous $^1$H-NMR (CDCl$_3$) δ: 1.26 (3H, t, J=7.1 Hz), 3.31–3.51 (1H, m), 3.68–3.88 (1H, m), 4.22 (2H, q, J=7.1 Hz), 4.59 (2H, s), 4.78–4.92 (1H, m), 5.04 (1H, s), 6.50 (1H, d, J=15.7 Hz), 6.71–6.83 (1H, m), 6.93–7.04 (2H, m), 7.06–7.28 (3H, m), 7.51 (1H, d, J=15.7 Hz), 7.62–7.95 (1H, m), 8.44 (1H, dd, J=4.6,1.5 Hz), 8.54 (1H, d, J=1.8 Hz)

EXAMPLE 160

Synthesis of (E)-N-(3-hydroxyphenacyl)-3-(3-pyridyl)-2-propenoic acid amide (Compound 160)

(160)

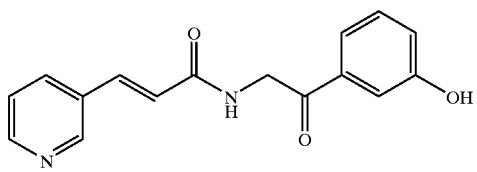

To a solution of (E)-N-[2-(3-hydroxyphenyl)-2-hydroxyethyl]-3-(3-pyridyl)-2-propenoic acid amide (568 g, 2 mmol) in dimethylformamide (4 ml), pyridinium dichromate (1.28 g, 1.7 eq.) was added under ice-cooling and stirred at room temperature for 10 hours. Then, water (4 ml) was added. Tar materials were filtered out on Celite and water (4 ml) was added to the filtrate and extracted with ethyl acetate. The solvent was distilled out under reduced pressure and the residue was solidified in ethanol to yield the titled compound (171 mg, 30%).

Properties: solid $^1$H-NMR (DMSO-d$_6$) δ: 4.73 (2H, d, J=6 Hz), 6.95 (1H, d, J=16 Hz), 7.05–7.09 (1H, m), 7.33–7.55 (5H, m), 8.01–8.05 (1H, m), 8.42–8.59 (2H, m), 8.79–8.80 (1H, m), 9.88 (1H, s)

EXAMPLE 161

Compound 161 was obtained according to the method similar to that of Example 160.

Compound 161                                          (161)

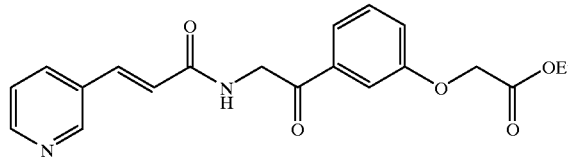

Properties: solid $^1$H-NMR (CDCl$_3$) δ: 1.32 (3H, t, J=7.1 Hz), 4.29 (2H, q, J=7.1 Hz), 4.70 (2H, s), 4.89 (2H, d, J=4.3 Hz), 6.65 (1H, d, J=15.7 Hz), 6.75–6.90 (1H, m), 7.19–7.25 (1H, m), 7.33 (1H, dd, J=7.9,4.8 Hz), 7.41–7.49 (1H, m), 7.52–7.54 (1H, m), 7.63–7.67 (1H, m), 7.69 (1H, d, J=15.7 Hz), 7.81–7.87 (1H, m), 8.60 (1H, dd, J=4.8,1.5 Hz), 8.78 (1H, d, J=1.9 Hz)

EXAMPLE 162

Synthesis of (E)-N-methyl-N-(3-methoxy-4-hydroxyphenacyl)-3-(3-pyridyl)-2-propenoic acid amide (Compound 162)

(Compound 162)                                          (162)

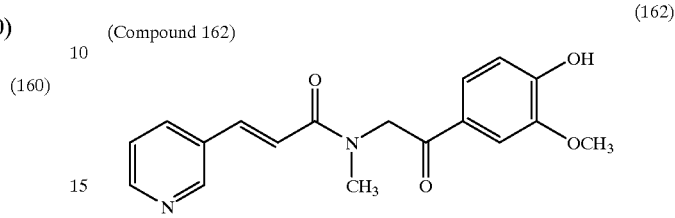

To a solution of (E)-N-[2-hydroxy-2-(3-methoxy-4-hydroxyphenyl)ethyl]-N-methyl-3-(3-pyridyl)-2-propenoic acid amide (656 mg, 2 mmol) in dioxane (12 ml), 2,3-dichloro-5,6-dicyano-1,4-benzoquinone (468 mg, 2 mmol) was added under argon and stirred at room temperature for 2 hours. After the precipitated crystal was filtered out, the solvent was distilled out under reduced pressure and the residue was purified by column chromatography (chloroform:methanol=50:1) and dried under reduced pressure to yield the titled compound (362 mg, 56%).

Properties: amorphous $^1$H-NMR (DMSO-d$_6$, 100° C.) δ: 3.13 (3H, brs), 3.88 (3H, s), 4.97 (2H, brs), 6.87–6.99 (1H, m), 7.04–7.62 (5H, m), 7.93–8.17 (1H, m), 8.43–8.64 (1H, m), 8.70–8.95 (1H, m), 9.59 (1H, brs)

EXAMPLE 163

Compound 163 was obtained according to the method similar to that of Example 155.

Compound 163                                          (163)

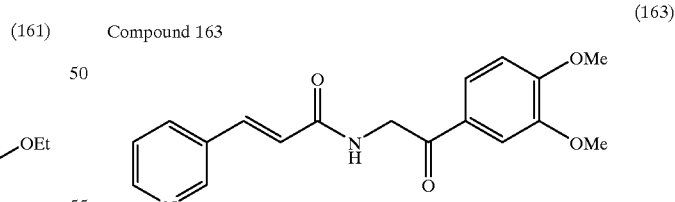

Properties: solid $^1$H-NMR (CDCl$_3$) δ: 3.97 (3H, s), 3.98 (3H, S), 4.88 (2H, d, J=4.2 Hz), 6.66 (1H, d, J=15.7 Hz), 6.90 (1H, brs), 6.95 (1H, d, J=8.5 Hz), 7.34 (1H, dd, J=7.9, 4.8 Hz), 7.54 (1H, d, J=2.0 Hz), 7.69 (1H, d, J=15.9 Hz), 7.70 (1H, d, J=2.Hz), 7.83–7.85 (1H, m), 8.59 (1H, dd, J=4.8, 1.4 Hz), 8.78 (1H, d, J=1.8 Hz)

EXAMPLE 164

Synthesis of (E)-N-[2-(3,4-dimethoxyphenyl)-2-(methylthio)ethyl]-3-(3-pyridyl)-2-propenoic acid amide (Compound 164)

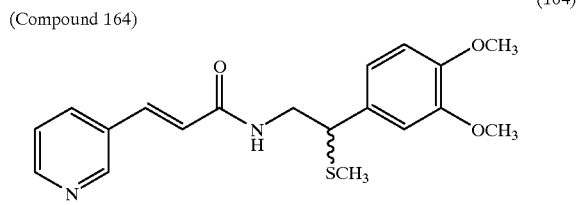

(164)

To a solution of sodium methanethiolate (0.62 g, 8.8 mmol) in methanol (20 ml), trans-3,4-dimethoxy-β-nitrostyrene (1.42 g, 8 mmol) was added and stirred at room temperature for 5 minutes. Further, acetic acid (0.46 ml) was added and stirred for 5 minutes. After evaporating methanol to a half amount under reduced pressure, water was added and extracted with dichloromethane and the organic layers were combined, washed with water and dried over sodium sulfate. The solvent was distilled out under reduced pressure and the residue was isolated and purified by silica gel column chromatography (hexane:ethyl acetate=10:1) to yield 2-(3,4-dimethoxyphenyl)-2-(methylthio)nitroethane (1.24 g, 60%).

Under argon, a solution of 2-(3,4-dimethoxyphenyl)-2-(methylthio)nitroethane (1.22 g, 4.8 mmol) in tetrahydrofuran (20 ml) was dropwise added to an ice-cooled and stirred solution of lithium aluminum hydride (0.47 g) in tetrahydrofuran (10 ml). After stirring at room temperature for 30 minutes, water (0.47 ml), 15% aqueous sodium hydroxide solution (0.47 g) and water (1.14 ml) were sequentially added dropwise to the reaction mixture under ice-cooling and stirring. A small amount of potassium carbonate was added and stirred for a few minutes. Inorganic salts were filtered out and washed with tetrahydrofuran and the filtrate was concentrated under reduced pressure and dried to yield a crude oily 2-(3,4-dimethoxyphenyl)-2-(methylthio)ethylamine (0.98 g).

To a solution of the crude oily 2-(3,4-dimethoxy-phenyl)-2-(methylthio)ethylamine (0.96 g) and trans-3-(3-pyridyl) acrylic acid (0.63 g, 4.2 mmol) in dimethylformamide (10 ml), diethylphosphoric cyanide (0.69 ml) and triethylamine (1.17 ml) were sequentially added under ice-cooling and stirred for 10 minutes under ice-cooling. Aqueous sodium bicarbonate solution was added to the reaction mixture and extracted with ethyl acetate. The organic layers were combined, washed with water and aqueous saturated sodium chloride solution and dried over magnesium sulfate. The solvent was distilled out under reduced pressure and the residue was purified by silica gel column chromatography (hexane: chloroform:ethanol=8:2:1) to yield the titled compound (788 mg, 47%).

Properties: amorphous $^1$H-NMR (CDCl$_3$) δ: 2.00 (3H, s), 3.64–3.99 (3H, m), 3.87 (3H, s), 3.88 (3H, s), 6.06–6.30 (1H, m), 6.43 (1H, d, J=15.8 Hz), 6.74–6.97 (3H, m), 7.29 (1H, dd, J=8.0, 4.8 Hz), 7.61 (1H, d, J=15.8 Hz), 7.70–7.86 (1H, m), 8.55 (1H, dd, J=4.8, 1.6 Hz), 8.69 (1H, d, J=2.0 Hz)

EXAMPLE 165

Synthesis of (E)-N-[2-(3,4-dimethoxyphenyl)-2-oxoethyl]-N-methyl-3-(3-pyridyl)-2-propenoic acid thioamide (Compound 165)

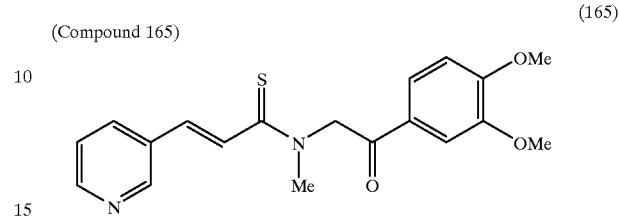

(165)

Lawesson's reagent (300 mg) and anhydrous toluene (20 ml) were added to the compound (390 mg) obtained in Example 155 and refluxed under argon. After 4 hours, ethyl acetate (30 ml) and water (30 ml) were added and the ethyl acetate phase was separated and the aqueous phase was further extracted twice with ethyl acetate (20 ml). The ethyl acetate phases were combined, washed sequentially with water (50 ml) and aqueous saturated sodium chloride solution (50 ml) and dried over anhydrous magnesium sulfate. The solvent was distilled out and purified by silica gel column chromatography (dichloromethane:methanol= 1000:15) to yield the titled compound (61 mg, 14%).

Properties: solid $^1$H-NMR (DMSO-d$_6$) δ: 3.53 (3H, s), 3.94 (3H, s), 3.97 (3H, s), 5.60 (2H, s), 6.93 (1H, d, J=15 Hz), 7.35 (1H, d, J=15 Hz), 7.55 (1H, d, J=1.9 Hz), 7.63–7.82 (1H, m), 7.78–7.87 (1H, m), 8.49–8.67 (3H, m), 8.80 (1H, d, J=2.0 Hz)

EXAMPLE 166

Effects of the compounds of the present invention on proteinuria, serum cholesterol, blood urea nitrogen and serum creatinine in anti-GBM nephritic mice BALB/c mice (5 weeks old, purchased from Nippon Charles Liver) were quarantined and adapted for about 1 week before subjecting to experiments. These mice were divided into several groups for the experiments so that average body weights and standard deviations were almost identical in all groups. Mouse anti-GBM (glomerular basement membrane) nephritis was caused by immunizing the mice with rabbit γ-globulin (1 mg) with Freund's complete adjuvant and intravenously injecting rabbit anti-mouse GBM serum on the fifth day from the immunization. Each compound tested was forcedly orally administered via an oral sonde almost simultaneously with the intravenous injection of the anti-GBM serum. On the 5th and 10th days from the intravenous injection, urine was taken by a plastic metabolic cage and proteinuria was measured (Ohtsuka Tonein TP2). On the 11th day, blood was taken by cutting the carotid and serum cholesterol (S—Ch), blood urea nitrogen (BUN) and serum creatinine (S—Cr) were measured by Toshiba TBA-380 autoanalyzer. The results are shown in Table 1.

TABLE 1-1

| Compound No. | Proteinuria 5th day | Proteinuria 10th day | Serum Parameter S-Ch | Serum Parameter BUN | Serum Parameter S-Cr | Total Evaluation |
|---|---|---|---|---|---|---|
| 2 | + | +++ | − | − | + | 13 |
| 6 | ++ | +++ | + | − | − | 16 |
| 8 | − | ++ | − | − | − | 6 |
| 9 | + | ++ | + | + | + | 12 |
| 12 | − | + | + | + | +++ | 8 |
| 13 | + | +++ | − | + | + | 13 |
| 14 | − | + | + | + | − | 7 |
| 15 | + | + | + | + | + | 11 |
| 18 | + | ++ | ++ | ++ | − | 13 |
| 20 | ++ | + | + | + | ++ | 13 |
| 21 | ++ | − | + | + | ++ | 9 |
| 25 | + | ++ | +++ | + | + | 13 |
| 29 | ++ | ++ | ++ | + | + | 16 |
| 33 | ++ | ++ | ++ | − | + | 7 |
| 38 | ++ | +++ | ++ | + | + | 19 |
| 39 | ++ | +++ | ++ | ++ | ++ | 21 |
| 41 | + | − | +++ | − | ++ | 8 |
| 42 | + | + | − | + | ++ | 9 |
| 45 | ++ | + | + | − | − | 10 |
| 49 | − | + | + | + | ++ | 7 |
| 50 | ++ | +++ | +++ | − | − | 18 |
| 52 | + | + | + | + | ++ | 10 |
| 53 | − | + | − | − | +++ | 6 |
| 55 | + | +++ | +++ | ++ | − | 17 |
| 62 | − | +++ | +++ | ++ | + | 14 |
| 70 | ++ | +++ | +++ | ++ | ++ | 22 |
| 71 | + | +++ | − | ++ | ++ | 17 |
| 73 | +++ | +++ | +++ | + | − | 22 |
| 75 | ++ | +++ | ++ | + | + | 19 |
| 81 | +++ | +++ | +++ | +++ | ++ | 26 |
| 84 | +++ | +++ | ++ | +++ | − | 23 |
| 85 | +++ | +++ | ++ | + | − | 21 |
| 87 | +++ | + | ++ | +++ | ++ | 19 |
| 89 | ++ | ++ | ++ | + | − | 15 |
| 90 | ++ | +++ | − | + | + | 17 |
| 91 | + | +++ | ++ | − | − | 14 |
| 93 | − | − | ++ | +++ | +++ | 8 |
| 95 | + | + | + | ++ | − | 9 |
| 99 | +++ | +++ | − | + | ++ | 21 |
| 100 | − | + | + | + | + | 6 |
| 101 | − | ++ | − | − | ++ | 8 |
| 102 | + | ++ | − | − | − | 9 |
| 114 | +++ | +++ | +++ | ++ | + | 24 |
| 115 | − | + | ++ | ++ | +++ | 10 |
| 116 | + | + | + | ++ | + | 10 |
| 127 | +++ | ++ | ++ | − | − | 17 |
| 133 | + | + | + | + | + | 9 |
| 135 | − | + | + | + | + | 6 |
| 140 | + | ++ | ++ | ++ | + | 14 |
| 155 | ++++ | ++++ | +++ | + | − | 28 |
| 156 | + | + | + | − | − | 7 |
| 158 | + | + | + | − | − | 7 |
| 159 | ++ | + | + | − | − | 10 |
| 160 | +++ | + | ++ | − | − | 14 |
| 161 | ++ | + | + | − | − | 10 |
| 162 | +++ | + | + | − | − | 13 |
| 165 | +++ | +++ | +++ | + | − | 22 |

−; Not effective
+; tendency of inhibiting
++; significantly improved (p < 0.05)
+++; significantly improved (p < 0.01)
++++; significantly improved (p < 0.001)
Total Evaluation = 3 × (number of + in proteinuria) + (number of + in serum parameter)

EXAMPLE 167

BALB/c male mice were adapted in a feeding chamber for 1 week before subjecting to experiments. Nephritis was induced by subcutaneously injecting an emulsion of rabbit γ-globulin and Freund's complete adjuvant on the back in a dose amount of 1.0 mg per mouse and, after 5 days (on the zeroth day), intravenously injecting rabbit anti-mouse GBM serum in a dose amount of 0.1 ml per mouse. After 1 day from the injection of anti-serum, the glomeruli were isolated through sieves with different sizes and washed twice. Each compound to be tested ($10^{-6}$ M) was added while the solvent was added to the control groups. The glomeruli were incubated in RPMI-1640 serum-free medium for 48 hours. The amount of production of active TGF-β1 was determined by measuring the supernatant itself after the incubation for 48 hours in ELSA method. Further, the supernatant was treated with hydrochloric acid and the pH was returned with sodium hydroxide. The total amount of TGF-β1 produced in the supernatant was measured in ELISA method. The protein concentration in the medium was also measured as glomeruli protein concentration. The inhibition rate was calculated by the following equation. The results are shown in Tables 2 and 3.

Inhibition rate (%)=100×(value of control group−value of sample)/(value of control group)

TABLE 2

| Compound No. | Inhibition rate (%) of production of active TGF-β1 |
|---|---|
| 73 | 78 |
| 81 | 58 |
| 84 | 40 |
| 148 | 45 |

TABLE 3

| Compound No. | Inhibition rate (%) of production of total TGF-β1 |
|---|---|
| 2 | 56.7 |
| 12 | 37.8 |
| 29 | 32.6 |
| 33 | 49.8 |
| 49 | 59.0 |
| 51 | 56.8 |
| 55 | 75.7 |
| 62 | 31.9 |
| 73 | 84.0 |
| 84 | 85.0 |
| 120 | 56.9 |
| 135 | 47.1 |
| 149 | 35.9 |
| 151 | 19.1 |
| 148 | 78.3 |
| 153 | 31.0 |
| 154 | 53.4 |

EXAMPLE 168

Effects of the compounds of the present Invention on the Glomerular TGF-β1 Expression in IgA Nephropahty in Mice Methods Male ddY mice of 9 weeks old were used, each group consisting of 5 mice. One kidney was nephrectomized from the mice on the zero week, and carbon was intravenously injected from 1 week after the nephrectomy (once per week, total three times). In Experiment 1, administration was commenced on the final day of the intravenous injection of carbon. In Experiment 2, administration was commenced after the mice were allowed to stand for 10 weeks from the intravenous injection of carbon. In both Experiments, the administration was continued for 5 weeks and then the kidney was taken, fixed with methaqualone and embedded in paraffin. Sliced specimens were stained as TGF-β1 positive area by the immunohistochemical analysis method using TGF-β1 antibody.

Staining was evaluated according to the Kagami et al. method (Kagami S., Border WA., Ruslahti E., Noble B.: Coordinated expression of β integrins and transforming growth factor-β induced matrix proteins in glomerulonephritis. Lab Invest 1993, 69, 68–76) and is shown as staining score (Index). The results are shown in Table 4.

TABLE 4

| Group | | Experiment 1 (Index) | Experiment 2 (Index) |
|---|---|---|---|
| Control | | 0.20 ± 0.02 | 0.41 ± 0.04 |
| Compound 99 | 0.1 mg/kg | 0.17 ± 0.04 (15) | 0.29 ± 0.04 (29) |
| | 0.5 mg/kg | 0.13 ± 0.03 (35) | |
| | 2.0 mg/kg | 0.11 ± 0.03 (45) | 0.18 ± 0.05 (56)* |

Mean ± S.E.
*p < 0.05 vs control,
(): % inhibition

Compound 99 had a tendency of inhibiting glomerular TGF-β1 expression in Experiment 1 but significantly inhibited the increase of Index in Experiment 2. It was confirmed that the compound 99 had an inhibiting action on the production of TGF-β1 in vivo.

INDUSTRIAL APPLICABILITY

According to the present invention, there may be provided anti nephritic agents and TGF-β inhibitors comprising pyridylacrylamide derivatives as effective ingredients, as well as novel pyridylacrylamide derivatives useful for anti nephritic agents and TGF-β inhibitors.

What is claimed is:

1. A method for treating nephritis comprising
   (a) providing pharmaceutical composition comprising a pyridylacrylamide compound represented by the following formula (I):

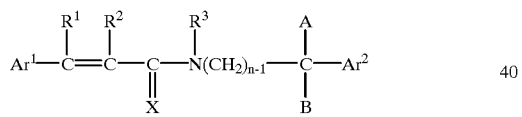

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and,
   (b) administering the pharmaceutical composition in a pharmaceutically effective amount, thereby treating the nephritis.

2. The method of claim 1, wherein $Ar^1$ is a pyridyl group substituted by at least one selected from the group consisting of a halogen atom, a $C_{1-6}$ alkyl group, a $C_{1-6}$ alkoxy group and a $C_{1-6}$ alkoxy-carbonyl group.

3. The method of claim 1, wherein $Ar^2$ is a phenyl group substituted by at least one selected from the group consisting of a halogen atom, a hydroxyl group, an optionally substituted amino group, an optionally substituted $C_{1-6}$ alkoxy group, a $C_{2-6}$ alkenyl-oxy group, an aryloxy group, an optionally substituted $C_{1-6}$ alkyl group, an aryl group, a $C_{1-6}$ alkylthio group, a carboxyl group, a $C_{1-6}$ alkoxy-carbonyl group, a sulfamoyl group; and, a —O—CO—$R^4$ group in which $R^4$ is a $C_{1-6}$ alkyl, aryl, $C_{1-6}$ alkoxy or optionally substituted amino group.

4. A method for inhibiting a TGF-β comprising
   (a) providing composition comprising a pyridylacrylamide compound represented by the following formula (I):

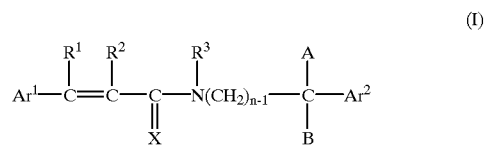

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3; or a pharmaceutically acceptable salt thereof; and,
   (b) contacting the composition with the TGF-β in an amount sufficient to inhibit the TGF-β.

5. A method for treating a patient with a TGF-β-involving disease comprising
   (a) providing pharmaceutical composition comprising a pyridylacrylamide compound represented by the following formula (I):

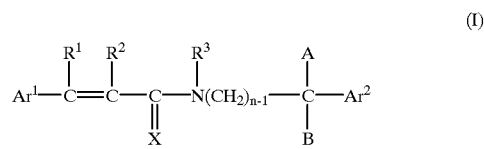

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the patient with the TGF-β-involving disease.

6. The method of claim 1 or claim 5, wherein the pharmaceutical composition is administered as an oral formulation.

7. The method of claim 1 or claim 5, wherein the pharmaceutical composition is administered as an parenteral formulation.

8. A method for treating liver cirrhosis comprising
(a) providing pharmaceutical composition comprising a pyridylacrylamide compound represented by the following formula (I):

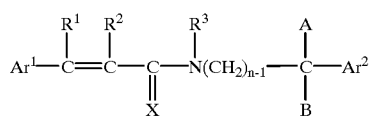

(I)

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the liver cirrhosis.

9. A method for treating a fibrosis comprising
(a) providing pharmaceutical composition comprising a pyridylacrylamide compound represented by the following formula (I):

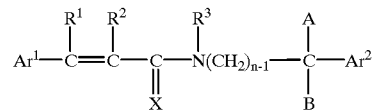

(I)

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the fibrosis.

10. A method for treating chronic renal insufficiency comprising
(a) providing pharmaceutical composition comprising a pyridylacrylamide compound represented by the following formula (I):

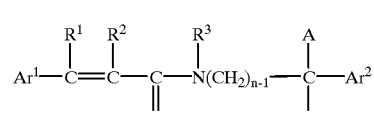

(I)

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the chronic renal insufficiency.

11. A method for treating a pulmonary fibrosis comprising
(a) providing pharmaceutical composition comprising a pyridylacrylamide compound represented by the following formula (I):

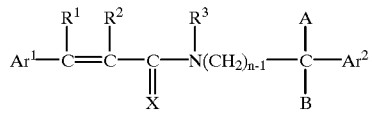

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the pulmonary fibrosis.

12. A method for treating a diabetic nephropathy comprising (a) providing pharmaceutical composition comprising a pyridylacrylamide compound represented by the following formula (I):

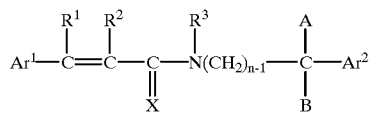

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the diabetic nephropathy.

13. A method for treating a retinopathy comprising
(a) providing pharmaceutical composition comprising a pyridylacrylamide compound represented by the following formula (I):

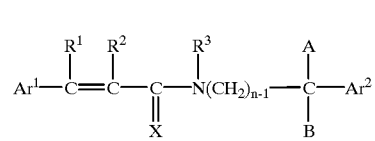

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof; and, (b) administering the pharmaceutical composition in a pharmaceutically effective amount, thereby treating the retinopathy.

14. A pyridylacrylamide compound represented by the following formula (I'):

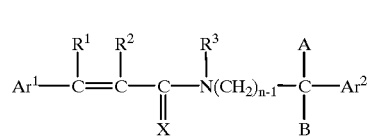

wherein $Ar^1$ is a substituted or unsubstituted pyridyl group, $Ar^2$ is a substituted or unsubstituted phenyl group, $R^1$ is a hydrogen atom, a $C_{1-6}$ alkyl group or an aryl group, $R^2$ is a hydrogen atom, a $C_{1-6}$ alkyl group, a cyano group or a $C_{1-6}$ alkoxy-carbonyl group, $R^3$ is a hydrogen atom or an optionally substituted $C_{1-6}$ alkyl group, X is an oxygen or sulfur atom, A and B are same or different and each represent a hydrogen atom, a hydroxyl group, a $C_{1-6}$ alkoxy group or a $C_{1-6}$ alkylthio group, or A and B together form an oxo or thioxo group, or a group represented by the formula: =N—Y in which Y is a di($C_{1-6}$ alkyl)amino, hydroxyl, aralkyloxy or $C_{1-6}$ alkoxy group, or a group represented by the formula: —$Z^1$—M—$Z^2$— in which $Z^1$ and $Z^2$ are same or different and each represent an oxygen or sulfur atom or an imino group optionally substituted by a $C_{1-6}$ alkyl group, and M is an alkylene group having 2 to 4 chain members or a 1,2-phenylene group, or A is a hydroxyl group and B is a 1-$C_{1-6}$ alkyl-imidazol-2-yl group, and n is an integer of 1 to 3, or a pharmaceutically acceptable salt thereof, with the proviso that $Ar^2$ is not a phenyl group substituted by any sulfonyl group; $Ar^1$ is not a 3-pyridyl group; $Ar^2$ is not 3,5-di-tert-butyl-4-hydroxyphenyl group, $R^1$, $R^2$ and $R^3$ each representing a hydrogen atom, X is an oxygen atom, A and B each represent a hydrogen atom, and n is 1.

15. The compound of claim 14, wherein $Ar^1$ is a pyridyl group substituted by at least one selected from the group consisting of a halogen atom, a $C_{1-6}$ alkyl group, a $C_{1-6}$ alkoxy group and a $C_{1-6}$ alkoxy-carbonyl group.

16. The compound of claim 14, wherein $Ar^2$ is a phenyl group substituted by at least one selected from the group consisting of a halogen atom, a hydroxyl group, an optionally substituted amino group, an optionally substituted $C_{1-6}$ alkoxy group, a $C_{2-6}$ alkenyl-oxy group, an aryloxy group, an optionally substituted $C_{1-6}$ alkyl group, an aryl group, a $C_{1-6}$ alkylthio group, a carboxyl group, a $C_{1-6}$ alkoxy-carbonyl group, a sulfamoyl group and a —O—CO—$R^4$ group in which $R^4$ is a $C_{1-6}$ alkyl, aryl, $C_{1-6}$ alkoxy or optionally substituted amino group.

* * * * *